(12) United States Patent
Miyazaki et al.

(10) Patent No.: US 10,944,949 B2
(45) Date of Patent: Mar. 9, 2021

(54) BODY CAVITY OBSERVATION SYSTEM, LAPAROSCOPE SYSTEM, TROCAR APPARATUS, AND OPERATION METHOD OF BODY CAVITY OBSERVATION SYSTEM

(71) Applicant: Kyocera Corporation, Kyoto (JP)

(72) Inventors: Kazuto Miyazaki, Tachikawa (JP); Takaharu Fujii, Tokorozawa (JP); Takashi Saotome, Ome (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 16/408,494

(22) Filed: May 10, 2019

(65) Prior Publication Data

US 2019/0268581 A1 Aug. 29, 2019

Related U.S. Application Data

(63) Continuation of application No. PCT/JP2017/040482, filed on Nov. 9, 2017.

(30) Foreign Application Priority Data

Nov. 10, 2016 (JP) .............................. JP2016-220049

(51) Int. Cl.
| | |
|---|---|
| *H04N 9/73* | (2006.01) |
| *A61B 1/313* | (2006.01) |
| *A61B 1/00* | (2006.01) |
| *A61B 1/05* | (2006.01) |
| *A61B 17/34* | (2006.01) |
| *H04N 5/225* | (2006.01) |

(52) U.S. Cl.
CPC ............... *H04N 9/735* (2013.01); *A61B 1/00* (2013.01); *A61B 1/00009* (2013.01); *A61B 1/051* (2013.01); *A61B 1/3132* (2013.01); *A61B 17/34* (2013.01); *A61B 17/3423* (2013.01); *H04N 5/2257* (2013.01); *H04N 2005/2255* (2013.01)

(58) Field of Classification Search
CPC ............................ H04N 9/735; H04N 5/2257
See application file for complete search history.

(56) References Cited

U.S. PATENT DOCUMENTS

| | | | |
|---|---|---|---|
| 8,197,399 B2 * | 6/2012 | Bayer | A61B 1/05 600/113 |
| 9,044,185 B2 * | 6/2015 | Bayer | G06T 7/70 |
| 9,364,248 B2 * | 6/2016 | Yacoubian | A61B 17/00234 |
| 9,706,908 B2 * | 7/2017 | Sidar | A61B 1/00177 |
| 9,949,623 B2 * | 4/2018 | Lang | A61B 1/00006 |

(Continued)

FOREIGN PATENT DOCUMENTS

| | | |
|---|---|---|
| JP | 2009195558 A | 9/2009 |
| JP | 5266065 B2 | 8/2013 |

(Continued)

*Primary Examiner* — Irfan Habib
(74) *Attorney, Agent, or Firm* — Viering, Jentschura & Partner MBB

(57) ABSTRACT

A trocar with camera has a camera section. The camera section obtains a trocar image that includes an image of a white part on a surface of a puncture member by performing imaging when the puncture member of a trocar shaft is exposed at a deployed position. A white balance setting section for trocar image sets a white balance for the trocar image based on the image of the white part in the trocar image.

7 Claims, 43 Drawing Sheets

(56) References Cited

U.S. PATENT DOCUMENTS

| | | | | |
|---|---|---|---|---|
| 10,123,684 B2* | 11/2018 | Sidar | ................... | A61B 1/042 |
| 10,258,222 B2* | 4/2019 | Levin | ................... | A61B 1/05 |
| 10,271,713 B2* | 4/2019 | Ofir | ................... | A61B 1/051 |
| 10,398,287 B1* | 9/2019 | Genova | ............. | A61B 1/00135 |
| 10,463,399 B2* | 11/2019 | Savvouras | ............. | A61B 1/015 |
| 10,516,865 B2* | 12/2019 | Sidar | ................... | G06T 5/40 |
| 10,517,464 B2* | 12/2019 | Salman | ............. | A61B 1/00177 |
| 10,524,645 B2* | 1/2020 | Davidson | ............... | A61B 1/045 |
| 10,595,714 B2* | 3/2020 | Aizenfeld | ............. | A61B 1/015 |
| 2008/0033450 A1* | 2/2008 | Bayer | ............... | A61B 17/3417 |
| | | | | 606/108 |
| 2008/0161646 A1* | 7/2008 | Gomez | ............... | A61B 1/2676 |
| | | | | 600/169 |
| 2015/0272694 A1* | 10/2015 | Charles | ................ | A61B 90/37 |
| | | | | 600/202 |

FOREIGN PATENT DOCUMENTS

| | | |
|---|---|---|
| JP | 2016016053 A | 2/2016 |
| WO | 2007070831 A2 | 6/2007 |

* cited by examiner

F I G. 15A
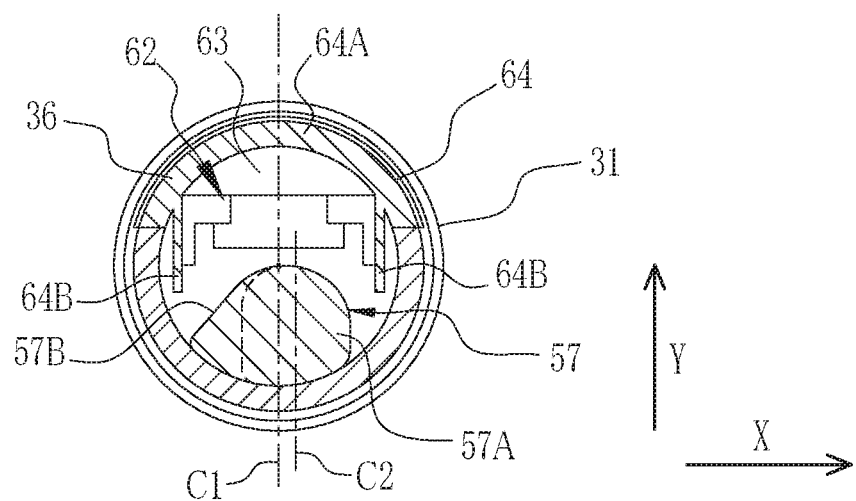
F I G. 15B
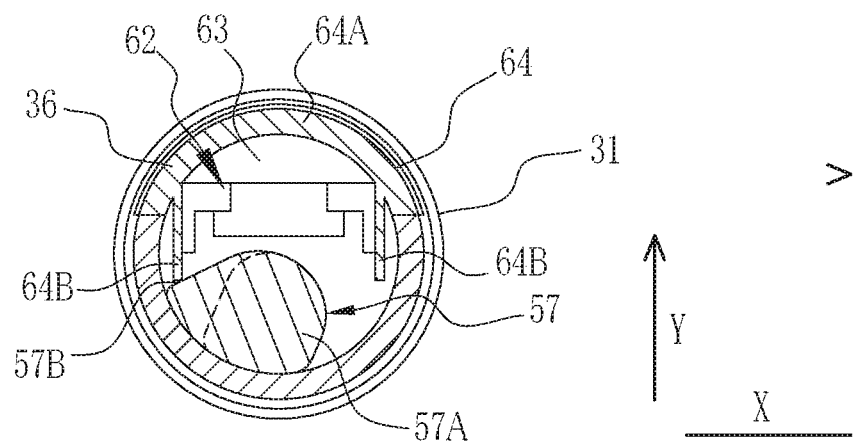

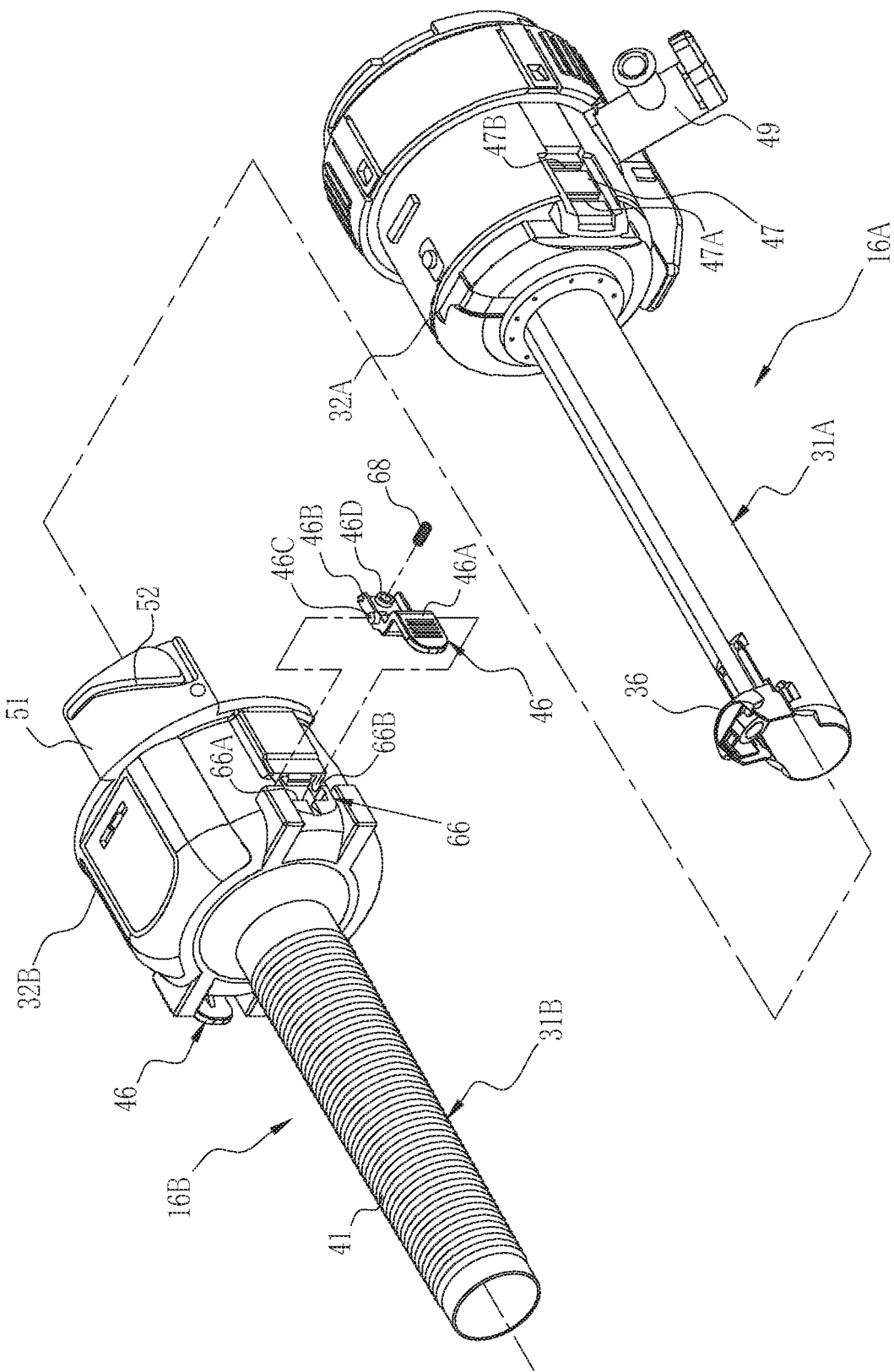

BODY CAVITY OBSERVATION SYSTEM, LAPAROSCOPE SYSTEM, TROCAR APPARATUS, AND OPERATION METHOD OF BODY CAVITY OBSERVATION SYSTEM

CROSS-REFERENCE TO RELATED APPLICATIONS

This application is a Continuation of PCT International Application No. PCT/JP2017/040482 filed on 9 Nov. 2017, which claims priority under 35 U.S.C § 119(a) to Japanese Patent Application No. 2016-220049 filed on 10 Nov. 2016. The above application is hereby expressly incorporated by reference, in its entirety, into the present application.

BACKGROUND OF THE INVENTION

1. Field of the Invention

The present application is subject to "Development of Medical Devices through Collaboration between Medicine and Industry" commissioned research of Japan Agency for Medical Research and Development, 2016 and to Industrial Technology Enhancement Act, Article 19, and relates to a body cavity observation system, a laparoscope system, a trocar apparatus, and an operation method of body cavity observation system.

2. Description of the Related Art

In the medical field, observation of the state of a body cavity is performed using an endoscope apparatus such as a laparoscope or a capsule endoscope. Such the endoscope apparatus is provided with an imaging element and other elements for imaging an observation target in the body cavity, but due to individual difference among these imaging elements, it is necessary to perform calibration such as white balance. However, since inside of body cavity is mostly reddish visceral tissue, it is necessary to insert a white reference from outside the body into the body cavity for performing white balance in the body cavity. For example, in case of using a laparoscope, it may be considered that a piece of white gauze is inserted into the body cavity from a port different from a port provided with the laparoscope and the white gauze is imaged with the laparoscope, to perform the white balance. However, such the task is very troublesome and imposes a burden on a user.

Therefore, for performing observation with the endoscope apparatus, a white chart is imaged and white balance is performed based on the obtained image, before the endoscope apparatus is inserted in the body cavity. For example, in case of a laparoscope, a distal end of the laparoscope is inserted into a device provided with a reference material of white balance to perform white balance, as in JP5266065B2 (corresponding to US2008/161646A1). In case of a capsule endoscope, the entire capsule endoscope is placed in a device provided with an image quality adjustment sheet corresponding to a white chart to perform white balance, as in JP2009-195558A.

SUMMARY OF THE INVENTION

In an endoscopic operation using a laparoscope, a field of view of a target site to be treated is provided exclusively by a laparoscopic image. Therefore, the field of view is remarkably restricted as compared with an abdominal operation capable of observing the target site to be treated with naked eyes. In such the endoscopic operation, in order to perform appropriate procedures, it has been required to eliminate blind spots as much as possible by providing another field of view different from the laparoscopic image.

In order to meet such the demand, a trocar apparatus with camera, which has a camera at the distal end of a trocar for inserting a treatment tool such as a forceps, an electronic knife, a stapler or so on, has been proposed (JP2016-016053A). According to the trocar apparatus with camera, since a new body cavity image different from the laparoscopic image can be obtained, it is possible to widen the field of view. The trocar apparatus with camera is a retractable type to displace between a storage position where a camera is stored in a pipe section having an insertion of a treatment tool and a deployed position where the camera is popped up in a direction projecting from the outer peripheral surface of the pipe portion. The camera is displaced to the storage position for inserting/extracting the trocar device into/from the body cavity, and is displaced to the deployed position for observing inside the body cavity.

The trocar apparatus with camera is sealed with a package or the like to prevent attachment of germs and so on until immediately before use. At the time of starting to use, the trocar apparatus with camera is opened from the package. As for the trocar apparatus with camera, as described above, it is necessary to perform white balance. However, from the viewpoint of avoiding attachment of germs and so on, it is preferable that the trocar device is inserted into the body cavity right after taken out from the package, and white balance is performed in the body cavity.

An object of the present application is to provide a body cavity observation system, a laparoscope system, a trocar apparatus, and an operation method of body cavity observation system, which are capable of performing white balance in a body cavity.

A body cavity observation system of the present application comprises a trocar with camera including a trocar having a pipe section that is insertable into a body cavity, a trocar shaft attached to the trocar when the trocar is inserted into the body cavity, the trocar shaft having a white part formed on a surface of a puncture member at a distal end of the trocar shaft, the puncture member that is exposed from a distal end of the pipe section, a camera section disposed in a distal end area of the pipe section, the camera section obtaining a trocar image, that includes an image of the white part, by performing imaging when the puncture member of the trocar shaft is exposed, and a white balance setting section, which sets a white balance for subsequent trocar images based on the image of the white part in the trocar image. It is preferable that the camera section is displaceable between a storage position where the camera section is stored in the pipe section and a deployed position where the camera section is deployed in a direction projecting from the outer peripheral surface of the pipe section, and the camera section performs imaging at the deployed position.

A laparoscope system of the present application comprises the body cavity observation system, and an endoscope inserted in a trocar different from the trocar of the body cavity observation system. The white part formed on the surface of the puncture member is illuminated with illumination light from the endoscope. It is preferable that the white balance for the trocar image is substantially the same as a white balance for an endoscopic image obtained by the endoscope.

A trocar apparatus of the present application is used for setting a white balance of a trocar image obtained inside a body cavity, the trocar apparatus comprising a trocar having a pipe section that is insertable into the body cavity, and a trocar shaft attached to the trocar when the trocar is inserted into the body cavity, the trocar shaft having a white part formed on a surface of a puncture member at a distal end of the trocar shaft, and the puncture member that is exposed from a distal end of the pipe section. The trocar image includes an image of the white part, that is used by a white balance setting section to set the white balance of subsequent trocar images.

It is preferable to provide a camera section disposed in a distal end area of the pipe section, to obtain the trocar image including the image of the white part by performing imaging when the puncture member of the trocar shaft is exposed. It is preferable that the camera section is displaceable between a storage position where the camera section is stored in the pipe section and a deployed position where the camera section is deployed in a direction projecting from the outer peripheral surface of the pipe section, and the camera section performs imaging at the deployed position. It is preferable that the white balance setting section is provided in a processor connected to the trocar.

An operation method of a body cavity observation system of the present application is for the body cavity observation system includes a trocar with camera including a trocar having a pipe section that is insertable into a body cavity, a trocar shaft attached to the trocar when the trocar is inserted into the body cavity, and a camera section disposed in a distal end area of the pipe section. The operation method comprising obtaining a trocar image, that includes an image of a white part, by the camera section performing imaging when a puncture member of the trocar shaft is exposed, the white part formed on a surface of the puncture member at a distal end of the trocar shaft, the puncture member exposed from a distal end of the pipe section, and setting a white balance for subsequent trocar images, by a white balance setting section, based on the image of the white part in the trocar image.

It is preferable that the operation method further comprising displacing the camera section between a storage position where the camera section is stored in the pipe section and a deployed position where the camera section is deployed in a direction projecting from the outer peripheral surface of the pipe section, and the camera section performs imaging at the deployed position.

According to the present application, a white balance can be performed in a body cavity.

BRIEF DESCRIPTION OF THE DRAWINGS

FIG. 15A is an explanatory view of a deployment assist mechanism in a state where the trocar shaft is in an initial position.

FIG. 15B is an explanatory view of the deployment assist mechanism in a state where the trocar shaft starts contacting with the camera section.

FIG. 17 is an exploded perspective view showing an outer cylinder locking mechanism.

DESCRIPTION OF THE PREFERRED EMBODIMENTS

First Embodiment

[Overall Configuration of Laparoscope System]

Figure 1:
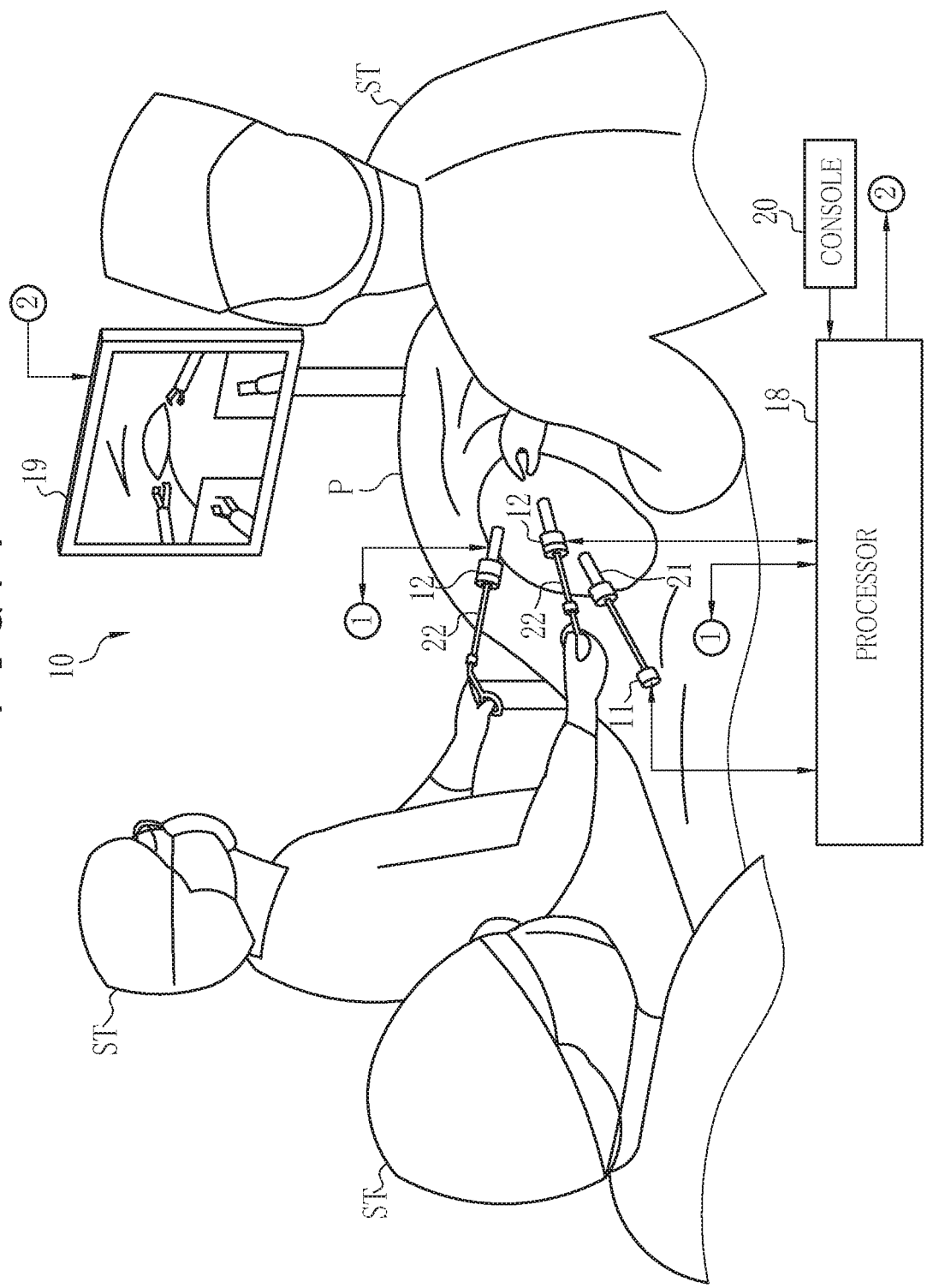
FIG. 1 is a schematic diagram of a laparoscopic system.

As shown in FIG. 1, a laparoscopic system 10, which is an example of a body cavity observation system, is used by medical staff ST including a doctor to observe inside a body cavity (more specifically intraperitoneal cavity) during laparoscopic operation. The laparoscopic system 10 includes an endoscope system and a trocar apparatus with camera 12. The endoscope system includes an endoscope 11, a processor 18, a monitor 19, and a console 20. The trocar apparatus with camera 12 is constituted of a trocar with camera 16 and a trocar shaft 17 (see FIG. 5).

The trocar with camera 16 is a trocar which is an insertion tool used as an insertion port for inserting a treatment tool 22 such as a forceps into a body cavity and has a camera function added to the trocar.

The processor 18 executes image processing on an endoscopic image of an abdominal cavity imaged by the endoscope 11 and a trocar image of the abdominal cavity imaged by the camera of the trocar with camera 16. The processor 18 has an image compositing function of compositing the endoscopic image and each of the trocar images. As shown in FIG. 1, on the monitor 19 of the processor 18, a composite image of the endoscope image and the trocar images is displayed. Through the composite image, a field of view of the abdominal cavity is provided to the medical staff ST. Instead of or in addition to displaying the composite image, the endoscopic image and the trocar image may be displayed in independent display windows.

Figure 2:
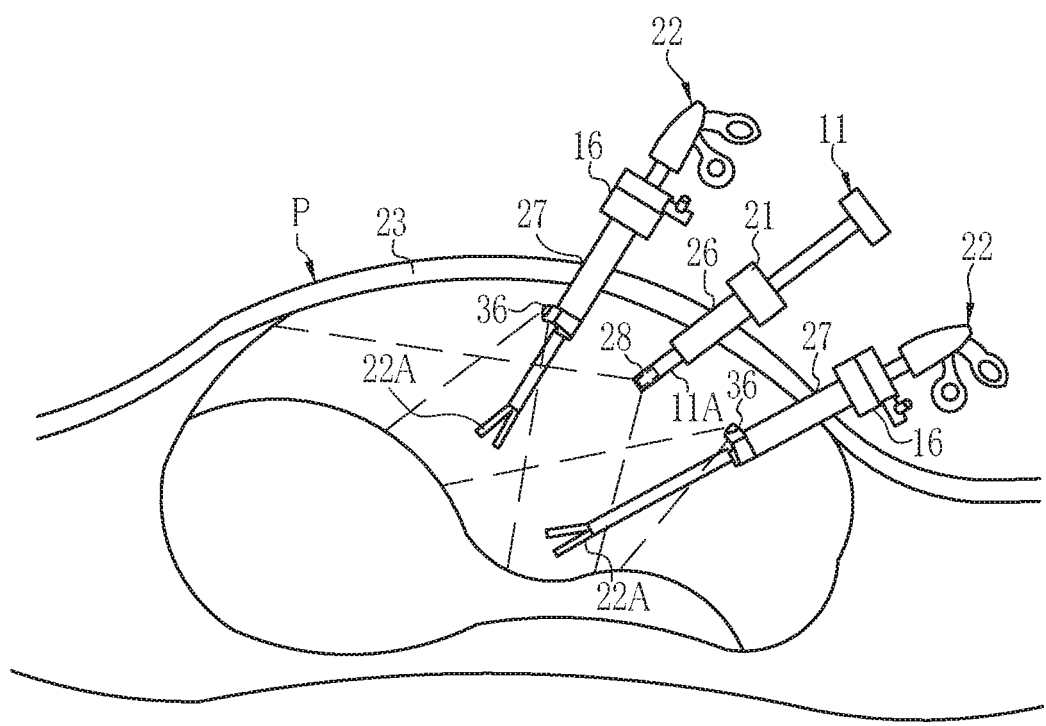
FIG. 2 is a cross-sectional view of an abdominal cavity in a state where a trocar is inserted.

As shown in FIG. 2, the endoscope 11 is inserted into the abdominal cavity of the patient P through a trocar 21. The trocar 21 (endoscope trocar) for the endoscope 11 is a normal trocar with no camera, different from the trocar with camera 16. The trocar 21 is an insertion tool used as an insertion port for inserting the endoscope 11 into the abdominal cavity. The trocar 21 has a substantially cylindrical pipe section (cannula, cannula sleeve) and a head section provided on the proximal end side of the pipe section. The head section has a larger diameter than that of the pipe section. The pipe section of the trocar 21 is provided with an insertion hole penetrating inside the pipe section in the axial direction, and the endoscope 11 is inserted through the insertion hole.

In laparoscopic surgery, for inserting each trocar 21, 16 into the abdominal cavity, skin of an abdominal wall 23 of the patient P is incised with a scalpel to form incision parts 26, 27. The abdominal wall 23 is formed of skin, subcutaneous tissue such as fat 23A (see FIGS. 24A and 24B), and muscle tissue. In this embodiment, in order to use the total of three trocars, one trocar 21 for the endoscope 11 and two trocars with camera 16, the number of incision parts 26, 27 is three in total, one incision part 26 for the endoscope 11 and two incision parts 27 for the treatment tools 22. As for the positions of the three incision parts 26, 27, for example, the incision part 26 for the endoscope 11 is provided at the center, and the incision parts 27 for the treatment tools 22 are provided on the left and right from the incision part 26. The number and position of the incision parts 26 and 27 in this embodiment are merely an example, and may be appropriately determined depending on the target site of the operation, the number of the treatment tools to be used, and so on.

The trocar 21 is inserted into the incision part 26 and fixed to the abdominal wall 23. The trocar with camera 16 is inserted into each of the two incision parts 27 and fixed to the abdominal wall 23. Accordingly, the trocar 21 can be used as an insertion port for the endoscope 11, and the trocar with camera 16 can be used as an insertion port for the treatment tool 22.

The endoscope 11 has an illumination function of emitting illumination light for illuminating the entire body cavity and an imaging function of imaging a target region in the body cavity. On the other hand, the trocar with camera 16 does not have the illumination function and has only the imaging function. Use of such the trocar with camera 16 can avoid an occurrence of flare due to extra light hitting the body cavity depending on the positional relationship between the trocar with camera 16 and the endoscope 11. Therefore, a camera section 36 of the trocar with camera 16 takes an image of the subject illuminated with the illumination light from the endoscope 11. Since the camera section 36 performs imaging using the illumination light from the endoscope 11, it is necessary to perform white balance for trocar images while the illumination light from the endoscope 11 is illuminated. Details of the white balance for trocar images will be described later.

As shown in the screen of the monitor 19 in FIG. 1, the endoscope 11 inserted in the central trocar 21 provides a field of view overlooking the entire treatment target area in the abdominal cavity. In addition, the trocars with camera 16 positioned on both sides of the endoscope 11A provides a field of view around the distal end 22A of the treatment tool 22.

As shown in FIG. 2, during laparoscopic surgery, a pneumoperitoneum procedure is performed in which carbon dioxide gas is injected into the abdominal cavity to expand the abdominal cavity. The pneumoperitoneum procedure secures a space for treatment in the abdominal cavity. A connection port to which an air feed pipe of a gas supply device (not shown) is connected is provided to the normal trocar 21 and the trocar with camera 16 (see FIG. 3 and FIG. 4 for a connection port 49 of the trocar with camera 16). Carbon dioxide gas supplied from the gas supply device is injected into the abdominal cavity through the trocar 21 and the trocar with camera 16.

As described above, since the pneumoperitoneum procedure is performed in the laparoscopic surgery, the trocar 21 and the trocar with camera 16 have an airtight structure for airtightly sealing the insertion hole in order to prevent gas leakage from inside to outside of the body cavity through the respective insertion holes. The airtight structure of the trocar with camera 16 will be described in detail later.

[Schematic Configuration of Endoscope]

As shown in FIG. 2, the endoscope 11 is, for example, a rigid endoscope in which an insertion portion 11 is formed of a hard material such as a metal. At the distal end of the insertion portion 11A, there are provided an illumination window for illuminating a subject (internal organs and so on) in the abdominal cavity with illumination light and a camera unit 28 for imaging the subject by receiving the reflected light from the subject. As well known, the camera unit 28 includes an imaging device (not shown) such as a CCD (Charge-Coupled Device) image sensor and a CMOS (Complementary Metal-Oxide-Semiconductor) for photoelectrically converting the received light, and an imaging lens (not shown) for forming an optical image of the subject on the imaging surface of the imaging device.

The imaging device is, for example, a color imaging device, and outputs a captured image as three color image signals of an R (Red) image signal, a G (Green) image signal, and a B (Blue) image signal. The imaging device is capable of capturing moving image and outputs image signals at a predetermined frame rate. Image signals are sequentially output to the processor 18 via a signal line.

In the insertion section 11A, the signal line, a light guide and so on are provided. The light guide guides the illumination light supplied from a light source device (not shown) to the illumination window. At the proximal end portion of the endoscope 11, provided is one end of a universal cable (not shown) for arranging the signal line and the light guide inside. On the other end of the universal cable, provided are a connector for connecting the light guide to the light source device and a connector for connecting the signal line to the processor 18. The endoscope 11 is connected to the light source device and the processor 18 via the universal cable.

[Overall Structure of Trocar with Camera]

As shown in FIGS. 3 to 7, the trocar apparatus with camera 12 is consisted of the trocar with camera 16 and the trocar shaft (obturator) 17. The trocar shaft 17 is detachably attached to the trocar with camera 16. The trocar with camera 16 has a cylindrical pipe section 31 and a head section 32 provided at the proximal end of the pipe section 31. The head section 32 has a substantially cylindrical shape larger in diameter than the pipe section 31. The trocar with camera 16 is provided with an insertion hole 33 penetrating inside the pipe section 31 in the axial direction (Z-axis direction), and through which the treatment tool 22 and so on are inserted.

[Schematic Configuration of Trocar with Camera]

Figure 6:
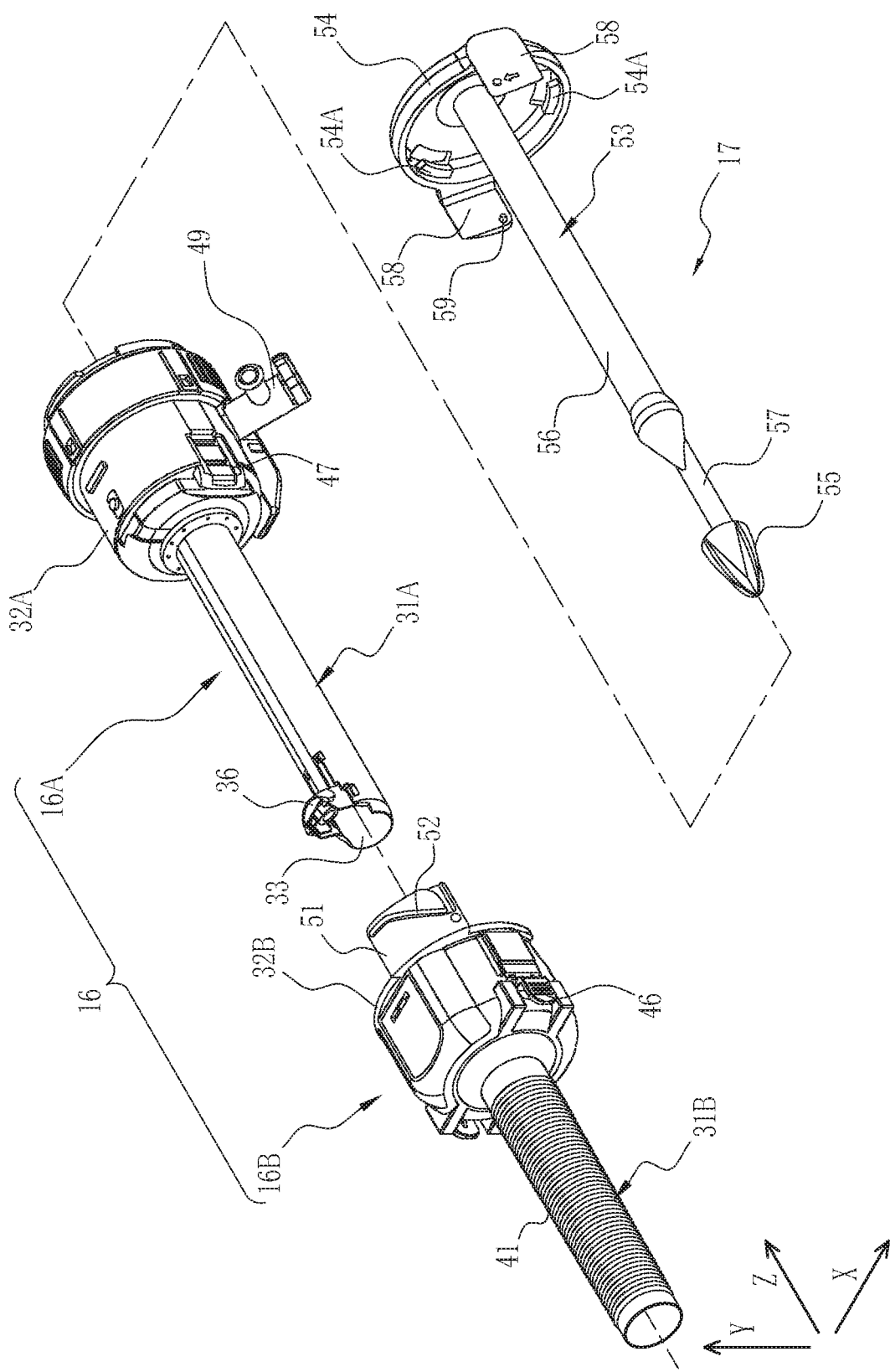
FIG. 6 is an exploded perspective view of the trocar with camera in a state where it is disassembled into an inner cylinder member and an outer cylinder member.

As shown in FIG. 6, the main part of the trocar with camera 16 is composed of an inner cylinder member 16A and an outer cylinder member 16B, and has a double structure in which most of the inner cylinder member 16A is enclosed in the outer cylinder member 16B. The inner cylinder member 16A includes a pipe section inner sleeve 31A and a head section inner sleeve 32A provided on the proximal side of the pipe section inner sleeve 31A. The pipe section inner sleeve 31A and the head section inner sleeve 32A are made of, for example, resin, and the both are formed integrally. The outer cylinder member 16B includes a pipe section outer sleeve 31B and a head section outer sleeve 32B provided on the proximal side of the pipe section outer sleeve 31B. In this embodiment, the pipe section outer sleeve 31B and the head section outer sleeve 32B are made of resin, for example, and the both are formed integrally.

A retractable camera section 36 is provided in the distal end area of the pipe section inner sleeve 31A. The camera section 36 is displaceable between a storage position shown in FIG. 3, where the camera section 36 is stored inside the pipe section inner sleeve 31A, and a deployed position shown in FIG. 4, where the camera section 36 is deployed by popping up in a direction protruding from the outer peripheral surface of the pipe section inner sleeve 31A. The inner cylinder member 16A and the outer cylinder member 16B are provided so as to be relatively slidable along the axial direction (Z-axis direction). As will be described later, the deployment and storage of the camera section 36 is performed by sliding the pipe section outer tube 31B with respect to the pipe section inner sleeve 31A.

A slip resistance 41 is formed on the outer peripheral surface of the pipe section outer sleeve 31B. The slip resistance 41 is for fixing the pipe section 31 to the abdominal wall 23 at a desired insertion position. The slip resistance 41 is configured in such a manner that a plurality of irregularities formed in the circumferential direction around the Z-axis are arranged in the Z-axis direction on the outer peripheral surface of the pipe section outer sleeve 31B. The slip resistance 41 has a coefficient of friction higher than that of the portion having no irregularities. The slip resistance 41 is formed over substantially the entire length in the Z-axis direction of the pipe section outer sleeve 31B. Therefore, the slip resistance 41 and the abdominal wall 23 can be engaged at any position in the Z-axis direction of the pipe section outer sleeve 31B. By this engagement, the pipe section outer sleeve 31B can be fixed to the abdominal wall 23 at a desired insertion depth.

Figure 7:
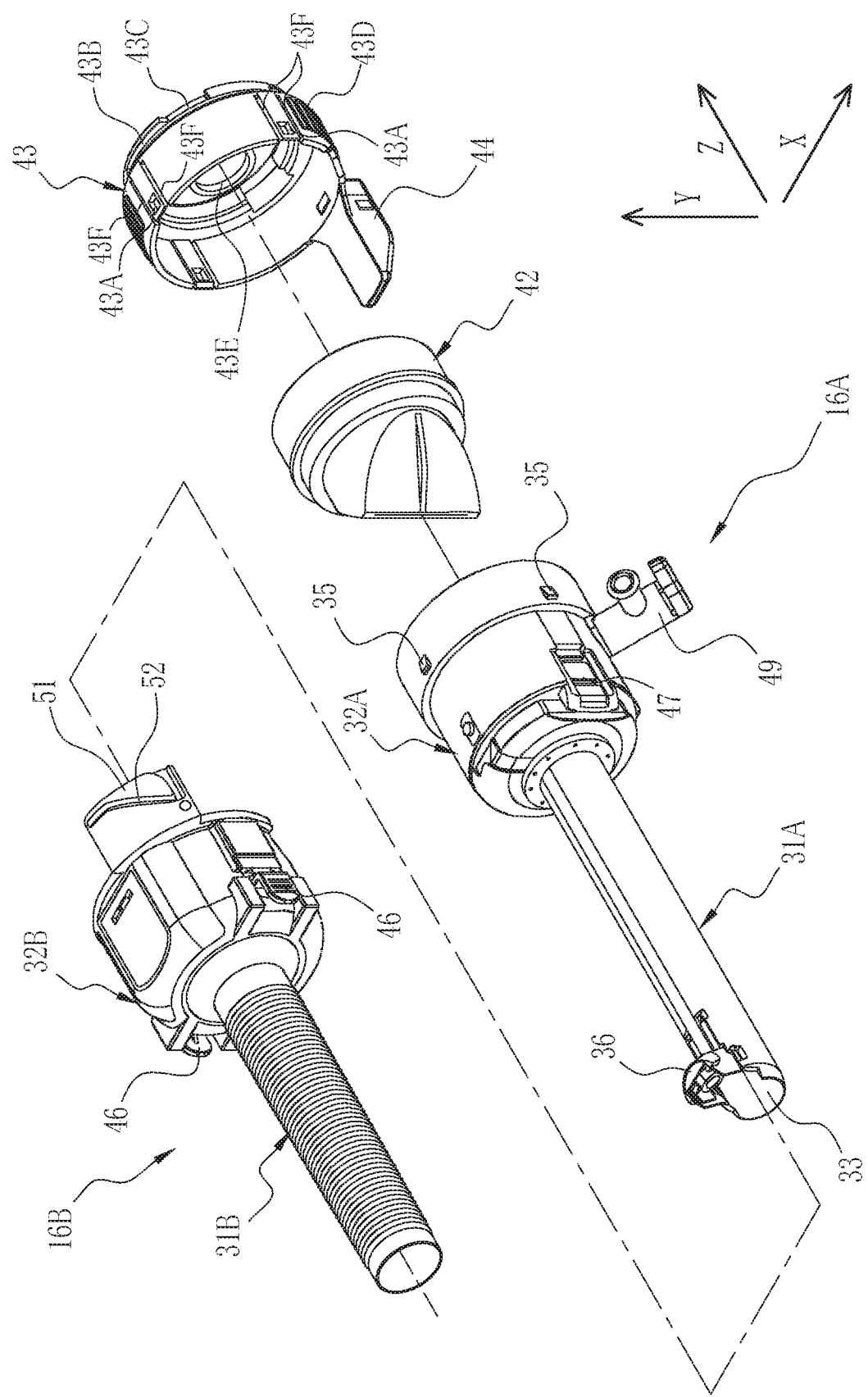
FIG. 7 is an exploded perspective view of the trocar with camera.

As shown in FIGS. 6 and 7, the main portion of the head section 32 is composed of the head section inner sleeve 32A and the head section outer sleeve 32B. As shown in FIG. 7, the trocar with camera 16 incorporates an airtight structure unit 42, and the airtight structure unit 42 is accommodated in the head section inner sleeve 32A. On the proximal end portion of the head section inner sleeve 32A, a rear cover 43 covering the opening portion on the proximal side is attached. Further, the head section inner sleeve 32A is provided with the connection port 49 (see also FIG. 3 and FIG. 4) to which the gas supply device is connected. As described above, the carbon dioxide gas is injected into the abdominal cavity through the connection port 49, and the pneumoperitoneum treatment is performed. The airtight structure unit 42 has a function of preventing gas leakage from the abdominal cavity to the outside of the body.

In addition, the head section 32 is provided with a connector member 44. The connector member 44 is a connector for connecting a communication cable (not shown) for electrically connecting to the processor 18. The connector member 44 is provided in the rear cover 43, and is disposed at a position facing the outer peripheral surface of the head section 32 in a state where the rear cover 43 is attached to the head section inner sleeve 32A. The connector member 44 is electrically connected to the camera section 36 via a flexible cable (not shown) disposed in a gap between the inner cylinder member 16A and the outer cylinder member 16B. The connector member 44 relays the image signal from the camera section 36 to the processor 18 and relays the control signal from the processor 18 to the camera section 36.

On the rear surface of the rear cover 43, an opening 43E for inserting the trocar shaft 17 and the treatment tool 22 is formed. Further, on the outer peripheral surface of the rear cover 43 in the circumferential direction around the Z-axis, a grip section 43D is formed with a plurality of irregularities. The grip section 43D functions as a slip resistance for gripping and operating the head section inner sleeve 32A.

Also, on the outer peripheral surface of the rear cover 43, four engagement holes 43A are formed at intervals of about 90° in the circumferential direction. On the outer peripheral surface of the head section inner sleeve 32A, engagement claws 35 are formed to engage with each engagement hole 43A. The rear cover 43 is attached to the head section inner sleeve 32A by engagement of the engagement hole 43A and the engagement claw 35.

Slots 43F, which are grooves extending in the Z-axis direction, are formed on both sides of each engagement hole 43A. Accordingly, the portion of the rear cover 43 where the engagement hole 43A is formed can be elastically deformed. When the engagement hole 43A and the engagement claw 35 engage with each other, the portion where the engagement hole 43A is formed elastically deforms radially outward so as to ride on the engagement claw 35. By forming the slot 43F, engagement of the engagement hole 43A with the engagement claw 35 is facilitated.

Figure 3:
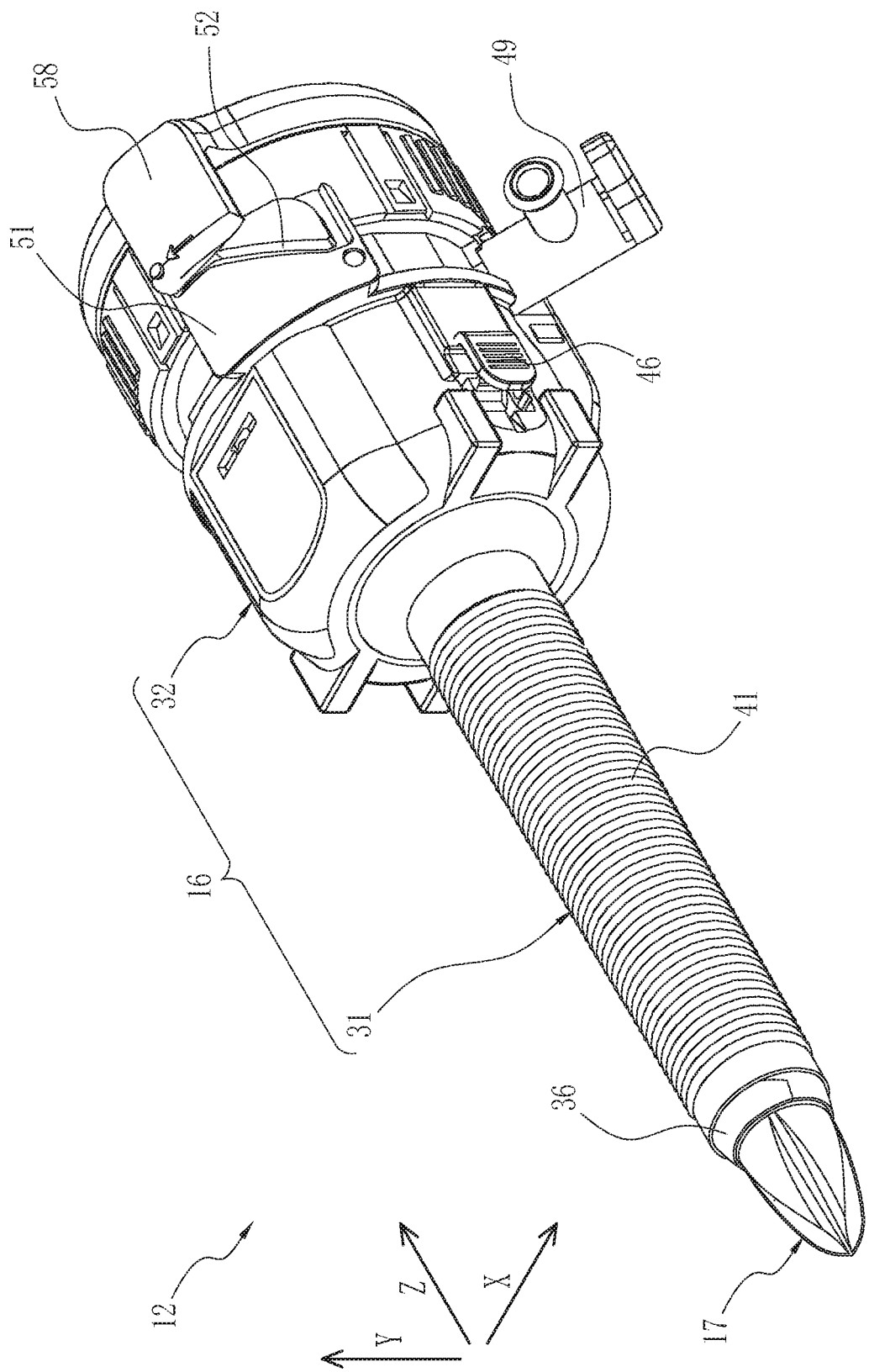
FIG. 3 is an external perspective view of a trocar apparatus with camera in a state where a camera section is stored.
Figure 4:
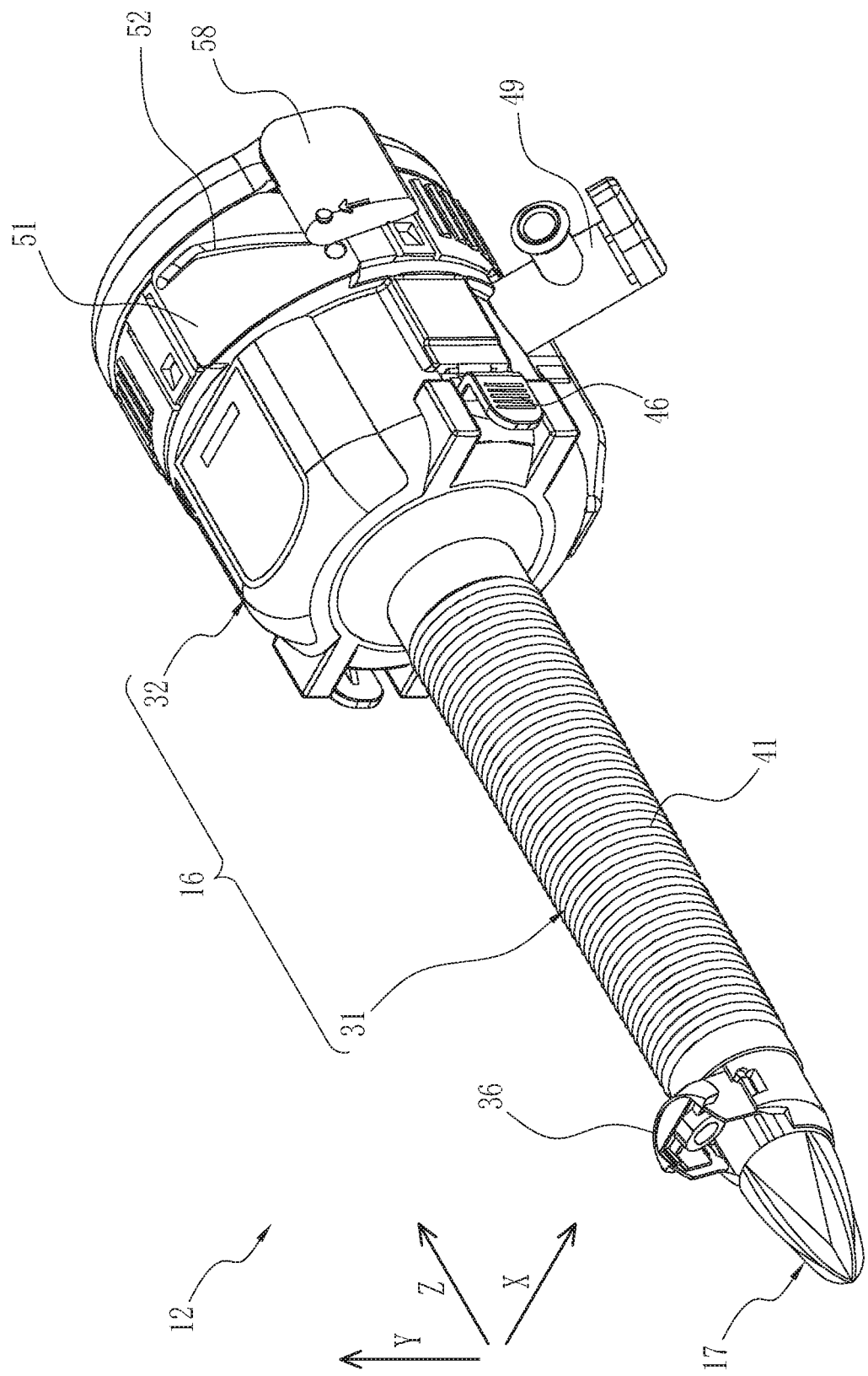
FIG. 4 is an external perspective view of the trocar apparatus with camera in a state where the camera section is deployed.

At the proximal end portion of the rear cover 43, a fitting groove 43B extending in a circular arc shape in the circumferential direction is formed. The fitting groove 43B is engaged with an engaging claw 54A (see FIG. 6) provided on a handle member 54 of the trocar shaft 17. By the engagement between the fitting groove 43B and the engaging claw 54A, the trocar shaft 17 is attached to the head section inner sleeve 32A as shown in FIGS. 3 and 4.

As shown in FIGS. 6 and 7, a cutout 43C is formed in a part of the fitting groove 43B. The engaging claw 54A and fitting groove 43B are fitted by inserting the engaging claw 54A from the cutout 43C into the fitting groove 43B, and rotating the handle member 54 around the axis from the inserted position. The fitting completion position corresponds to an initial position (see FIGS. 12A, 13A, and 3) of the trocar shaft 17 described later.

On the outer peripheral surface of the head section outer sleeve 32B, a lock releasing member 46 is arranged. The lock releasing member 46 is an operation section for releasing an outer cylinder locking mechanism which locks the slide of the outer cylinder member 16B with respect to the inner cylinder member 16A. As described later, the lock releasing member 46 is a component of the outer cylinder locking mechanism, together with an engaging member 47 provided on the outer peripheral surface of the head section inner sleeve 32A. The engaging members 47 are provided on the outer peripheral surface of the head section inner sleeve 32A, and are arranged at two positions opposite to each other in the circumferential direction about the axis of the outer peripheral surface, that is, two positions at about 180° intervals in the circumferential direction.

The lock releasing members 46 are disposed at positions facing the two engaging members 47 in the circumferential direction about the Z-axis of the head section outer sleeve 32B. The unlocking operation is performed by simultaneously operating two lock releasing members 46 disposed opposite to each other with holding them by hand. Upon the unlocking operation, the outer cylinder member 16B becomes slidable relative to the inner cylinder member 16A.

In addition, the head section outer sleeve 32B is provided with a cam plate 51 extending rearward from the proximal end. A cam groove 52 is formed on the outer peripheral surface of the cam plate 51. The cam plate 51 is arranged at two opposing positions in the circumferential direction of the head section outer sleeve 32B, that is, at intervals of about 180° in the circumferential direction. The cam plate 51 engages with the handle member 54 (see FIG. 6) of the trocar shaft 17 to change the rotation movement around the axis of the trocar shaft 17 to the slide movement in the direction of the Z-axis of the outer cylinder member 16B. As will be described in detail later, the rotation of the trocar shaft 17 causes the head section outer sleeve 32B to slide so that the deployment and storing of the camera section 36 are performed.

[Schematic Configuration of Trocar Shaft]

Figure 5:
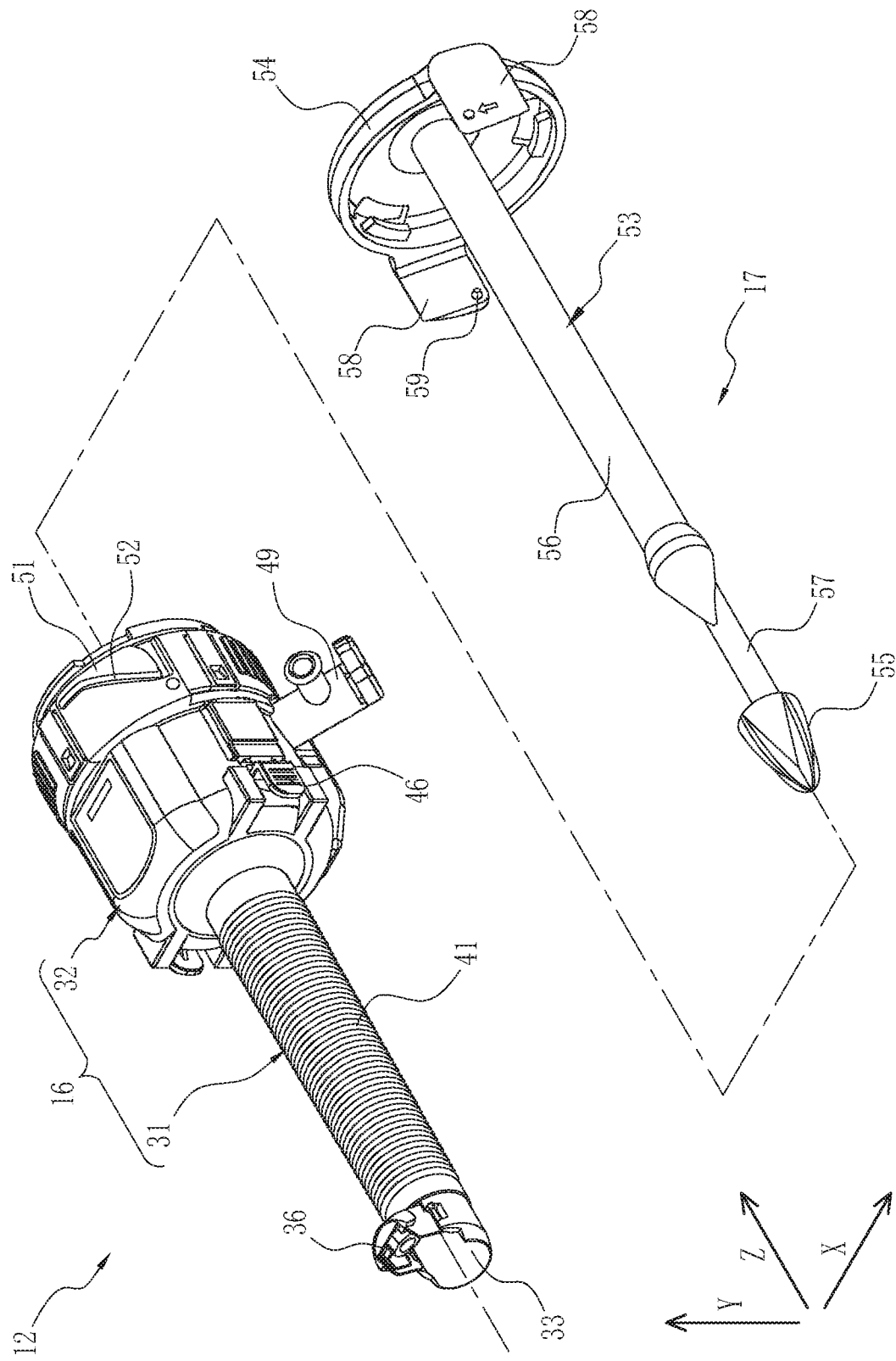
FIG. 5 is an exploded perspective view of a trocar with camera in a state where a trocar shaft is removed.

As shown in FIGS. 3 and 4, the trocar shaft 17 is attached to the trocar with camera 16 for inserting the pipe section 31 into the body cavity. In FIG. 5 showing a state where the trocar shaft 17 is pulled out from the trocar with camera 16, the trocar shaft 17 has a shaft member 53 and a handle member 54 which is provided at the proximal end of the shaft member 53 and has a diameter larger than that of the shaft member 53. A puncture member 55 is provided at the distal end of the shaft member 53. In a state where the trocar shaft 17 is attached to the trocar with camera 16, the shaft member 53 is inserted into the insertion hole 33 of the pipe section 31. In this state, as shown in FIG. 3, the shaft member 53 passes through the insertion hole 33, and the puncture member 55 protrudes from the distal end of the pipe section 31 and is exposed to the outside.

As shown in FIG. 3, the puncture member 55 has a tapered shape in which the outer diameter around the Z-axis is the smallest at the distal end and gradually increases toward the proximal end side. In this embodiment, the puncture member 55 has a cannonball shape in which an outline indicating the outer peripheral surface is a curved line in a longitudinal cross section (Y-Z cross section) cut along the Z-axis direction. Note that the shape of the puncture member 55 may be conical in which the outline indicating the outer peripheral surface is a straight line in the longitudinal cross section. When the trocar with camera 16 is inserted into the body cavity, the incision part 27 (see FIG. 2) is punctured from the puncture member 55. Then, the incision part 27 is pushed and spread by the puncture member 55, and the pipe section 31 at the rear of the puncture member 55 is inserted into the incision part 27 which is pushed out.

As shown in FIG. 5, the shaft member 53 has the puncture member 55, a shaft member body 56, and a connecting member 57. The connecting member 57 connects the puncture member 55 and the shaft member body 56. Between the puncture member 55 and the shaft member body 56, the maximum diameter is approximately equal and the cross-sectional area of the cross section (X-Y cross section) orthogonal to the Z-axis direction is also approximately equal. On the other hand, in the cross section (X-Y cross section) of the shaft member 53, the cross sectional area of the connecting member 57 is smaller than the cross sectional area of the puncture member 55 and the shaft member body 56. The connecting member 57 is disposed offset from the central axis of the shaft member 53. Specifically, the connecting member 57 is offset in a direction away from the storage position of the camera section 36.

In a state in which the trocar shaft 17 is attached, the camera section 36 is positioned behind the puncture member 55. When inserting the pipe section 31 into the body cavity, the camera section 36 is stored in the pipe section 31. The connecting member 57 is provided to secure a space for storing the camera section 36 behind the puncture member 55, in a state where the trocar shaft 17 is attached to the trocar with camera 16.

The handle member 54 is gripped when the trocar shaft 17 is attached to or removed from the trocar with camera 16, or rotated in the inserted state. On the outer peripheral surface of the handle member 54, two pin arrangement plates 58 are provided. The pin arrangement plate 58 extends to the distal end side where the puncture member 55 is provided, and a cam pin 59 engaging with the cam groove 52 of the head section outer sleeve 32B is provided on an inner peripheral surface 58C opposite to the cam plate 51. The two pin arrangement plates 58 are provided at two positions facing each other in the circumferential direction around the Z-axis of the handle member 54, that is, at two places at intervals of about 180° in the circumferential direction in accordance with the positions of the two cam plates 51.

More specifically, the two pin arrangement plates 58 are designed to have following shapes in consideration of moldability by a mold.

Figure 8:
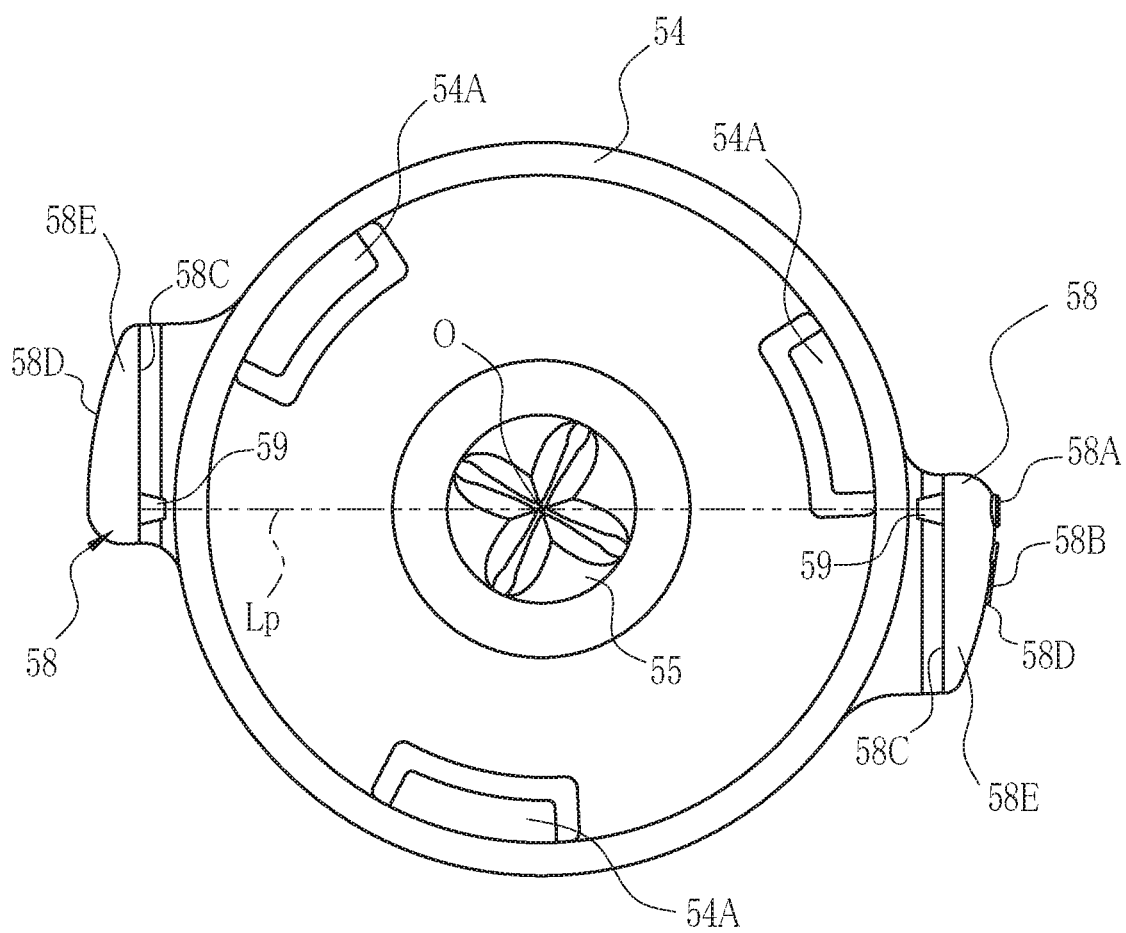
FIG. 8 is a front view of the trocar shaft.

As shown in FIG. 8, the two pin arrangement plates 58 are provided so that the cam pins 59 are arranged at intervals of 180° in the circumferential direction around the Z-axis. In the two pin arrangement plates 58, the cam pins 59 are disposed at one end side of the pin arrangement plate 58, and extension parts 58E extending in the direction orthogonal to the coupling line Lp connecting the two opposing cam pins 59 are provided. The coupling line Lp coincides with the projecting direction of the cam pin 59.

Furthermore, the extension part 58E is formed in a direction that is point-symmetrical with respect to the rotation center O of the trocar shaft 17. That is, in FIG. 8, the extension part 58E of the pin arrangement plate 58 on the right side extends downward from the position of the cam pin 59, and conversely, the extension part 58E of the pin arrangement plate 58 of left side extends upward from the position of the cam pin 59.

The cross section orthogonal to the Z-axis of the trocar shaft 17 in the pin arrangement plate 58 has a wedge shape whose thickness is large on the cam pin 59 side and decreases as the distance from the cam pin 59 increases in the extension part 58E. The inner peripheral surface 58C of the pin arrangement plate 58 is formed to be a plane extending in a direction orthogonal to the coupling line Lp of the cam pin 59. In an outer peripheral surface 58D of the pin arrangement plate 58, a part of the cross-sectional shape is formed by a curved surface having a portion overlapping with the arc shape of a circle centered on the rotation center O (for example, a concentric circle of the outer peripheral surface of the pipe section 31).

Since the pin arrangement plates 58 are formed in such a configuration and shape, moldability by a mold becomes good. For example, when using molds divided into two above and below the coupling line Lp, the extraction direction of the two molds after molding is the vertical direction orthogonal to the coupling line Lp. In this case, if the inner peripheral surface 58C of the pin arrangement plate 58 is formed as a plane extending in the direction orthogonal to the coupling line Lp, it becomes possible to extract the two molds along the vertical direction.

In addition, since the cross section of the pin arrangement plate 58 has the wedge shape whose thickness is large on the cam pin 59 side and decreases as the distance from the cam pin 59 increases in the extension part 58E, and the outer peripheral surface 58D has the part of the cross-sectional shape formed by a curved surface having a portion overlapping with the arc shape of a circle centered on the rotation center O, the shape of the cross section of the pin arrangement plate 58 becomes thinner along the mold extraction direction. Accordingly, there is no obstacle in the mold extraction. This ensures good formability of the pin arrangement plate 58.

[Camera Unit and Deployment Mechanism]

Figure 9A:
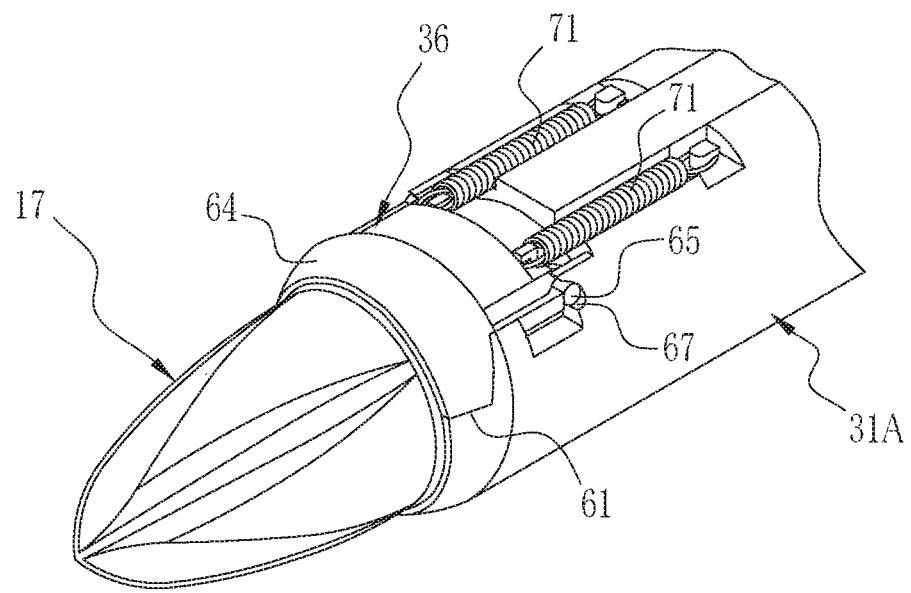
FIG. 9A is an enlarged view of a distal end portion of the trocar with camera in a state where the camera section is stored.
Figure 9B:
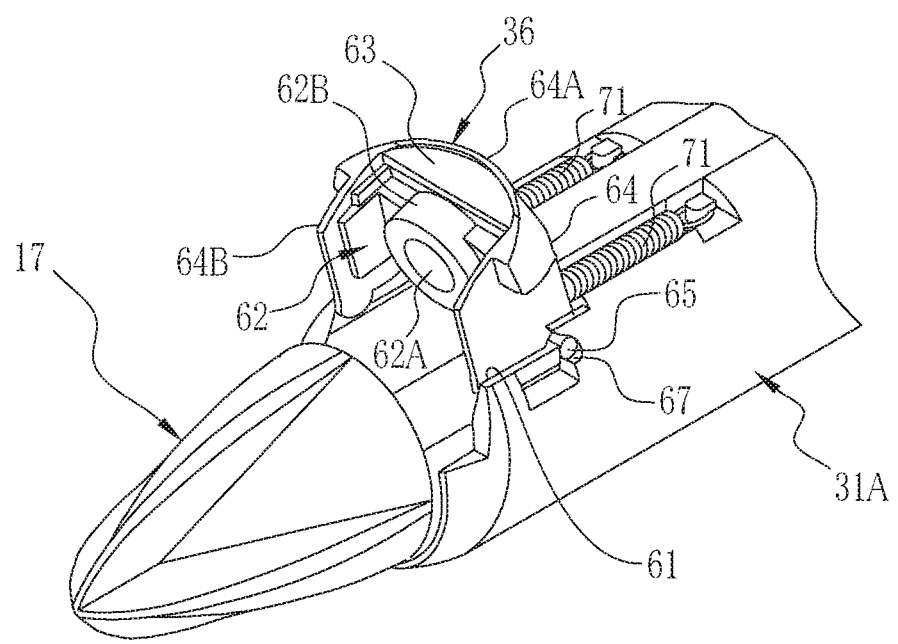
FIG. 9B is an enlarged view of the distal end portion of the trocar with camera in a state where the camera section is deployed.
Figure 10:
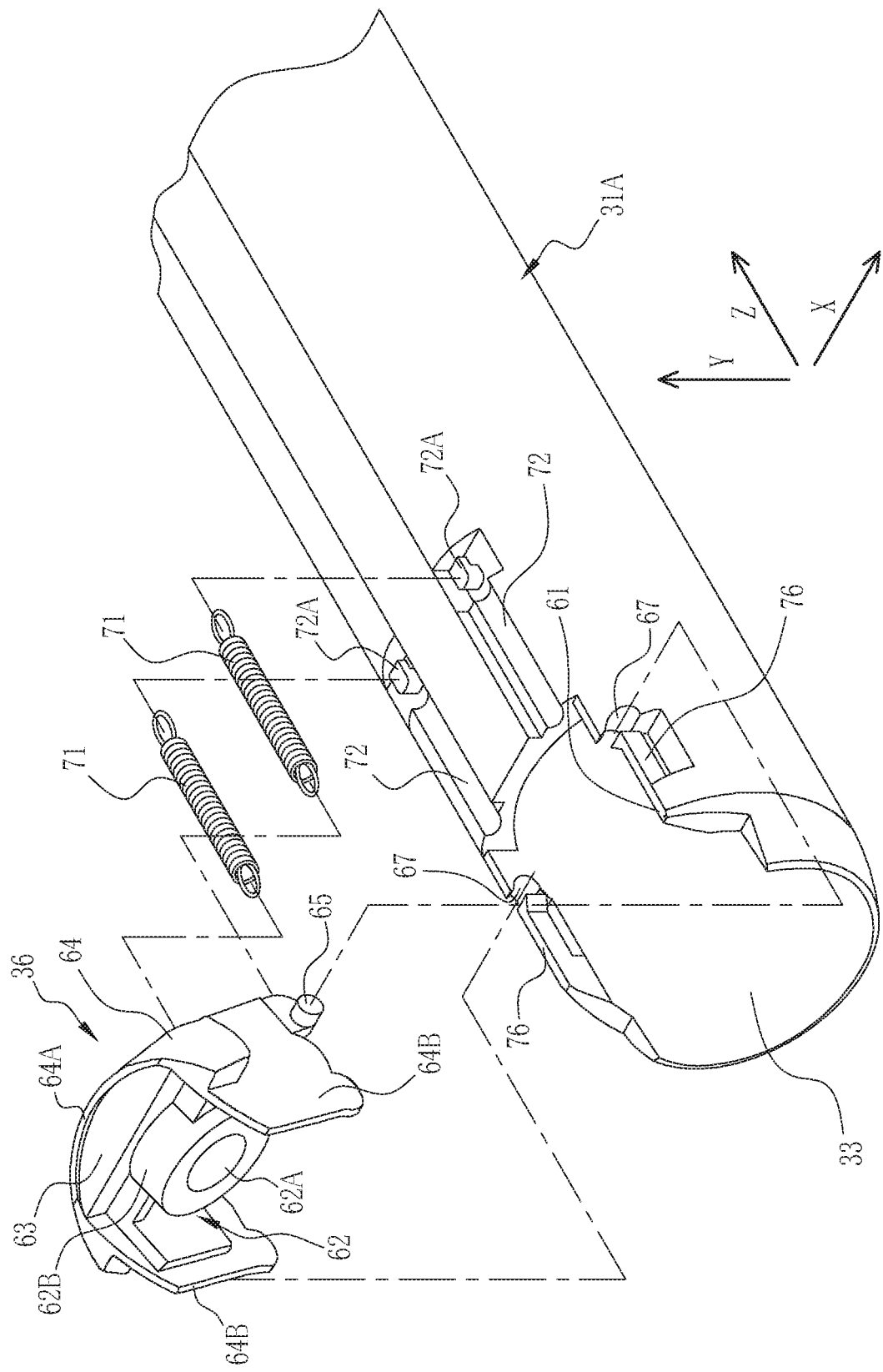
FIG. 10 is an explanatory diagram of a deployment mechanism of the camera section.

As shown in FIGS. 9A, 9B and 10, the camera section 36 is provided in a cutout 61 formed in the distal end area of the pipe section inner sleeve 31A. The camera section 36 includes a camera unit 62, a mount 63, and a housing 64. Like the camera unit 28 of the endoscope 11, the camera unit 62 includes an imaging device such as a CCD image sensor or a CMOS image sensor, and an imaging lens 62A. In addition, in the camera unit 62, illumination units (not shown) configured by light emitting elements such as LEDs (Light Emitting Diodes) may be provided on both sides of a lens barrel 62B having the imaging lens 62A.

The camera unit 62 is communicably connected to the connector member 44 provided in the head section 32 by a flexible cable (not shown). Communication of image signals output from the camera unit 62 and control signals transmitted from the processor 18 is performed between the camera unit 62 and the processor 18 via the flexible cable and the connector member 44. Though not shown, one end of the flexible cable is connected to the proximal end side of the camera section 36, the flexible cable is disposed in a gap between the pipe section inner sleeve 31A and the pipe section outer sleeve 31B, and the other end of the flexible cable extends to the connector member 44.

The camera unit 62 is attached to the housing 64 via the mount 63. Here, in case the pipe section 31 is viewed from the distal end side in the Z-axis direction, the position where the cutout 61 and the camera section 36 are disposed is defined as the upper side of the pipe section 31. The housing 64 is shaped so as to surround the upper and widthwise side ends of the camera unit 62, and has an upper face section 64A covering the upper side and a side face section 64B covering each of the two side faces.

The upper face section 64A has a shape corresponding to the shape of the cutout 61 of the pipe section 31, and the outer peripheral surface is configured with a curved surface according to the outer diameter of the pipe section 31. Accordingly, as shown in FIG. 9A, when the camera section 36 is in the storage position, the housing 64 is fitted into the cutout 61 and constitutes a part of the upper surface of the pipe section 31.

The camera section 36 is provided rotatably between the storage position and the deployed position with the proximal end side as a fulcrum. As shown in FIG. 10, a pair of right and left rotation pins 65 are provided on an outer surface of each side face section 64B located at both ends of the camera section 36. Each of the rotation pins 65 protrudes outward from each of the both ends of the camera section 36 in the width direction of the camera section 36. The rotation pins 65 constitute a rotating shaft of the camera section 36. On the proximal end side of the inner periphery of the cutout 61, bearings 67 for rotatably supporting the each rotation pin 65 are provided. Here, the rotation pins 65 provided on the each side face section 64B at the both ends of the camera section 36 and the respective bearings 67 provided on the inner periphery of the cutout 61 constitute hinge sections provided on the both ends of the camera section 36.

By the action of the hinge sections, the camera section 36 is held displaceably. Specifically, the camera section 36 rotates from the storage position shown in FIG. 9A around the rotation pin 65 on the proximal end side, and deploys as its distal end side being flipped up as shown in FIG. 9B. At the deployed position shown in FIG. 9B, the imaging lens 62A is disposed so as to face the distal end side so that the treatment tool 22 protruding from the insertion hole 33 can be imaged.

Figure 11:
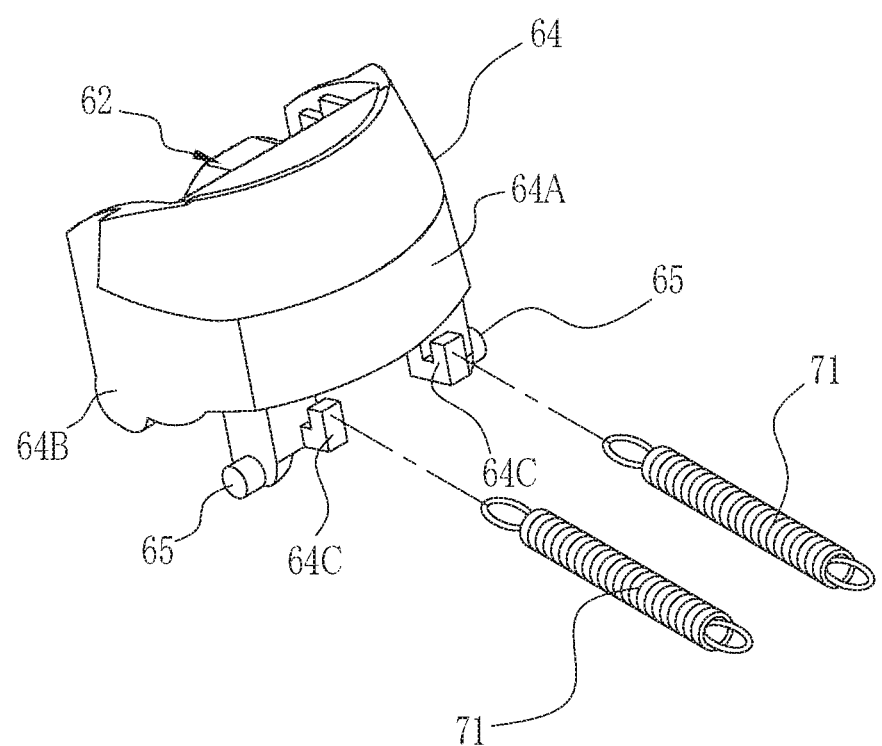
FIG. 11 is an explanatory view of the deployment mechanism viewed from the rear side of the camera section.

As shown in FIGS. 10 and 11, a spring 71 is attached to the camera section 36, and the camera section 36 is biased to the deployed position by the spring 71. The spring 71 is, for example, a coil spring, and two springs are used. The proximal end of the housing 64 is provided with a hook 64C to which one end of the spring 71 is attached. In the pipe section inner sleeve 31A, on the proximal end side of the cutout 61, two housing recesses 72 for respectively accommodating the two springs 71 are provided. The two housing recesses 72 are formed so that their longitudinal direction coincides with the Z-axis direction and are arranged in parallel. The groove of the housing recess 72 is formed in such a depth that the spring 71 does not protrude from the outer diameter of the pipe section inner sleeve 31A when the spring 71 is accommodated. This prevents interference between the spring 71 and the inner peripheral surface of the pipe section outer sleeve 31B which slides relative to the pipe section inner sleeve 31A.

Each housing recess 72 is provided with a hook 72A to which the other end of the spring 71 is attached. The spring 71 is attached respectively to the hook 64C and the hook 72A in a state where the spring 71 is extended from the natural length in which no external force is applied. Therefore, in a state where the spring 71 is attached to the hooks 64C and the hooks 72A, a biasing force is generated in the contracting direction. Since the hook 64C provided at the proximal end of the camera section 36 is located above the rotation pin 65, the hook 64C is pulled toward the proximal side by the biasing force in the contraction direction generated by the spring 71. By this pulling force, a rotational force acts on the camera section 36 with the rotation pin 65 as a fulcrum toward the deployed position, and the camera section 36 is biased toward the deployed position.

Figure 12A:
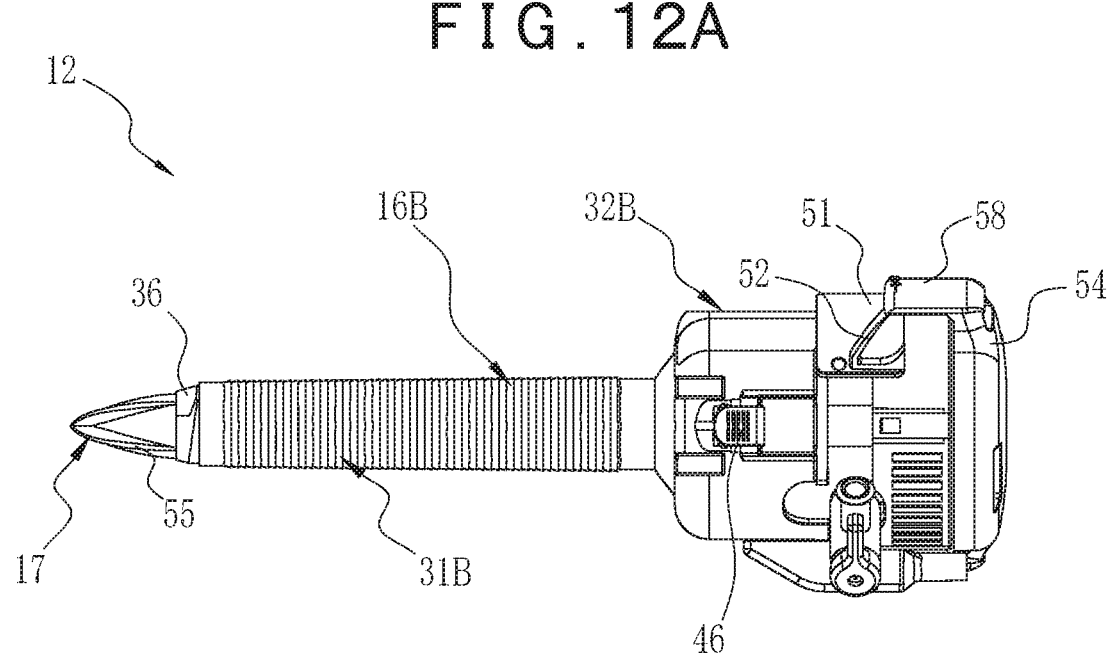
FIG. 12A is a side view of the trocar device with camera in a state where the camera section is stored.
Figure 12B:
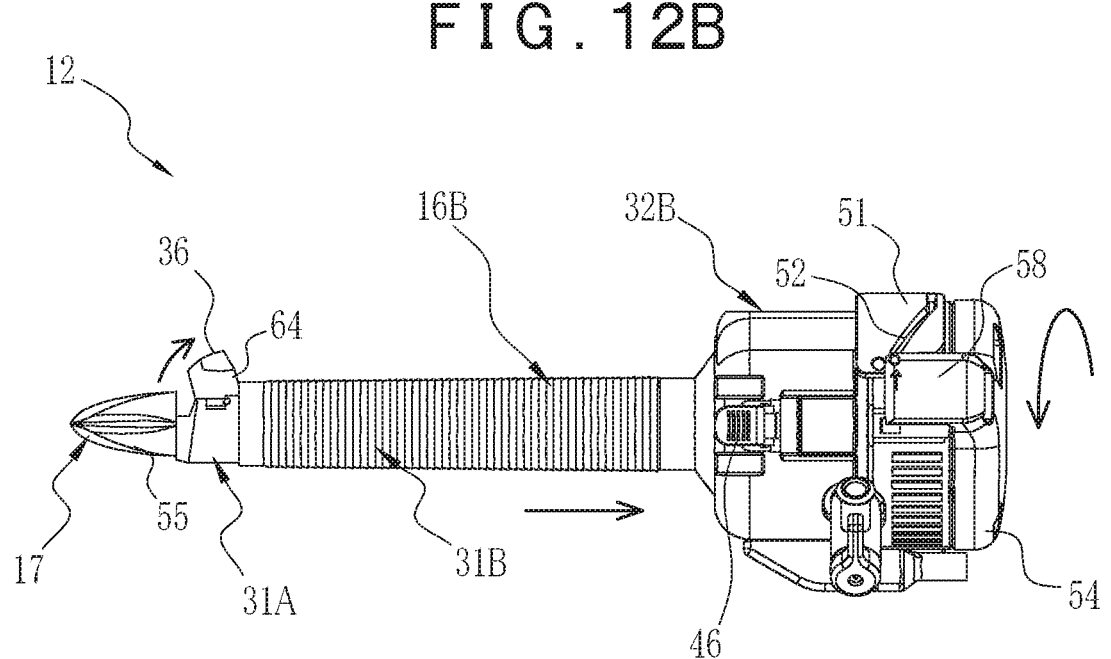
FIG. 12B is a side view of the trocar device with camera in a state where the camera section is deployed.
Figure 13A:
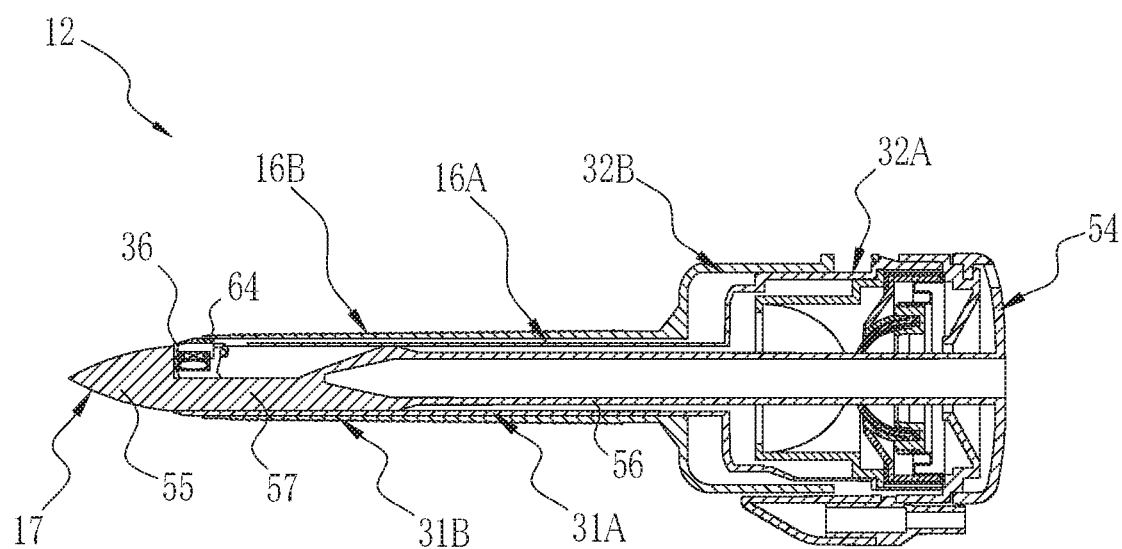
FIG. 13A is a cross-sectional view of the trocar device with camera in a state where the camera section is stored.
Figure 13B:
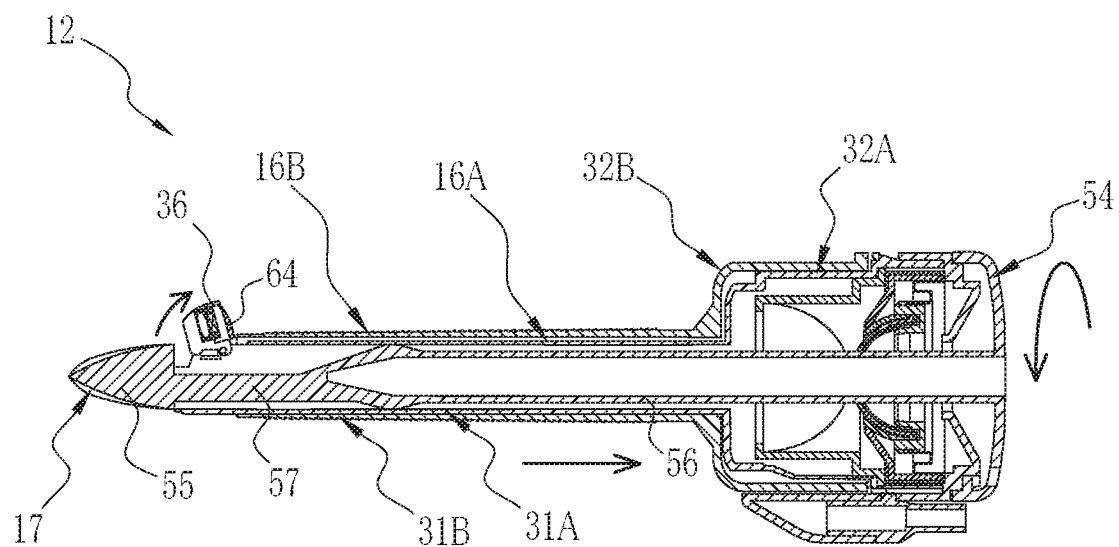
FIG. 13B is a cross-sectional view of the trocar device with camera in a state where the camera section is deployed.

As shown in FIGS. 12A and 12B and FIGS. 13A and 13B, the deployment and storage of the camera section 36 are performed by the slide operation of the pipe section outer sleeve 31B. As shown in FIGS. 12A and 13A, the pipe section outer sleeve 31B slides along the axial direction between a holding position where the camera section 36 is held at the storage position and a release position where the camera section 36 is retracted further rearward from the holding position to release the holding, as shown in FIGS. 12B and 13B.

As described above, the camera section 36 is biased by the spring 71 toward the deployed position. As shown in FIGS. 12A and 13A, in the holding position, the distal end of the pipe section outer sleeve 31B covers the rear portion of the camera section 36. Thus, the pipe section outer sleeve 31B restricts the deployment of the camera section 36 against the biasing force of the spring 71, and holds the camera section 36 at the storage position. Further, as shown in FIG. 13A, in a state where the trocar shaft 17 is attached to the trocar with camera 16, the camera section 36 is stored in the housing space formed by the connecting member 57 at the storage position.

On the other hand, when the pipe section outer sleeve 31B slides to the release position shown in FIGS. 12B and 13B, the distal end of the pipe section outer sleeve 31B retracts from the rear portion of the camera section 36. As a result, the holding of the pipe section outer sleeve 31B with respect to the camera section 36 is released. When the holding is released, the camera section 36 pops up and deploys by the bias of the spring 71.

The spring 71 and the outer cylinder member 16B constitute the deployment mechanism which releases the holding of the camera section 36 by the release operation of the outer cylinder member 16B so that the camera section 36 pops up and deploys to the deployed position.

[Operation Mechanism for Deployment and Storing Camera Section]

As shown in FIGS. 12A and 12B, the sliding operation of the pipe section outer sleeve 31B is performed by the rotation operation about the axis of the trocar shaft 17. As described above, the head section outer sleeve 32B of the outer cylinder member 16B is provided with the cam plate 51 in which the cam groove 52 is formed. The cam groove 52 engages with the cam pin 59 (see FIG. 5) provided on the trocar shaft 17. The cam groove 52 and the cam pin 59 constitute an operation mechanism for sliding the pipe section outer sleeve 31B to the proximal side by the rotation operation of the trocar shaft 17.

Figure 14:
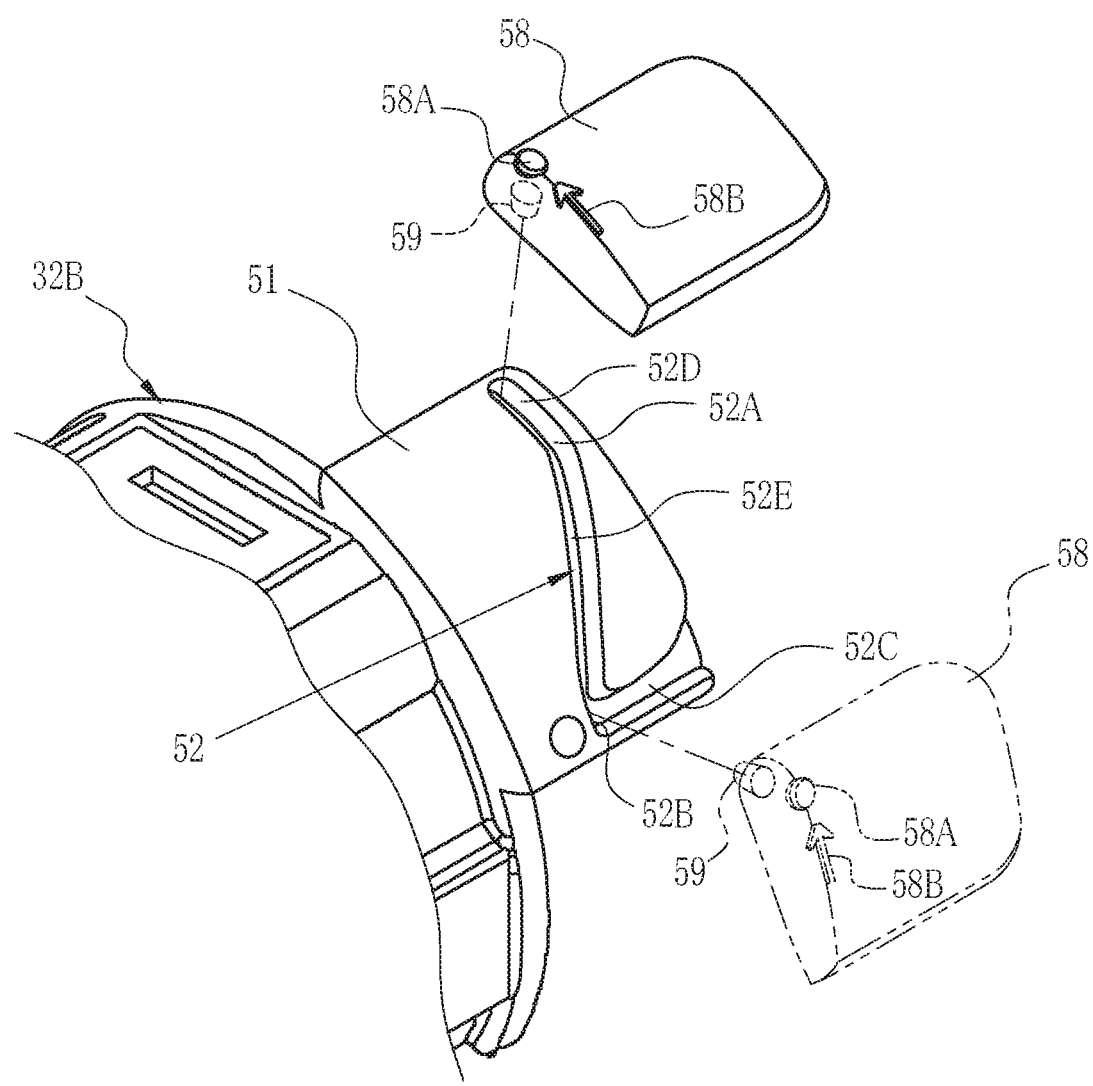
FIG. 14 is an explanatory view of a cam groove.

As shown in FIG. 14, the outer peripheral surface of the cam plate 51 is formed of a curved surface in accordance with the curvature of the head section outer sleeve 32B (see also FIGS. 3 and 4). The cam groove 52 has an inclined section 52E inclined with respect to the axial direction, and a first end 52A on one side of the inclined section 52E and a second end 52B on the other side are different in position in the Z-axis direction. The first end 52A is relatively positioned in the proximal side, and the second end 52B is positioned in the distal side, regarding the Z-axis direction.

In addition to the inclined section 52E, the cam groove 52 has a guide groove 52C and a linear section 52D. The guide groove 52C is connected to the second end 52B at one end, and extends in the Z-axis direction toward the proximal side. The linear section 52D is connected to the first end 52A at one end, and extends in the circumferential direction.

As shown in FIGS. 12A, 12B and 13A, 13B, in a state where the trocar shaft 17 is attached to the trocar with camera 16, the handle member 54 is attached to the head section inner sleeve 32A by the engagement between the engaging claw 54A and the fitting groove 43B. Therefore, the position of the trocar shaft 17 in the Z-axis direction is fixed with respect to the inner cylinder member 16A. When the trocar shaft 17 is attached to the trocar with camera 16, the cam pin 59 provided on the head section outer sleeve 32B and the cam groove 52 provided on the head section inner sleeve 32A engage with each other. Since the position of trocar shaft 17 in the Z-axis direction is fixed with respect to the inner cylinder member 16A, as the trocar shaft 17 rotates, the engagement of the cam pin 59 with the inclined section 52E of the cam groove 52 causes the outer cylinder member 16B to slide relative to the trocar shaft 17 and the inner cylinder member 16A.

Specifically, first, as shown in FIGS. 12A and 13A, when the pipe section outer sleeve 31B is in the holding position, the camera section 36 is in the storage position. When in the holding position, the cam pin 59 is located in the section between the first end 52A and the linear section 52D of the cam groove 52. The initial position of the trocar shaft 17 is a position where the cam pin 59 contacts on the end opposite to the first end 52A side in the linear section 52D. That is, the initial position of the trocar shaft 17 is the end position when the trocar shaft 17 is rotated counterclockwise as viewed from the distal side in the Z-axis direction.

Even when the trocar shaft 17 is rotated clockwise as viewed from the distal side, while the cam pin 59 is positioned between the initial position and the first end 52A, that is, while the cam pin 59 is in the section of the linear section 52D, the pipe section outer sleeve 31B does not slide in the axial direction and maintains the holding position. The linear section 52D is provided to secure a play that prevents the pipe section outer sleeve 31B from starting to slide immediately after the trocar shaft 17 is rotated. Because of this play, even when the trocar shaft 17 at the initial position is slightly rotated carelessly, it is prevented from releasing the holding of the camera section 36.

As the trocar shaft 17 starts to rotate clockwise from the initial position as viewed from the distal side, the cam pin 59 reaches the first end 52A. Then, as the trocar shaft 17 is further rotated clockwise, the cam pin 59 engages with the inclined section 52E of the cam groove 52, and the engagement position of the cam pin 59 moves from the first end 52A toward the second end 52B. By the interaction between the cam pin 59 and the inclined section 52E, as shown in FIGS. 12B and 13B, the pipe section outer sleeve 31B slides backward with respect to the pipe section inner sleeve 31A and retracts to the release position. As a result, since the holding of the camera section 36 is released, the camera section 36 pops up and deploys to the deployed position.

Here, the position where the cam pin 59 of the trocar shaft 17 reaches the second end 52B is defined as a release completion position of the trocar shaft 17. The release completion position is the end position of the clockwise rotation of the trocar shaft 17.

On the other hand, as shown in FIGS. 12B and 13B, when the camera section 36 is in the deployed position, the pipe section outer sleeve 31B is in the release position, and the trocar shaft 17 is in the release completion position. In the release completion position, the cam pin 59 is located at the second end 52B of the cam groove 52. From this state, as the trocar shaft 17 is rotated counterclockwise as viewed from the distal side, the cam pin 59 moves from the second end 52B to the first end 52A of the inclined section 52E. Due to the interaction between the cam pin 59 and the inclined section 52E of the cam groove 52, as shown in FIGS. 12A and 13A, the pipe section outer sleeve 31B slides forward with respect to the pipe section inner sleeve 31A and advances to the holding position.

By advancing the pipe section outer sleeve 31B, the housing 64 corresponding to the rear part of the camera section 36 in the deployed position is pressed by the tip of the pipe section outer sleeve 31B, and the camera section 36 is rotated about the rotation pin 65 and pushed into the storage position. In the storage position, the rear part of the camera section 36 is covered with the tip of the pipe section outer sleeve 31B. As a result, the pop-up deployment to the deployed position of the camera section 36 by the bias of the spring 71 is restricted, and the camera section 36 is held at the storage position.

As described above, since the cam groove 52 and the cam pin 59 constitute the operation mechanism for sliding the pipe section outer sleeve 31B to the proximal side by the rotation operation of the trocar shaft 17, a smoother slide operation of the pipe section outer sleeve 31B becomes possible compared to the case where the pipe section outer sleeve 31B is slid by hand. In case that the medical staff ST who is the operator directly grips and slides the pipe section outer sleeve 31B, the gripping force of the hand easily applies a force in a direction other than the Z-axis direction of the pipe section outer sleeve 31B. Such a force inhibits a smooth sliding of the pipe section outer sleeve 31B. However, in case that the force acting in the direction other than the Z-axis direction with respect to the pipe section outer sleeve 31B is reduced by the above operation mechanism, the smooth slide operation of the pipe section outer sleeve 31B becomes possible.

In addition, when the pipe section outer sleeve 31B is in the release position, the cam pin 59 is located at the second end 52B of the cam groove 52. Since the guide groove 52C is formed to extend from the second end 52B in the axial direction, by moving the cam pin 59 along the guide groove 52C, the trocar shaft 17 can be axially slid toward the proximal side with respect to the pipe section outer sleeve 31B. As shown in FIGS. 12B and 13B, when the pipe section outer sleeve 31B is in the release position, the camera section 36 is in the deployed position. In the pipe section inner sleeve 31A, since the camera section 36 is retracted from behind the puncture member 55, the puncture member 55 can be retracted. Therefore, in a state where the camera section 36 is deployed, it is possible to extract the trocar shaft 17 from the trocar with camera 16.

Also, when attaching the trocar shaft 17 to the trocar with camera 16, the pipe section outer sleeve 31B of trocar with camera 16 is put in the state where the trocar shaft 17 has been extracted, that is, the pipe section outer sleeve 31B is set to the release position where the camera section 36 is in the deployed position, as shown in FIGS. 12B and 13B. In this state, the shaft member body 56 is inserted from the head section 32 into the insertion hole 33 of the pipe section 31. Since the camera section 36 is in the deployed position, the camera section 36 is retracted from the path of the puncture member 55 also at the tip of the pipe section 31. Therefore, the puncture member 55 can be protruded from the tip of the pipe section 31.

Thereafter, the handle member 54 is rotated to align the position of the cam pin 59 with the position of the guide groove 52C. When the positions of the cam pin 59 and the guide groove 52C are aligned, the circumferential position of the engaging claw 54A shown in FIGS. 6 and 7 also faces the cutout 43C of the fitting groove 43B. From this state, as the trocar shaft 17 is advanced toward the distal side with the cam pin 59 following along the guide groove 52C, and the cam pin 59 reaches the second end 52B, the engaging claw 54A enters into the fitting groove 43B from the cutout 43C. As the trocar shaft 17 is rotated to the initial position, the interaction between the cam pin 59 and the cam groove 52 causes the pipe section outer sleeve 31B to advance to the holding position and the camera section 36 to be stored as shown in FIGS. 12A and 13A.

In this way, the guide groove 52C functions as a groove for starting and releasing the engagement of the cam pin 59 of the trocar shaft 17 and the cam groove 52 of the pipe section outer sleeve 31B when the trocar shaft 17 is attached to or removed from the trocar with camera 16.

On the other hand, in the cam groove 52, on the side where the first end 52A and the linear section 52D exist, a guide groove for disengaging the cam pin 59 is not formed. Therefore, in the state where the pipe section outer sleeve 31B is in the holding position, that is, the camera section 36 is in the storage position as shown in FIGS. 12A and 13A, withdrawal of the trocar shaft 17 is restricted. As shown in FIG. 13A, in the storage position, the camera section 36 is stored in the storage space formed by the connecting member 57 of the trocar shaft 17. If an extraction operation of the trocar shaft 17 is carelessly performed in this state, the rear end of the puncture member 55 may come into contact with the camera section 36, possibly damaging the camera section 36. In order to prevent this, the guide groove 52C is formed only on the second end 52B side and is not formed on the first end 52A side.

Further, as shown in FIG. 5, two pairs of the cam pin 59 on the pin arrangement plate 58 and the cam groove 52 on the cam plate 51 are provided, and these pairs are provided around the Z-axis of the outer cylinder member 16B so as to be opposite to each other at an interval of about 180° in the circumferential direction. Since a plurality of pairs of the cam pin 59 and the cam groove 52 are provided and arranged to be opposite to each other, the engagement state is stabilized. Also, it is easy to grip and has good operability.

In addition, since the trocar shaft 17 is provided with the handle member 54 with a larger diameter compared to the shaft member 53, the trocar shaft 17 can be easily rotated.

Further, as shown in FIG. 14, in the handle member 54 of the trocar shaft 17, a position arrangement mark 58A and a direction mark 58B are provided on the pin arrangement plate 58 provided with the cam pin 59 engaging with the cam groove 52. The position mark 58A is arranged on the outer peripheral surface of the pin arrangement plate 58, and indicates the position of the cam pin 59 arranged on the inner peripheral surface.

Since the cam pins 59 are provided on the inner peripheral surface of the pin arrangement plate 58, they are difficult to be seen from the outside. By providing the position mark 58A on the outer peripheral surface of the pin arrangement plate 58, it becomes easy to grasp the position of the cam pin 59 from the outside, and to check the engagement state between the cam pin 59 and the cam groove 52, such as which part of the cam pin 59 is engaged with the cam groove 52. This makes it easy to operate the deployment and storage of the camera section 36 through the trocar shaft 17 and to attach and detach the trocar shaft 17 to the outer cylinder member 16B.

The direction mark 58B indicates the rotational direction when the trocar shaft 17 is attached to the head section 32, that is, the rotational direction from the release completion position to the initial position of the trocar shaft 17.

Note that in this embodiment, the cam formed on the cam plate 51 is the cam groove and the cam formed on the pin arrangement plate 58 is the cam pin. However, the first cam section the cam formed on the cam plate 51 may be a cam pin and the cam formed on the pin arrangement plate 58 may be a cam groove.

[Deployment Assist Mechanism of Camera Section]

As described above, when the trocar shaft 17 is rotated, the holding of the camera section 36 by the pipe section outer sleeve 31B is released, and the camera section 36 pops up and deploys to the deployed position by the bias of the spring 71. The trocar apparatus with camera 12 has a deployment assist mechanism in which the connecting member 57 contacts on the camera section 36 and pushes the camera section 36 from the storage position to the deployed position, when the trocar shaft 17 is rotated during the deployment of the camera section 36. The deployment assist mechanism is constituted by the trocar shaft 17 which is rotatable in the pipe section inner sleeve 31A and has the connecting member 57 which can contact with the camera section 36.

Figure 15C:
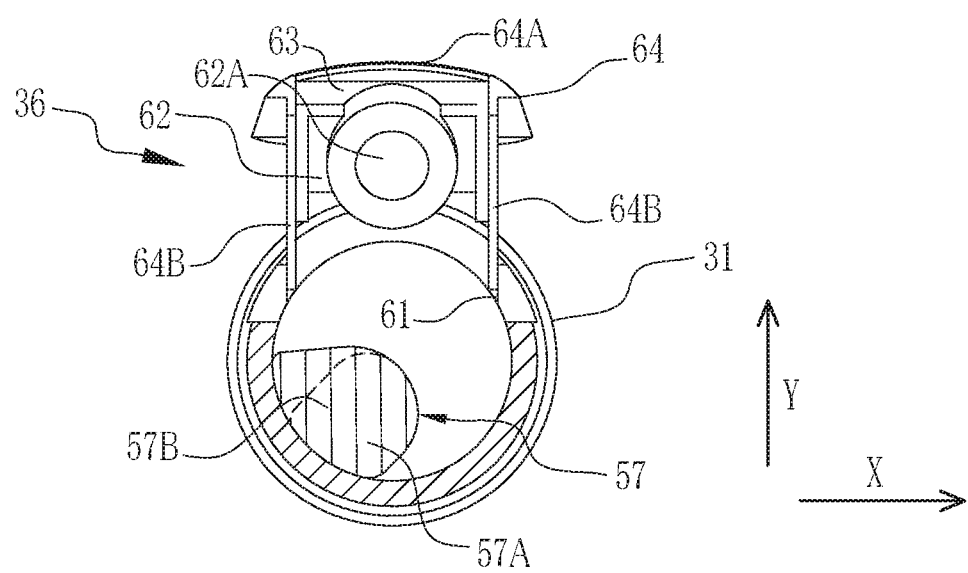
FIG. 15C is an explanatory view of the deployment assist mechanism in a state where the trocar shaft is in a terminal position.

FIGS. 15A to 15C show a cross section (X-Y cross section) orthogonal to the Z-axis direction of the pipe section 31 in a section where the camera section 36 and the connecting member 57 are disposed. As shown in FIGS. 15A to 15C, in the cross section of the pipe section 31, the connecting member 57 is disposed at a lower position opposite to the camera section 36 disposed on the upper part of the pipe section 31. FIGS. 15A and 15B show the camera section 36 in the storage position, and FIG. 15C shows the camera section 36 in the deployed position.

Further, in FIG. 15A, the rotational position of the trocar shaft 17 indicates the initial position, that is, a state where the cam pin 59 is in the linear section 52D of the cam groove 52 (see FIG. 3). In FIG. 15B, the rotational position of the trocar shaft 17 indicates a state in which the cam pin 59 is in the process of moving from the first end 52A to the second end 52B of the inclined section 52E. In FIG. 15C, the rotational position of the trocar shaft 17 indicates the release completion position, that is, a state where the cam pin 59 is at the second end 52B of the cam groove 52 (see FIG. 4).

As shown in FIGS. 15A to 15C, when the pipe section 31 is viewed from the front end side in the Z-axis direction, a cross section of the connecting member 57 has a chevron shape in which a foot extends from the radial center of the pipe section 31 toward the inner wall of the pipe section 31. The bottom surface on the foot side of the connecting member 57 has a curved shape in accordance with the curvature of the inner wall of the pipe section inner sleeve 31A, and contacts on the inner wall of the pipe section inner sleeve 31A. When the trocar shaft 17 rotates clockwise, the connecting member 57 rotates clockwise along the inner wall of the pipe section inner sleeve 31A.

When the trocar shaft 17 rotates clockwise from the initial position shown in FIG. 15A, and reaches the position shown in FIG. 15B, the connecting member 57 starts contact on the side face section 64B of the camera section 36. Since the cam pin 59 and the inclined section 52E of the cam groove 52 are engaged in the state shown in FIG. 15B, when the trocar shaft 17 rotates, the pipe section outer sleeve 31B also slides toward the release position. Therefore, the holding of the camera section 36 is gradually released according to the slide of the pipe section outer sleeve 31B. Then, the camera section 36 starts popping up by the biasing force of the spring 71 toward the deployed position. At this timing, the connecting member 57 starts contact with the camera section 36 and pushes the camera section 36 toward the deployed position.

Due to assistance from the pressing force of the connecting member 57 in addition to the biasing force of the spring 71 to make the camera section 36 pop up and deploy, the pop-up of the camera section 36 can be reliably performed compared with a case where the pop-up is performed only by the biasing force of the spring 71. More specifically, the fat 23A (see FIGS. 24A and 24B) or the like may be attached to the outer peripheral surface of the camera section 36, which may be a resistance at the time of pop-up. Even in such a case, since the deployment assist mechanism constituted of the connecting member 57 is provided, the pop-up can be reliably performed.

Figure 16A:
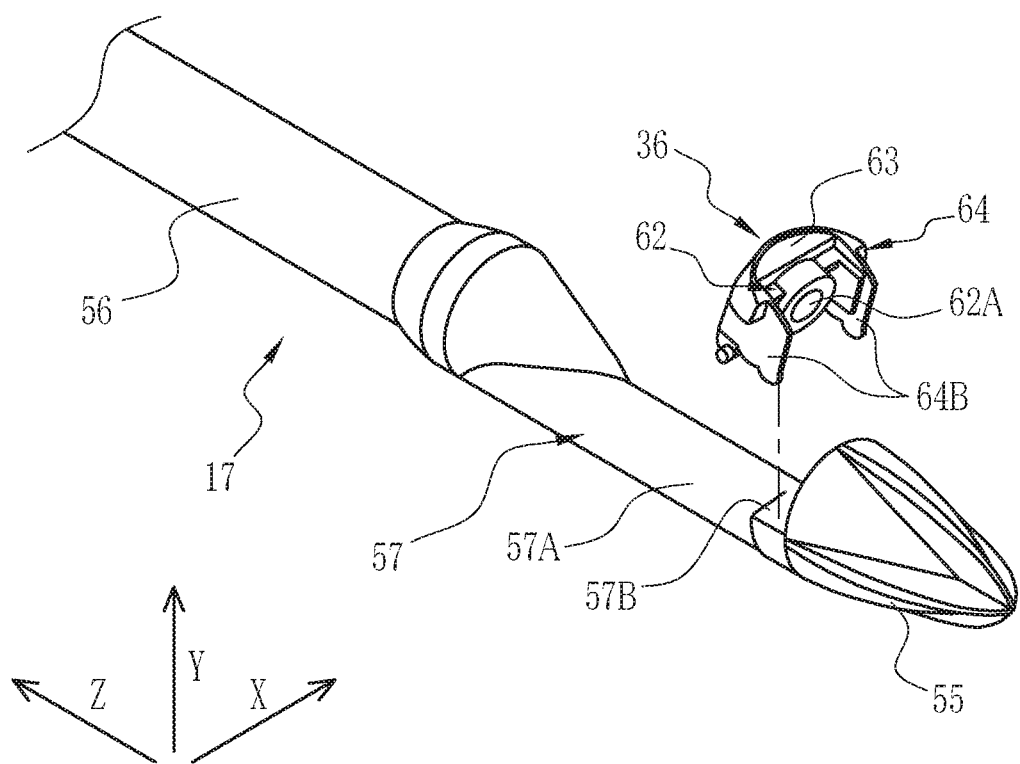
FIG. 16A is an explanatory view showing a positional relationship between a pressing part of the trocar shaft and the camera section.
Figure 16B:
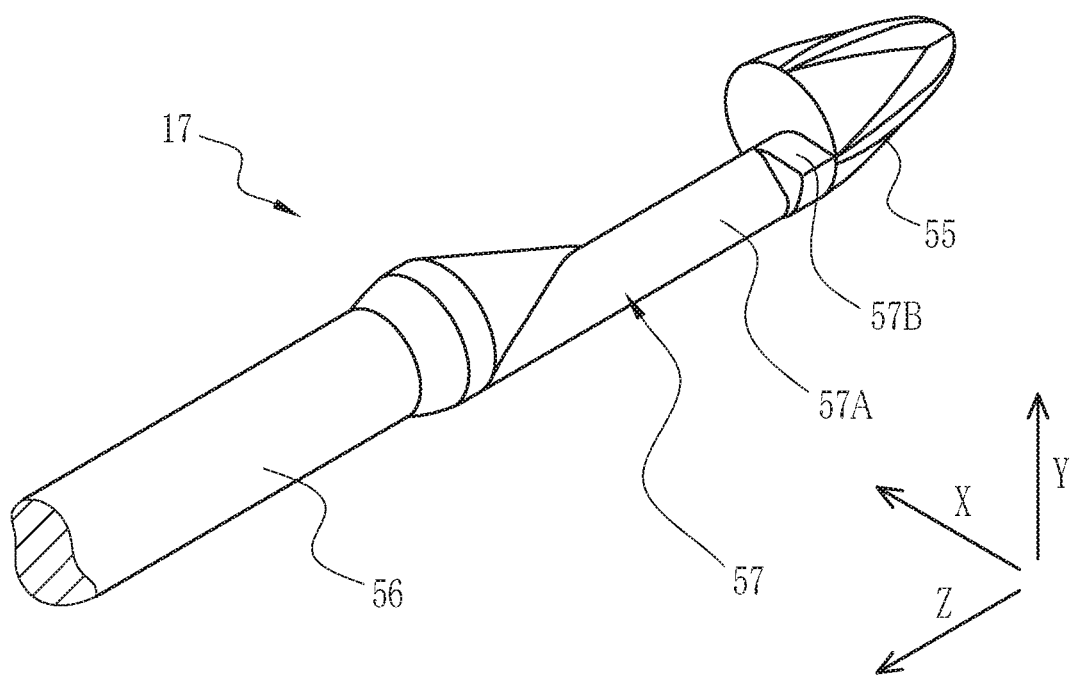
FIG. 16B is a rear perspective view of the pressing part of the trocar shaft.

As shown in FIGS. 15A to 15C, in the connecting member 57, on the slope in contact with the side face section 64B, a pressing part 57B protruding outward from a body part 57A is provided. Further, as shown in FIGS. 16A and 16B, the pressing part 57B is not provided over the entire length of the connecting member 57 in the Z-axis direction, but is provided over a part thereof. Specifically, the pressing part 57B is provided in a range opposed to the side face section 64B of the camera section 36 in the Z-axis direction of the connecting member 57. By minimizing the range where the pressing part 57B is provided, it is possible to prevent the storage space of the camera section 36 from being unnecessarily compressed.

Also, as shown in FIG. 15A, when the trocar shaft 17 is in the initial position and the camera section 36 is in the storage position, the center position of the connecting member 57 in the width direction (X-axis direction) is offset from the center line C1 in the width direction (X-axis direction) of the camera section 36, in the case where the pipe section 31 is viewed from the distal side in the Z-axis direction. The center line C1 is a line connecting the center position of the camera section 36 in the width direction (X-axis direction) and the center of the pipe section 31. The center line C2 is a center line in the width direction (X-axis direction) of only the body part 57A of the connecting member 57, not including the pressing part 57B. Being offset means that the center line C1 and the center line C2 do not match.

More specifically, in FIG. 15A, in a state where the camera section 36 is in the storage position, the connecting member 57 is disposed to face the camera section 36. In this state, the center line C1 in the width direction of the camera section 36 and the center line C2 in the width direction (X-axis direction) of the connecting member 57 do not match, and the center line C2 is offset with respect to the center line C1 in the opposite direction to the slope contacting on the side face section 64B (right direction in FIG. 15A).

Since the center position of the connecting member 57 in the width direction (X-direction) is offset from the center line C1 of the camera section 36 in the state that the trocar shaft 17 is in the initial position and the camera section 36 is in the storage position, it is easy to adjust the amount of rotation of the trocar shaft 17, as described below.

That is, by its rotation, the trocar shaft 17 functions not only as the deployment assist mechanism of the camera section 36, but also functions as the operation mechanism that slides the pipe section outer sleeve 31B to deploy and store the camera section 36. Thus, in the case that the trocar shaft 17 has multiple functions, it is necessary to adjust the amount of rotation of the trocar shaft 17 in accordance with each function.

For example, when the amount of rotation of the trocar shaft 17 required for the operation mechanism is determined, the amount of stroke of the connecting member 57 (the amount of rotation of the connecting member 57 in the circumferential direction) is also determined. In order for the deployment assist mechanism to function, the distance between the connecting member 57 and the side face section 64B of the camera section 36 must be adjusted in accordance with the determined stroke amount. By offsetting the connecting member 57, it is easy to finely adjust the distance between the connecting member 57 and the side face section 64B. Since it is easy to make fine adjustments, even when the trocar shaft 17 have multiple functions, the amount of rotation required for one function can be determined with a certain degree of freedom, and as a result the amount of rotation of the trocar shaft 17 can be easily adjusted.

In other words, by making the cross-section of the connecting member 57 to have such the shape and arrangement, flexibility in the design is ensured. Specifically, in this embodiment, the center line C2 of the body part 57A of the connecting member 57 is offset from the center line C1 of the camera section 36. However, theoretically, even in the case that the pressing part 57B is provided, it is possible to provide the body part 57A such that the center line C2 and the center line C1 coincide (without offset).

The reason for offsetting in this example is that in order to secure the distance between pressing part 57B of the connecting member 57 and the side face section 64B of the camera section 36 in the cam design, since the deployment of the camera section 36 is also related to the sliding amount of the outer cylinder member 16B. By offsetting the center line C2 with respect to the center line C1 of the body part 57A and making the cross-sectional shape of the connecting member 57 including the pressing part 57B asymmetric with respect to the center line C2, the distance between the side face section 64B and the pressing part 57B is extended. Thus, flexibility in the design is improved.

[Locking Mechanism at Deployment and Storage of Camera]

The trocar apparatus with camera 12 is provided with the outer cylinder locking mechanism which regulates the slide in the direction of the Z-axis of the outer cylinder member 16B having the pipe section outer sleeve 31B to lock the outer cylinder member 16B in each of the holding position and the release position. As described above, the lock releasing member 46 is the operation member that performs the releasing operation of the outer cylinder locking mechanism, and configures the outer cylinder locking mechanism together with the engaging member 47.

As shown in FIG. 17, the engaging member 47 formed on the outer peripheral surface of the head section inner sleeve 32A has two engaging grooves 47A and 47B extending in the direction orthogonal to the Z-axis direction. Each engaging groove 47A, 47B has a different position in the Z-axis direction. The engaging groove 47A is a groove for locking the outer cylinder member 16B with the pipe section outer sleeve 31B in the holding position, and the engaging groove 47B is a groove for locking the outer cylinder member 16B with the pipe section outer sleeve 31B in the release position.

The lock releasing member 46 is attached to the outer periphery of the head section outer sleeve 32B of the outer cylinder member 16B. The lock releasing member 46 has an operation section 46A and a supporting section 46B. The supporting section 46B is connected to the operation section 46A and supports the operation section 46A in the head section outer sleeve 32B. A step is formed between the operation section 46A and the supporting section 46B, and the longitudinal cross section of the lock releasing member 46 has a substantially crank shape.

In the part where the operation section 46A and the supporting section 46B are joined in the lock releasing member 46, mount pins 46C are provided at both ends in the width direction. The supporting section 46B is provided with a mount hole 46D to which a spring 68 for biasing the lock releasing member 46 in a predetermined direction is attached. Further, in the supporting section 46B, an engaging projection 46E (see FIGS. 19A to 19C) is provided on the side opposite to the mount hole 46D. As will be described later, the engaging projection 46E engages with each of the engaging grooves 47A and 47B and regulates the slide of the outer cylinder member 16B.

The head section outer sleeve 32B is provided with a mounting member 66 for mounting the lock releasing member 46. The mounting member 66 has an opening 66A and a bearing 66B which is formed on the inner periphery of the opening 66A and rotatably supports the mount pin 46C.

Figure 18A:
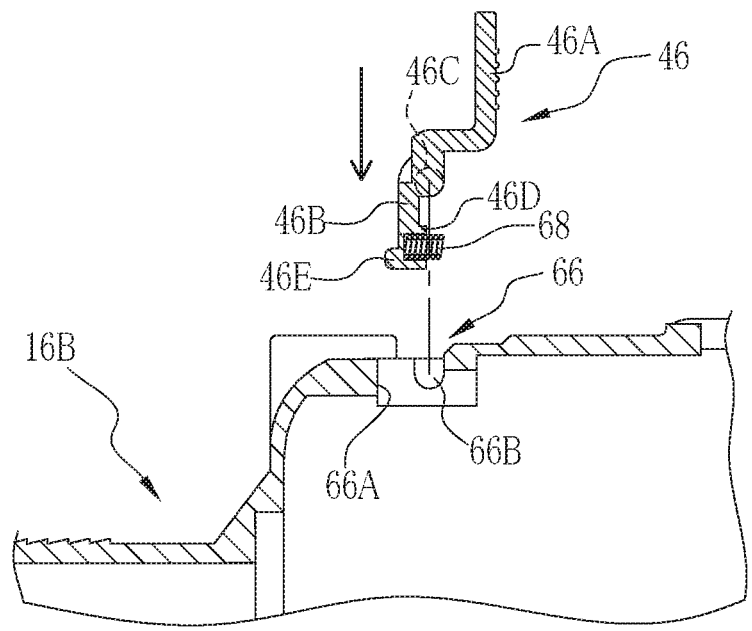
FIG. 18A is a first explanatory diagram of a method for assembling a lock releasing member.
Figure 18B:
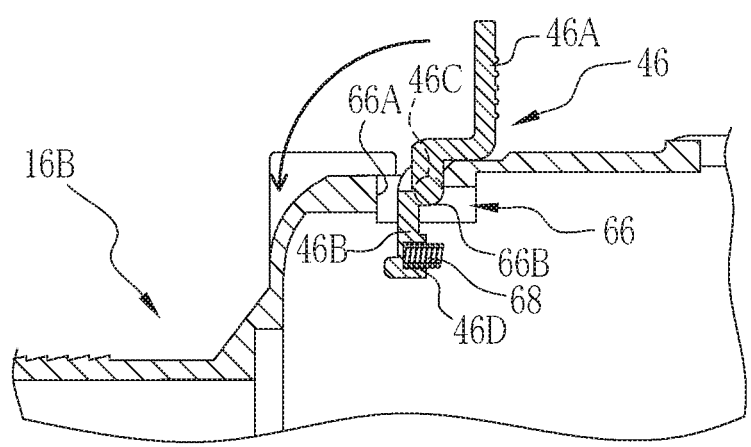
FIG. 18B is a second explanatory diagram of the method for assembling the lock releasing member.
Figure 18C:
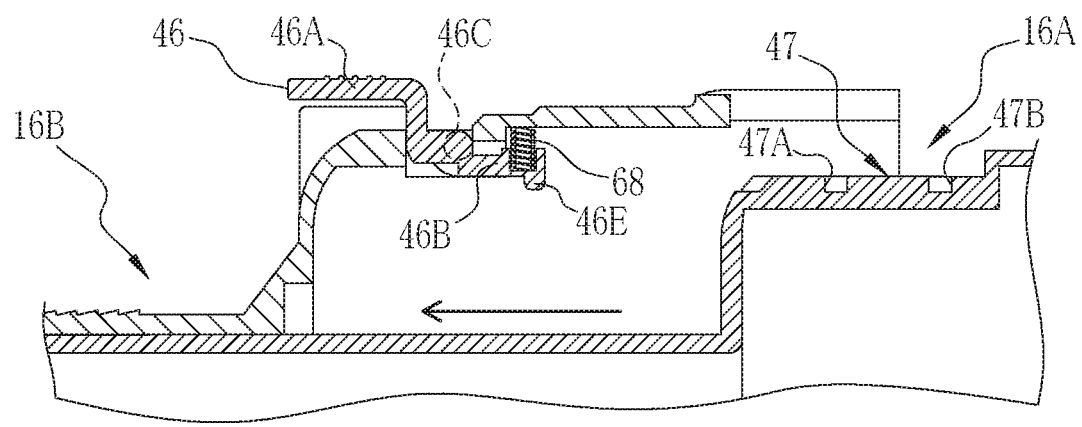
FIG. 18C is a third explanatory diagram of the method for assembling the lock releasing member.

FIGS. 18A to 18C show a method of assembling the lock releasing member 46. As shown in FIG. 18A, the lock releasing member 46 is inserted into the opening 66A, for example, with the spring 68 attached to the supporting section 46B. Then, as shown in FIG. 18B, the mount pin 46C is attached to the bearing 66B. After that, the lock releasing member 46 is rotated about the mount pin 46C, and the posture of the lock releasing member 46 is adjusted so that the supporting section 46B and the inner peripheral surface of the head section outer sleeve 32B become parallel.

In this state, the spring 68 is sandwiched between the supporting section 46B and the inner peripheral surface of the head section outer sleeve 32B. While maintaining this posture, as shown in FIG. 18C, the inner cylinder member 16A is inserted into the outer cylinder member 16B, and the supporting section 46B is sandwiched between the inner peripheral surface of the outer cylinder member 16B and the engaging member 47 formed on the outer peripheral surface of the inner cylinder member 16A. The supporting section 46B is rotated clockwise about the mount pin 46C by the biasing force of the spring 68 in FIG. 18C and biased in a direction to press the engaging projection 46E toward the engaging member 47.

Figure 19A:
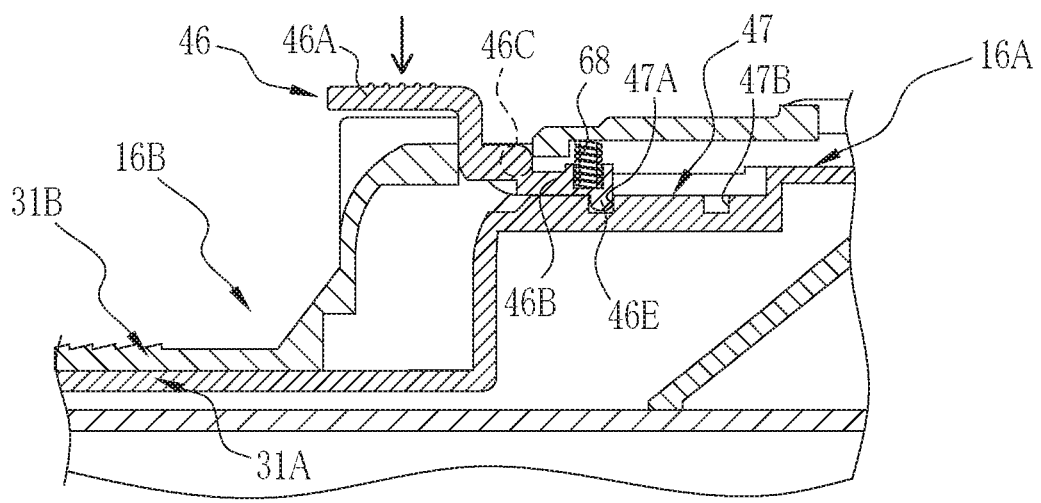
FIG. 19A is an explanatory view of the lock releasing member in a state where an outer cylinder is in a holding position.
Figure 19B:
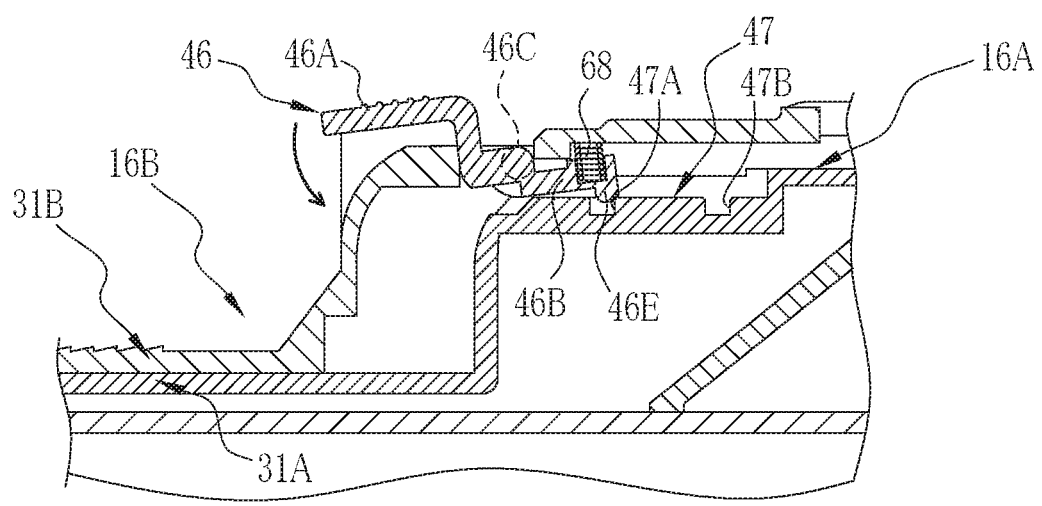
FIG. 19B is an explanatory view of the lock releasing member in a state where the lock of the outer cylinder is released.
Figure 19C:
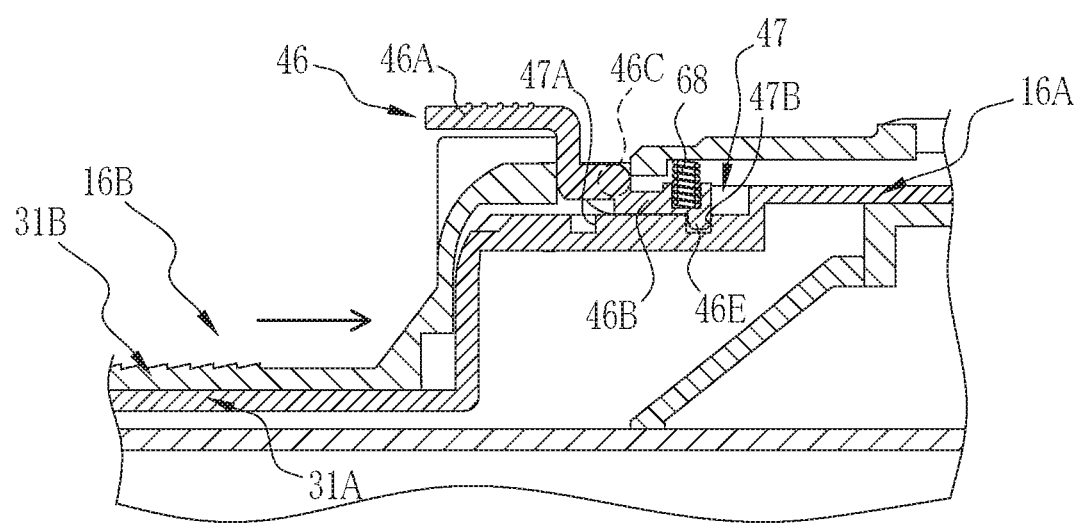
FIG. 19C is an explanatory view of the lock releasing member in a state where the outer cylinder is in a release position.

FIGS. 19A-19C show engagement states of the lock releasing member 46 and the engaging member 47. FIG. 19A shows a state where the pipe section outer sleeve 31B is in the holding position where the camera section 36 is held at the storage position. In the state shown in FIG. 19A, the engaging projection 46E engages with the engaging groove 47A, and the bias of the spring 68 pushes the engaging projection 46E toward the engaging groove 47A. Therefore, the engagement of the engaging projection 46E and the engaging groove 47A restricts the axial slide of the outer cylinder member 16B with respect to the inner cylinder member 16A, and the pipe section outer sleeve 31B is locked at the holding position (see FIGS. 12A and 13A) where the camera section 36 is held at the storage position.

FIG. 19B shows a state in which the slide lock of the outer cylinder member 16B is released by operation of the lock releasing member 46. When the operation section 46A is pressed, the lock releasing member 46 rotates counterclockwise around the mount pin 46C against the bias of the spring 68. By this rotation, the supporting section 46B is separated from the engaging member 47, and the engaging projection 46E and the engaging groove 47A are disengaged. Thereby, the slide lock of the outer cylinder member 16B is released. When the slide lock of the outer cylinder member 16B is released, it is possible to retract the pipe section outer sleeve 31B toward the proximal side to the release position.

FIG. 19C shows a state where the pipe section outer sleeve 31B is in the release position. As shown in FIG. 19B, when the outer cylinder member 16B is retracted toward the proximal side in the unlocked state, the engaging projection 46E of the supporting section 46B reaches the engaging groove 47B. As shown in FIG. 19C, when the engaging projection 46E reaches the engaging groove 47B, the biasing of the spring 68 causes the engaging projection 46E to fall into the engaging groove 47B, and the two become engaged. In the release position where the engaging projection 46E and the engaging groove 47B are engaged, since the holding of the camera section 36 by the pipe section outer sleeve 31B is released, the camera section 36 pops up and deploys.

In the state shown in FIG. 19C, the engaging projection 46E engages with the engaging groove 47B, and the bias of the spring 68 presses the engaging projection 46E toward the engaging groove 47B. Therefore, the engagement of the engaging projection 46E and the engaging groove 47A restricts the axial slide of the outer cylinder member 16B with respect to the inner cylinder member 16A, and the pipe section outer sleeve 31B is locked at the release position (see FIGS. 12B and 13B) that allows the camera section 36 to deploy.

The following effect is obtained by the outer cylinder locking mechanism provided with the lock releasing member 46 and the engaging member 47. That is, in the trocar with camera 16, the outer cylinder member 16B including the pipe section outer sleeve 31B is located at the outermost periphery of the pipe section 31 of the trocar with camera 16. As such the pipe section outer sleeve 31B is used as the operation member for holding into and deploying from the storage position of the camera section 36, the operator's hand is easy to touch and an inadvertent slide against the operator's intention is likely to occur.

When the pipe section outer sleeve 31B slides carelessly, there becomes a concern that the camera section 36 which should be in the storage position may be deployed or the camera section 36 which should be in the deployed position may be stored contrary to the operator's will. According to the outer cylinder locking mechanism, since the pipe section outer sleeve 31B can be locked at the holding position and the release position, it is possible to prevent the careless slide of the pipe section outer sleeve 31B.

In addition, the engagement projection 46E, which regulates the slide of the outer cylinder member 16B by engaging with the engaging grooves 47A and 47B, is integrally formed with the lock releasing member 46, so that the structure becomes simple. Therefore, it is advantageous in terms of parts cost and assembly.

Further, since the lock releasing member 46 is disposed in the head section 32 larger in diameter than the pipe section 31, the operability becomes good.

[Bearing Structure of Camera Section]

Figure 20A:
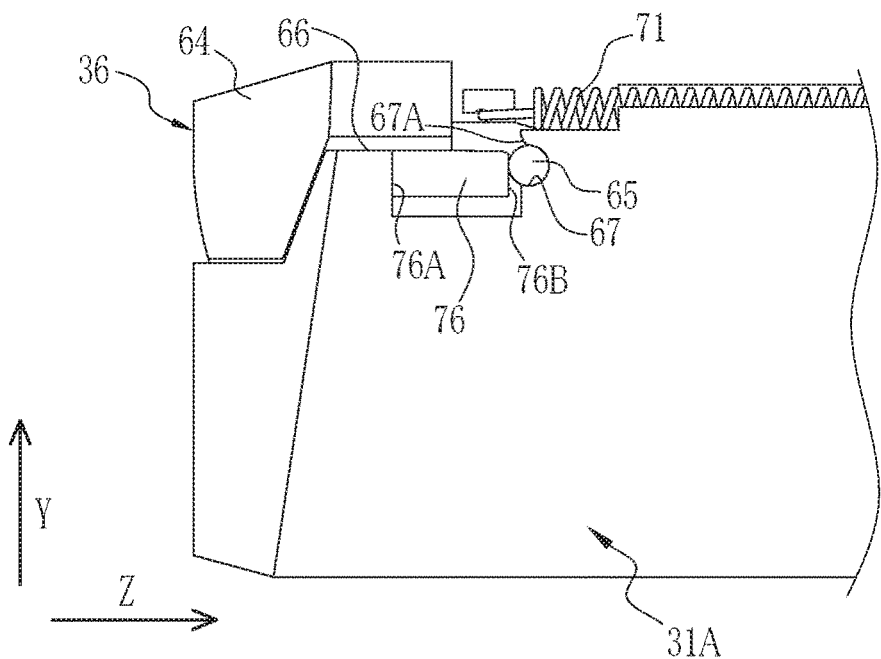
FIG. 20A is an enlarged view of a hinge portion in a state where the camera section is deployed.
Figure 20B:
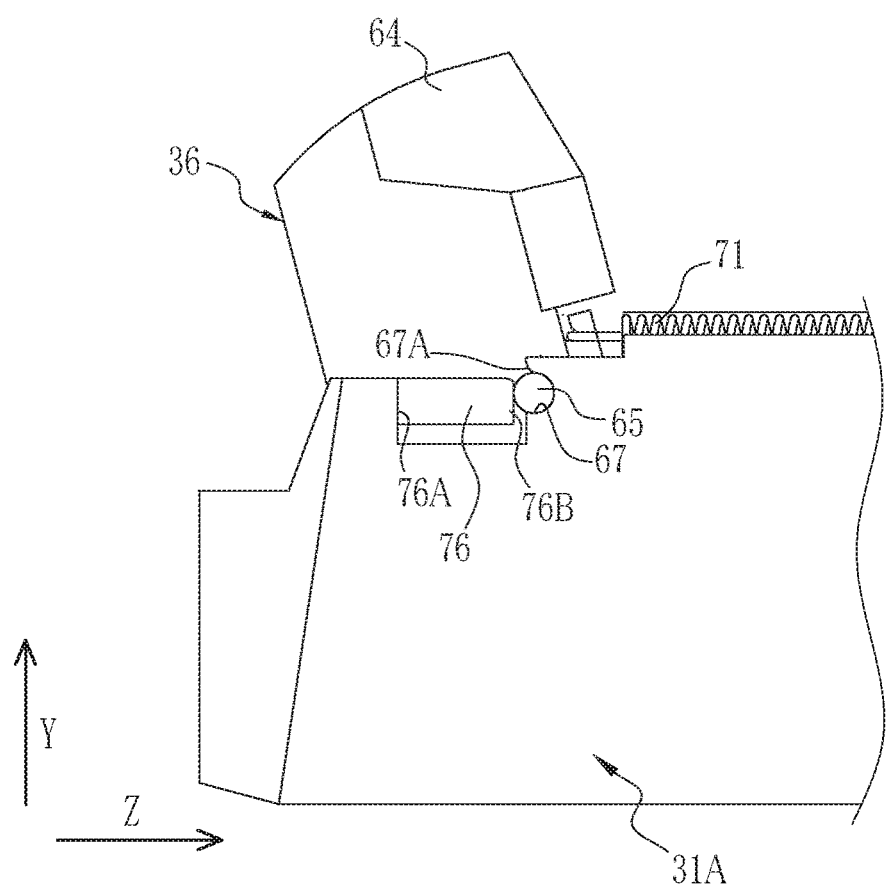
FIG. 20B is an enlarged view of the hinge portion in a state where the camera section is stored.

As shown in FIGS. 20A and 20B, the camera section 36 is attached to the pipe section inner sleeve 31A, and is rotatably supported between the storage position and the deployed position. FIG. 20A shows the camera section 36 in the storage position, and FIG. 20B shows the camera section 36 in the deployed position. As also shown in FIG. 10, the pair of left and right rotation pins 65 are provided at both ends in the width direction (X-axis direction) of the camera section 36, and the each rotation pin 65 is attached to each of the pair of left and right bearings 67 formed in the cutout 61 of the pipe section inner sleeve 31A. The pair of bearings 67 rotatably support the each rotation pin 65.

The each bearing 67 has a distal side receiving opening 67A that receives the rotation pin 65 on the distal side of the pipe section inner sleeve 31A. In the bearing 67, the shape of the cross section orthogonal to the rotation pin 65 is substantially semicircular, and the cutout corresponding to the remaining semicircle corresponds to the distal side receiving opening 67A. The distal side receiving opening 67A can receive the rotation pin 65 entering from the distal side of the pipe section 31 along the Z-axis direction of the pipe section 31. A detachment prevention member 76 for preventing detachment of the rotation pin 65 supported by the bearing 67 is disposed at a position opposite to the distal side receiving opening 67A. The detachment prevention member 76 is an axially extending band-like tongue and is provided in the pipe section inner sleeve 31A.

The detachment prevention member 76 is integrally formed with, for example, the pipe section inner sleeve 31A. One end of the detachment prevention member 76 is a fixed end 76A fixed to the pipe section inner sleeve 31A, and the other end on the proximal side is a free end 76B having elasticity. With this configuration, the detachment prevention member 76 can be elastically deformed such that the free end 76B is displaced in the width direction (X-axis direction) of the camera section 36 with respect to the fixed end 76A (see FIG. 21B). The detachment prevention member 76 is made of resin and is molded integrally with the pipe section inner sleeve 31A. The detachment prevention member 76 is formed to a length such that the free end 76B is located at the distal side receiving opening 67A, and the free end 76B is disposed opposite to the distal side receiving opening 67A. The free end 76B cooperates with the bearing 67 to support the rotation pin 65 and covers the distal side receiving opening 67A to prevent the rotation pin 65 from falling off from the bearing 67. A bearing structure of the camera section 36 is constituted of the rotation pin 65 corresponding to the pivot, the bearing 67, and the detachment prevention member 76.

Figure 21A:
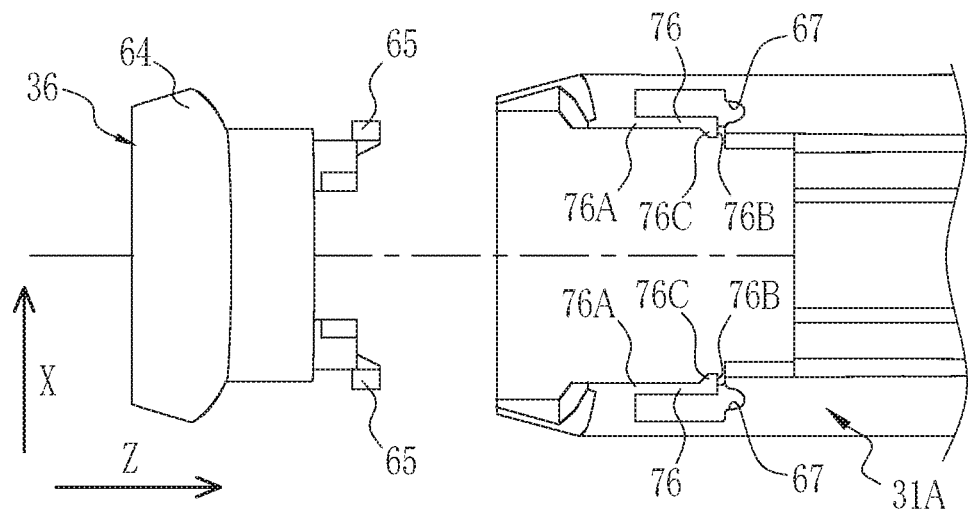
FIG. 21A is a first explanatory diagram of a method for attaching the camera section.
Figure 21B:
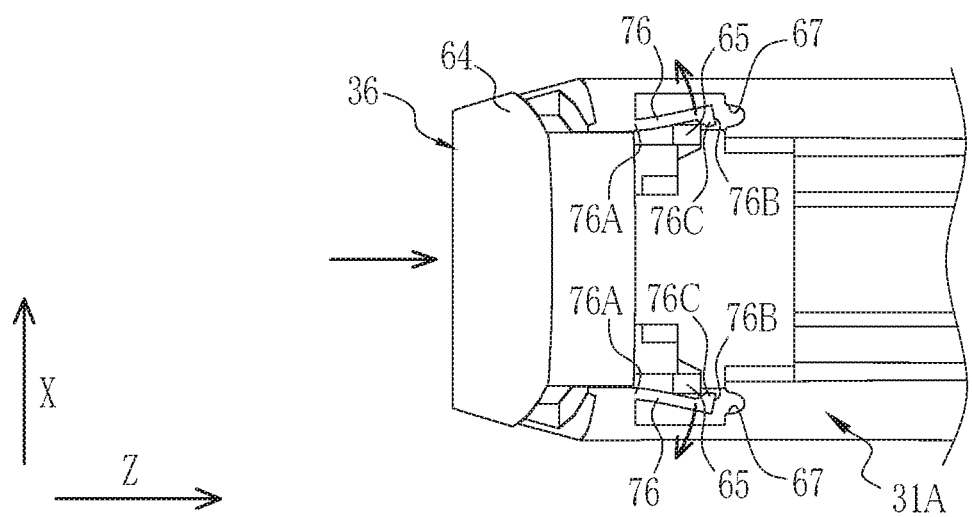
FIG. 21B is a second explanatory diagram of the method for attaching the camera section.
Figure 21C:
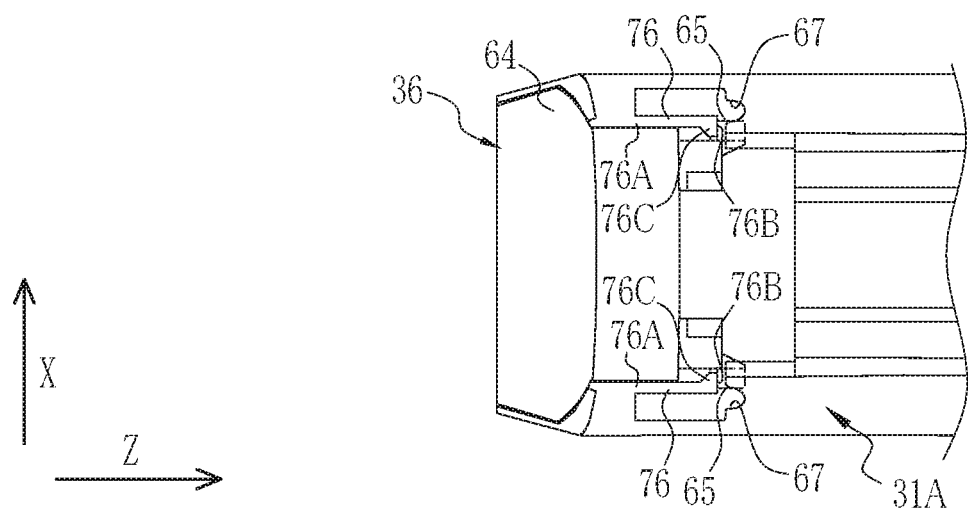
FIG. 21C is a third explanatory diagram of the method for attaching the camera section.

As shown in FIGS. 21A to 21C, the each free end 76B of the left and right detachment prevention members 76 is provided with a projecting section 76C projecting inward, that is, projecting toward the mutually opposing free ends 76B (See also FIG. 10).

FIGS. 21A-21C show how to attach the camera section 36. As shown in FIG. 21A, the camera section 36 is attached to the bearing 67 from the distal end side of the pipe section inner sleeve 31A. At this time, as shown in FIG. 21B, the left and right rotation pins 65 are inserted between the left and right detachment prevention members 76 and contact with the inside of the each detachment prevention member 76. In this state, the camera section 36 is moved along the Z-axis direction of the pipe section inner sleeve 31A.

The distance between the left and right rotation pins 65 is wider than the distance between the left and right detachment prevention members 76. Therefore, in the state where the left and right rotation pins 65 are in contact with the left and right detachment prevention members 76, the free ends 76B elastically deform outward with respect to the fixed ends 76A. The elastic deformation of the detachment prevention members 76 continue until the left and right rotation pins 65 are accepted by the left and right bearings 67 through the distal side receiving openings 67A.

As shown in FIG. 21B, when the left and right rotation pins 65 moving toward the bearings 67 from the distal end reach the positions of the projecting sections 76C, the outward deformation amount of the free ends 76B of the detachment prevention members 76 become maximum. In this state, the free end 76B withdraws from the front of the distal side receiving opening 67A of the bearing 67. This allows the rotation pin 65 to enter the bearing 67.

As the camera section 36 is further moved toward the proximal side, the rotation pin 65 enters the bearing 67 and is accepted, as shown in FIG. 21C. When the rotation pin 65 is received by the bearing 67, the contact between the inside of the detachment prevention member 76 and the rotation pin 65 is released. Therefore, the outwardly deformed free end 76B is displaced inward by elasticity, and returns to the initial position opposite to the distal side receiving opening 67A. As a result, since the distal side receiving opening 67A of the bearing 67 that has received the rotation pin 65 is covered, it is possible to prevent the rotation pin 65 from falling off from the bearing 67. In addition, the outer peripheral surface of the rotation pin 65 around the axis is covered by the bearing 67 and the distal side receiving opening 67A, so as to be supported rotatably by these cooperation.

Since the bearing structure of the rotation pin 65 is configured by the bearing 67 having the distal side receiving opening 67A and the detachment prevention member 76 disposed opposite to the distal side receiving opening 67A, it becomes possible to prevent lowering of strength of the rotation pin 65 of the camera section 36 while securing the good mountability of the camera section 36.

That is, since the distal side receiving opening 67A is configured by a substantially semicircular notch, the cross-sectional shape in the direction orthogonal to the rotation axis can be made circular in the rotation pin 65. If the receiving port of the bearing 67 is smaller than the radius of the rotation pin 65, the rotation pin 65 can not be inserted into the bearing 67. In that case, in order to reduce the cross-sectional size of the rotation pin 65, it is necessary to apply for example a D-cut or an I-cut at least to a part of the rotation pin 65. Such processing leads to a reduction in the strength of the rotation pin 65. If the strength of the rotation pin 65 decreases, for example, the rotation pin 65 may be damaged in the abdominal cavity. Such the danger can be avoided by preventing the strength of the rotation pin 65 from being reduced.

Further, since the detachment prevention member 76 is disposed in the distal side receiving opening 67A, the rotation pin 65 is prevented from dropping off from the bearing 67.

Furthermore, since the detachment prevention member 76 is elastically deformable, when attaching the camera section 36 to the bearing 67, the detachment prevention member 76 can be elastically deformed and retracted from the distal side receiving opening 67A. Therefore, since the rotation pin 65 can enter the bearing 67 from the distal side receiving opening 67A only by moving the camera section 36 along the axial direction from the distal side, the mountability of the camera section 36 becomes also good.

In addition, the projection section 76C projecting inward is provided at the free end 76B of the detachment prevention member 76. Accordingly, the free end 76B can be largely deformed outward immediately before the rotation pin 65 reaches the distal side receiving opening 67A. As a result, the amount of evacuation of the free end 76B is increased, so that the rotation pin 65 can easily enter into the distal side receiving opening 67A.

Note that in the bearing 67 of this embodiment, the substantially semicircular shape means a semicircle having a circular arc with a length of 50% of the circular circumference, or having a range of plus or minus 10% based on the semicircle, that is, an arc having a length of 40% to 60% of the circular circumference. Regarding the distal side receiving opening 67A, as the length of the arc of the bearing 67 approaches 60%, the size of the opening decreases, and as the length of the arc of the bearing 67 approaches 40%, the size of the opening increases.

For example, if the length of the arc of the bearing 67 is 60%, the size of the distal side receiving opening 67A may be slightly smaller than the radius of the rotation pin 65. However, even in that case, it is possible to receive the rotation pin 65 in the bearing 67 if the distal side receiving opening 67A can be elastically deformed to expand the size of the opening. Further, as the size of the distal side receiving opening 67A is reduced, the effect of preventing the dropout of the rotation pin 65 from the bearing 67 becomes greater.

[Ridge Section of Puncture Member]

Figure 22:
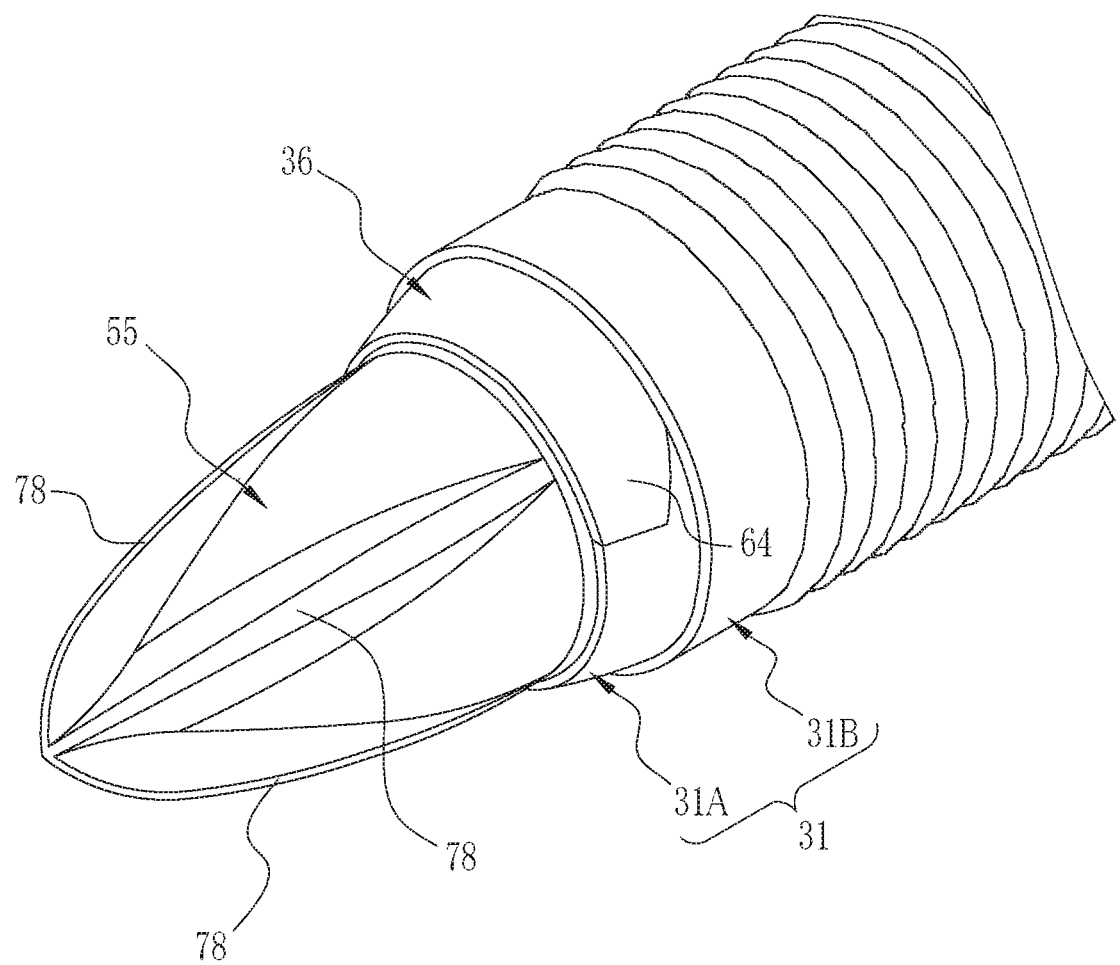
FIG. 22 is an enlarged view showing the positional relationship between a ridge section of a puncture member and the camera section.

As shown in FIG. 22, on the outer peripheral surface of the puncture member 55 of the trocar shaft 17, a plurality of ridge sections 78 protruding in the radial direction and extending along the Z-axis direction of the puncture member 55 are formed. As described in FIGS. 2 and 3, the puncture member 55 is first inserted into the incision part 27 formed in the abdominal wall 23 of the patient P, when inserting the trocar with camera 16 into the abdominal cavity of the patient P. As described above, the abdominal wall 23 is formed of a subcutaneous tissue such as the fat 23A (see FIGS. 24A and 24B), and the puncture member 55 plays the role of spreading the abdominal wall 23. The ridge section 78 tears the subcutaneous tissue and prevents wrapping of a subcutaneous tissue on the outer peripheral surface of the puncture member 55, particularly wrapping of the fat 23A.

In this embodiment, four ridge sections 78 are provided. Note that with regard to the four ridge sections 78, when it is necessary to distinguish each of the ridge sections 78, the symbols will be separately described as the ridge sections 78A to 78D, and if it is not necessary to distinguish them, it will be described simply as the ridge section 78.

Figure 23A:
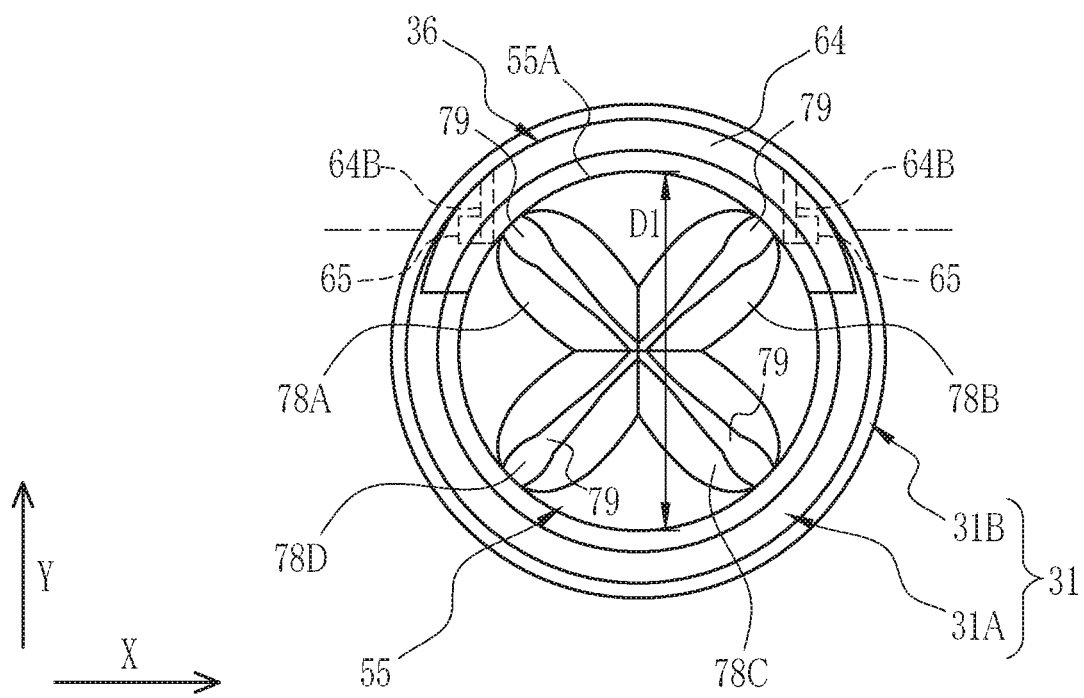
FIG. 23A is a front view of a pipe section and the ridge section of the puncture member, in a state where the camera section is stored.
Figure 23B:
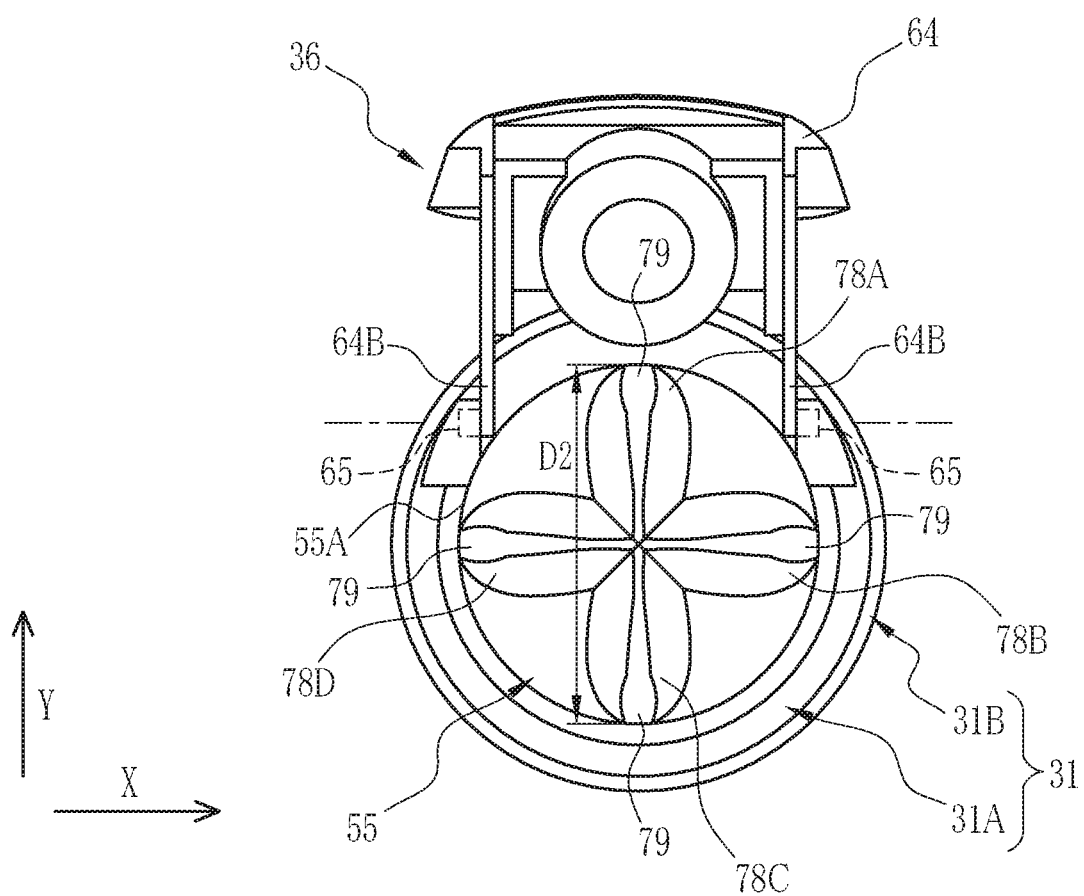
FIG. 23B is a front view of the pipe section and the ridge section of the puncture member, in a state where the camera section is deployed.

As shown in FIGS. 23A and 23B, the four ridge sections 78A, 78B, 78C, 78D are arranged in a crosswise manner as a whole as the puncture member 55 is viewed from the distal end side in the Z-axis direction. Specifically, the four ridge sections 78A, 78B, 78C, 78D are arranged at 90° intervals in the circumferential direction around the Z-axis of the puncture member 55 at the proximal end, and the distal ends of the ridge sections intersect at the distal end of the puncture member 55.

FIG. 23A shows a positional relationship between the plurality of ridge sections 78 and the camera section 36 when the camera section 36 is in the storage position, that is, when the trocar shaft 17 is in the initial position (see FIGS. 3 and 12A and so on). FIG. 23B shows a positional relationship between the plurality of ridge sections 78 and the camera section 36 in the state where the trocar shaft 17 is in the release completion position (see FIGS. 4 and 12B and so on).

As shown in FIG. 23A, when the trocar shaft 17 is in the initial position (the camera section 36 is in the storage position), of the four ridge sections 78A to 78D, the two ridge sections 78A and 78B are arranged at positions where the end on the proximal side corresponds to the position of each hinge section at both ends of the camera section 36 in the circumferential direction about the Z-axis of the puncture member 55. Each hinge section is provided at both ends of the camera section 36 as described above, and is configured by the rotation pin 65 provided on the each side face section 64B of the camera section 36 and the each bearing 67 provided on the inner periphery of the cutout 61.

Figure 24A:
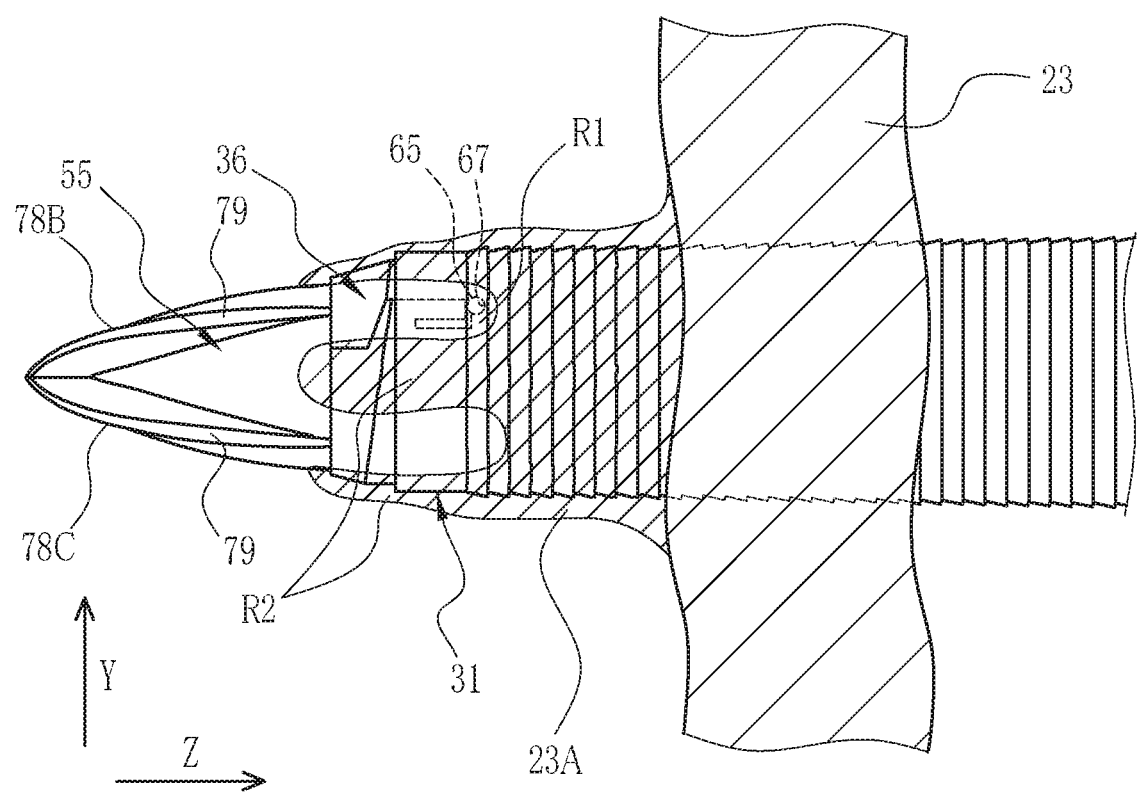
FIG. 24A is a side view showing fat wrapping around the camera section.
Figure 24B:
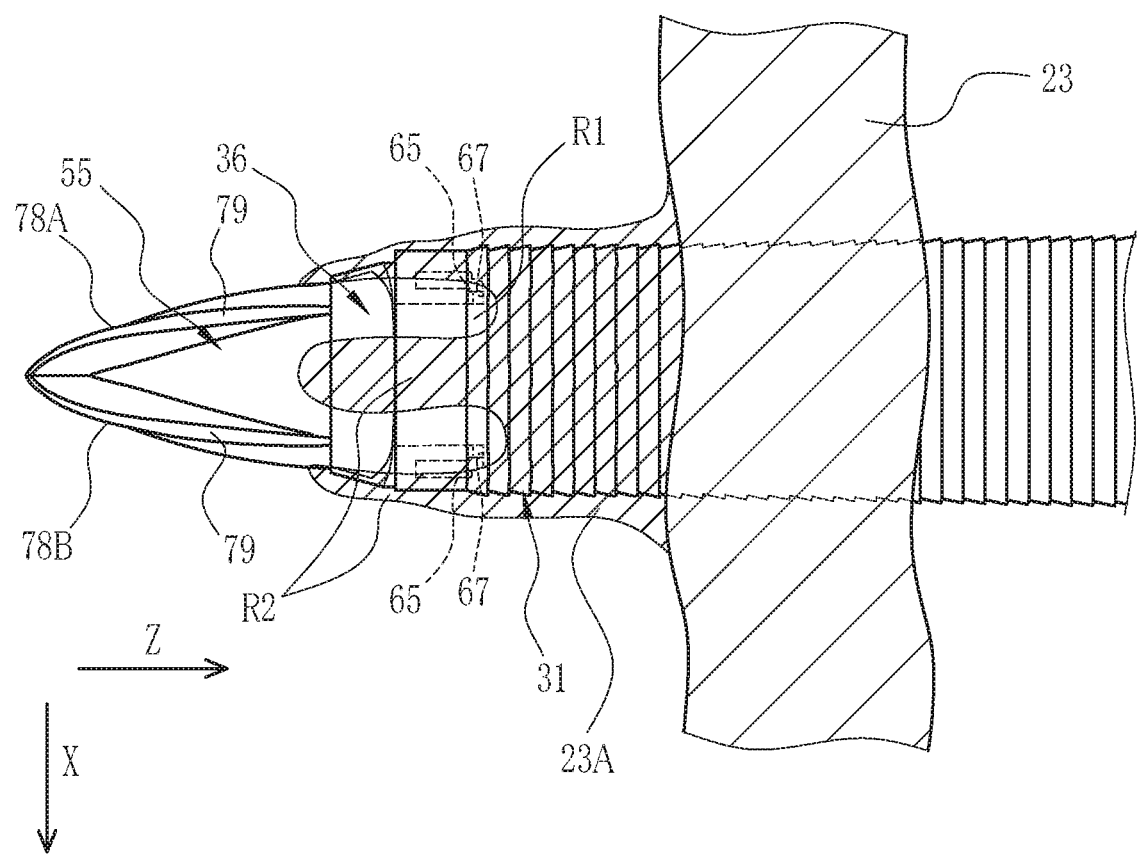
FIG. 24B is a top view showing fat wrapping around the camera section.

FIGS. 24A and 24B are explanatory diagrams showing wrapping of the fat 23A on the distal end of the pipe section 31 in which the camera section 36 is disposed, based on the findings obtained through animal experiments. FIG. 24A is a side view of the pipe section 31 as viewed from the side, and FIG. 24B is a top view of the pipe section 31 as viewed from above where the camera section 36 is disposed. As shown in FIGS. 24A and 24B, in the pipe section 31 behind the puncture member 55, a region R1 corresponding to the ridge section 78 has less wrapping of the fat 23A than the other region R2. Therefore, by arranging the ridge sections 78A and 78B at the positions corresponding to the hinge sections of the camera section 36 provided in the pipe section 31, it is possible to suppress the wrapping of the fat 23A on the peripheral region (the region R1 in FIGS. 24A and 24B) including the hinge sections of the camera section 36.

Since the fat 23A wrapped around the camera section 36 becomes a resistance when the camera section 36 pops up to the deployed position, it becomes a factor that disturbs the smooth deployment of the camera section 36. By arranging the ridge sections 78A and 78B at positions corresponding to the hinge sections of the camera section 36, the wrapping of the fat 23A can be suppressed. This enables smooth deployment of the camera section 36.

Further, in the each ridge section 78, an upper end part 79 corresponding to the ridge line along the Z-axis direction has a flat surface, not a tapered shape like a blade edge. By making the upper end part 79 a flat surface, following effects can be obtained. First, even if the operator touches the puncture member 55 with a hand wearing a rubber glove, the rubber glove can be prevented from being damaged. Second, even when a large force acts on the puncture member 55 when the trocar apparatus with camera 12 is inserted into the abdominal cavity, the ridge section 78 is less likely to be broken than in the case where the upper end part 79 has a tapered shape. Third, breakage of a seal unit contained in the airtight structure unit 42 can be prevented. When inserting the trocar shaft 17 into the trocar with camera 16, the puncture member 55 passes through the airtight structure unit 42. However, by making the ridge section 78 a flat surface, it is possible to prevent the seal unit contained in the airtight structure unit 42 from being damaged.

Further, as shown in FIGS. 23A and 23B, the maximum diameter D2 in the radial direction of the plurality of ridge sections 78 is equal to or less than the maximum diameter D1 of a portion where the ridge section 78 is not formed on the outer peripheral surface 55A of the puncture member 55. In this embodiment, the maximum diameter D1 is the diameter at the proximal end of the tapered shape puncture member 55, and the maximum diameter D2 of the ridge section 78 is a diameter connecting the upper end parts 79 of the plural ridge sections 78 arranged circumferentially at the proximal end of the ridge section 78.

Thus, the maximum protrusion amount of the ridge section 78 can be regulated by setting the maximum diameter D2 of the ridge section 78 to the maximum diameter D1 of the puncture member 55 or less. Therefore, the above-described first to third effects, by making the upper end part 79 of the ridge section 78 a flat surface, can be further enhanced.

Note that although the four ridge sections 78 are provided in this embodiment, the number of ridge sections 78 may be other than four. For example, three or five or more ridge sections 78 may be used, as long as the two ridge sections 78A and 78B disposed at positions corresponding to the hinge sections of the camera section 36 are included. Also, two or more ridge sections 78 may be arranged at a position corresponding to one hinge section.

Figure 25:
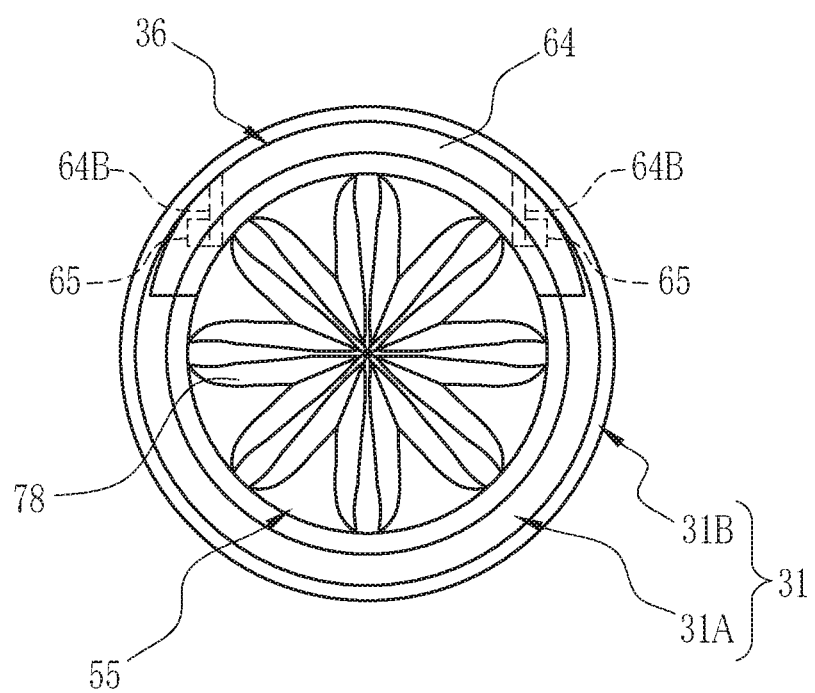
FIG. 25 is an explanatory view showing a modified example of the ridge section.

FIG. 25 shows an example in which eight ridge sections 78 are provided. Two of these are arranged at positions corresponding to the hinge sections of the camera section 36, as same as the ridge sections 78A and 78B shown in FIG. 23A. Further, as in the examples of providing the four ridge sections 78 shown in FIGS. 23A and 23B and providing the eight ridge sections 78 shown in FIG. 25, the arrangement intervals of the plurality of ridge sections 78 are preferably equal. This is because it is considered that the effect of preventing wrapping of the fat 23A by providing a plurality of ridge sections 78 can be equally obtained in the circumferential direction of the puncture member 55, when the arrangement intervals are equal.

[Airtight Structure Unit]

Figure 26:
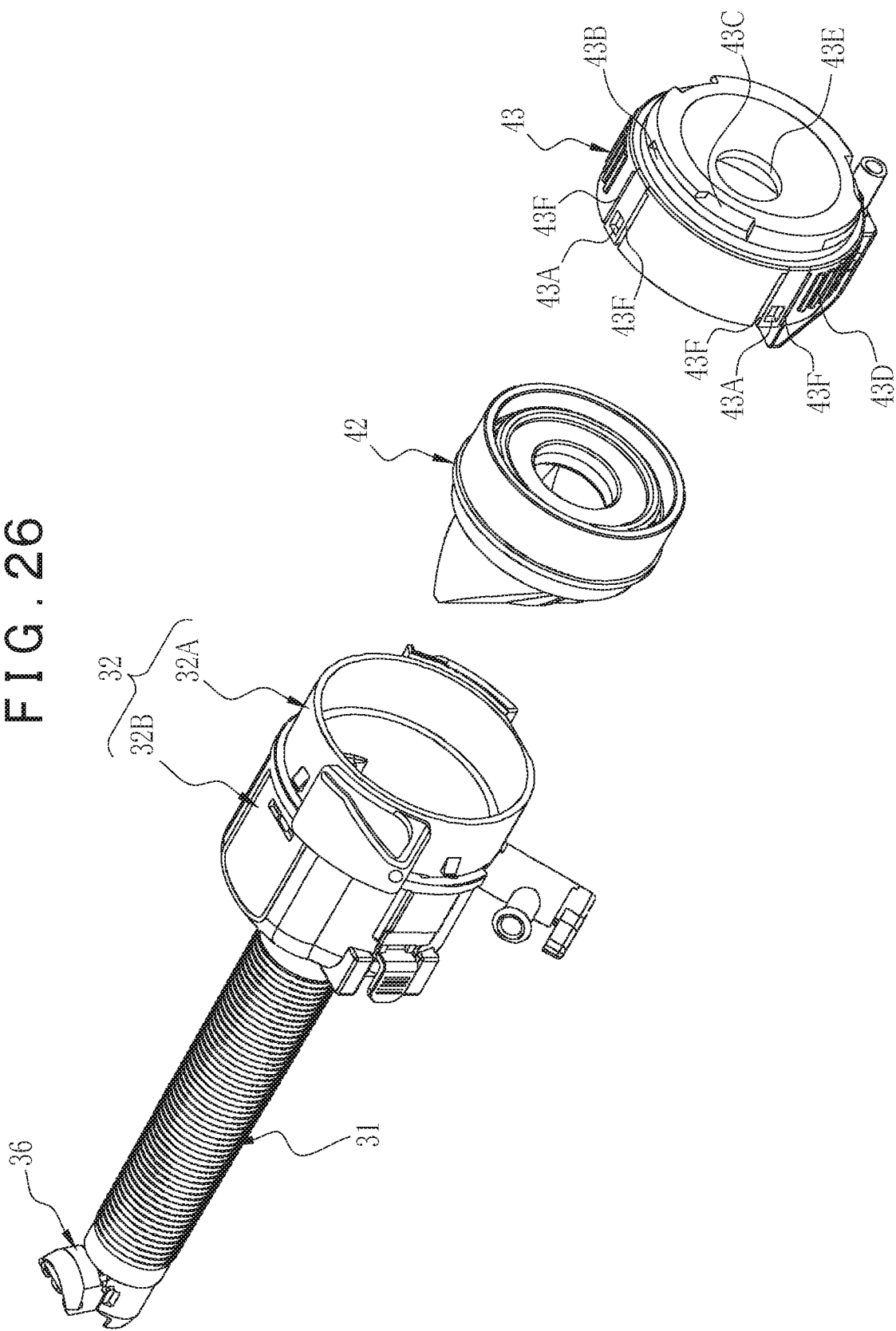
FIG. 26 is a rear perspective view of an airtight structure unit.

FIG. 26 is a perspective view of the airtight structure unit 42 shown in FIG. 7 as viewed from the proximal side. As described above, the airtight structure unit 42 has the function of preventing gas leakage from the inside of the abdominal cavity to the outside of the body. The airtight structure unit 42 is accommodated in the head section inner sleeve 32A, and the rear opening portion of the head section inner sleeve 32A is closed by the rear cover 43.

Figure 27:
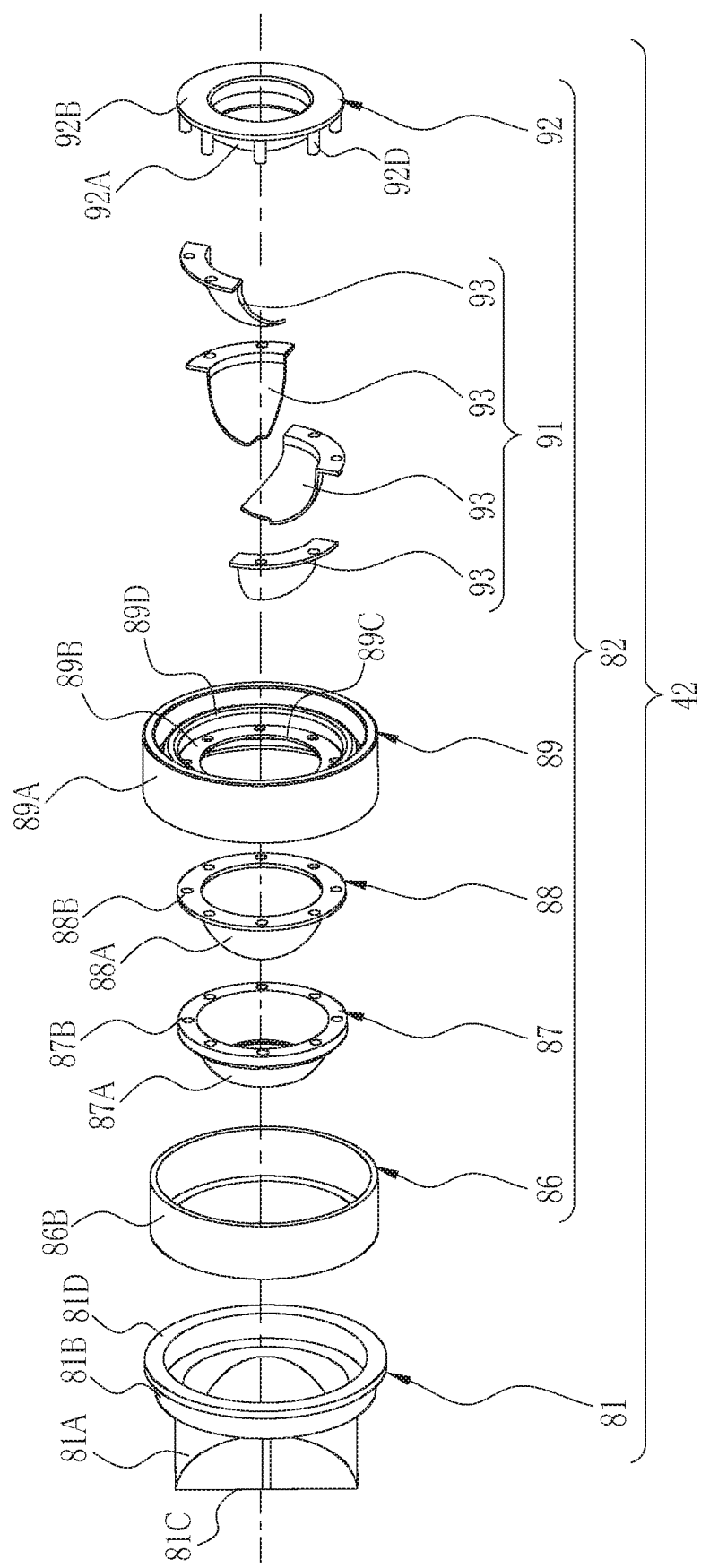
FIG. 27 is an exploded perspective view of the airtight structure unit.
Figure 28:
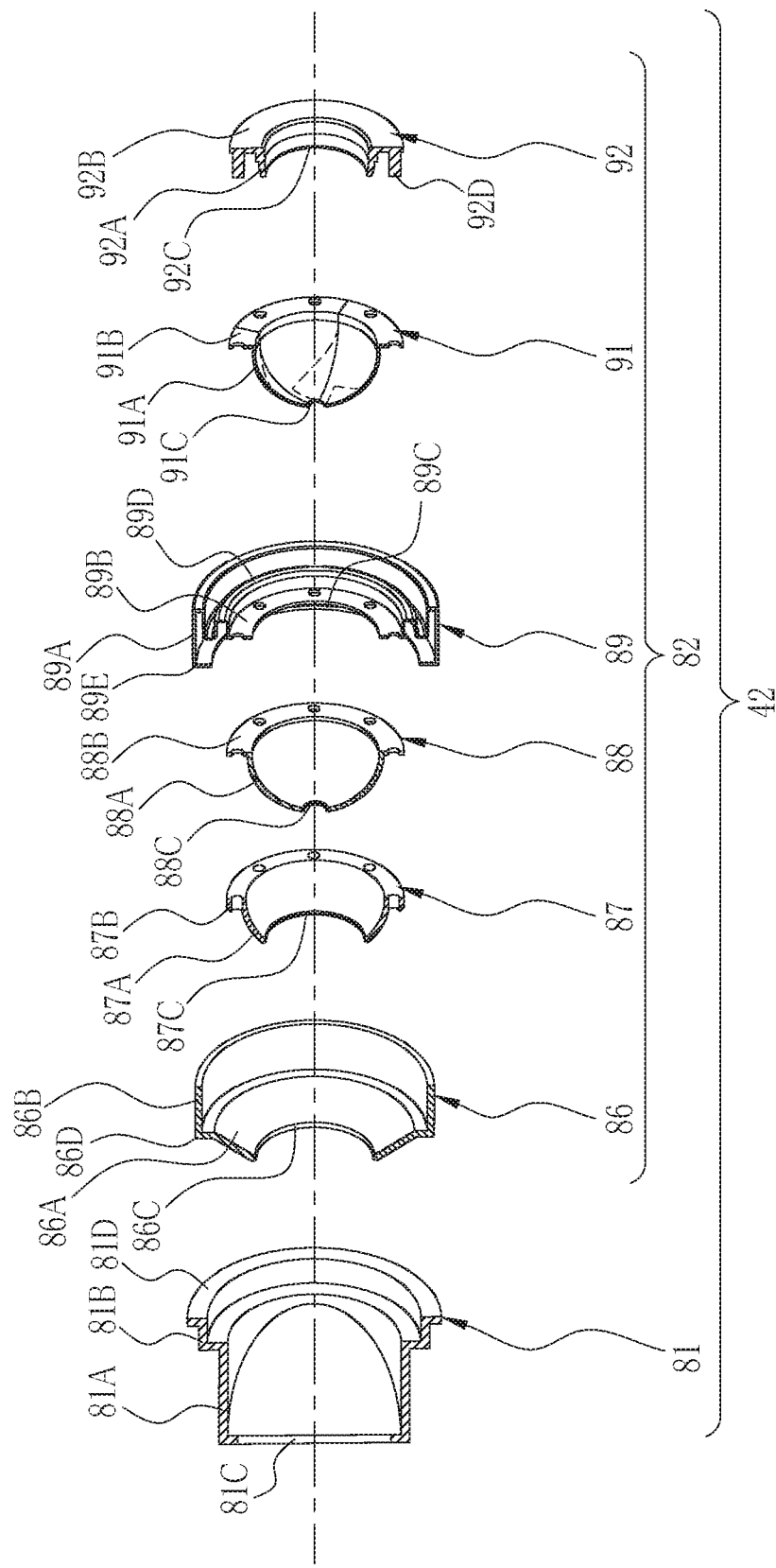
FIG. 28 is an exploded perspective view (cross-sectional view) of the airtight structure unit.

As shown in FIGS. 27 and 28, the airtight structure unit 42 is configured of a duckbill valve 81 and a seal unit 82 disposed on the proximal side of the duckbill valve 81. The duckbill valve 81 prevents gas from leaking out of the insufflated body cavity through the insertion hole 33 when the treatment tool 22 is not inserted into the trocar with camera 16. On the other hand, the seal unit 82 prevents gas from leaking out of the body cavity through the insertion hole 33 in the state where the treatment tool 22 is inserted.

(Configuration of Duckbill Valve)

The duckbill valve 81 is a valve mechanism shaped like a duck bill as well known, and has a valve section 81A and a circular section 81B integrally formed at the proximal end of the valve section 81A. The duckbill valve 81 is formed of an elastomer such as silicone rubber. The valve section 81A has two opposite slopes intersecting at the distal end and extending toward the proximal end. At the distal end of the valve section 81A, a linear opening 81C is formed. At the proximal end of the circular section 81B, a flange 81D that protrudes outward is formed (see also FIG. 4).

Figure 30:
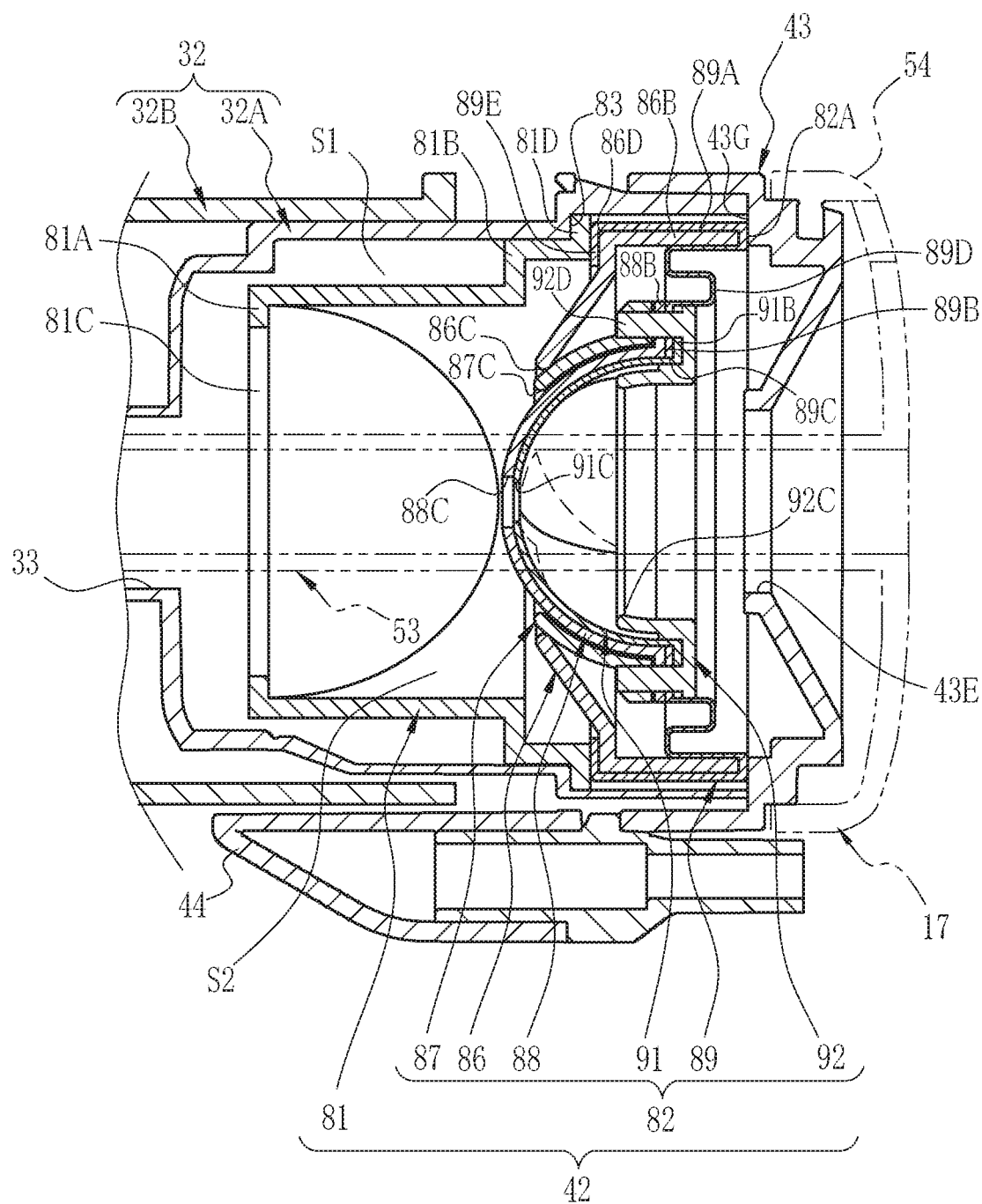
FIG. 30 is a cross-sectional view of a head section in which the airtight structure unit is accommodated.

As shown in a sectional view of FIG. 30, on the inner wall surface of the head section inner sleeve 32A to which the airtight structure unit 42 is attached, provided is an abutment surface 83 which abuts the flange 81D of the duckbill valve 81. In the head section inner sleeve 32A, the inner diameter on the distal side of the abutment surface 83 is substantially the same as the outer diameter of the circular section 81B of the duckbill valve 81.

(Configuration of Seal Unit)

As shown in FIGS. 27 and 28, the seal unit 82 includes a seal holder 86, a first mount 87, a dome type seal 88, an airtight rubber cover 89, a centering guide 91, and a second mount 92. These members are disposed in this order from the distal end side to the proximal end side with the seal holder 86 at the top, and are united as the seal unit 82.

The dome type seal 88 is a member having a circular planar shape and having a convex dome shape toward the distal end side. The dome type seal 88 has a dome-shaped seal section 88A and a circular flange 88B formed on the outer periphery of the seal section 88A. At the radial center of the seal section 88A, that is, at the central portion located at the apex of the dome shape, formed is an opening 88C through which the treatment tool 22 and the trocar shaft 17 are inserted. The dome type seal 88 is made of a single piece of material having a circular planar shape, and the material is silicone rubber. The opening 88C expands by elastic deformation, with being in close contact with the outer peripheral surface of the treatment tool 22 being inserted therein. The outer peripheral surface of the treatment tool 22 and the inner circumference of the opening 88C are airtightly sealed. Thereby, the gas leakage from the opening 88C is prevented in the state where the treatment tool 22 is inserted.

The diameter of the opening 88C of the dome type seal 88 is determined according to the outer diameter of the treatment tool 22 to be inserted. The outer diameter of a typical treatment tool 22 is about 5 mm. Therefore, in this embodiment, the diameter of the opening 88C is set to 4 mm, which is slightly smaller than the outer diameter of the treatment tool 22. Accordingly, as the treatment tool 22 is inserted, the opening 88C is expanded by elastic deformation so that the inner periphery of the opening 88C and the outer periphery of the treatment tool 22 can be closely attached.

The silicone rubber used in the dome type seal 88 is a silicone rubber having a JIS A hardness of 30 according to durometer measurement, and is a relatively flexible material having a thickness of about 0.8 mm. By using a flexible material, the good operability of the treatment tool 22 is ensured.

Figure 29:
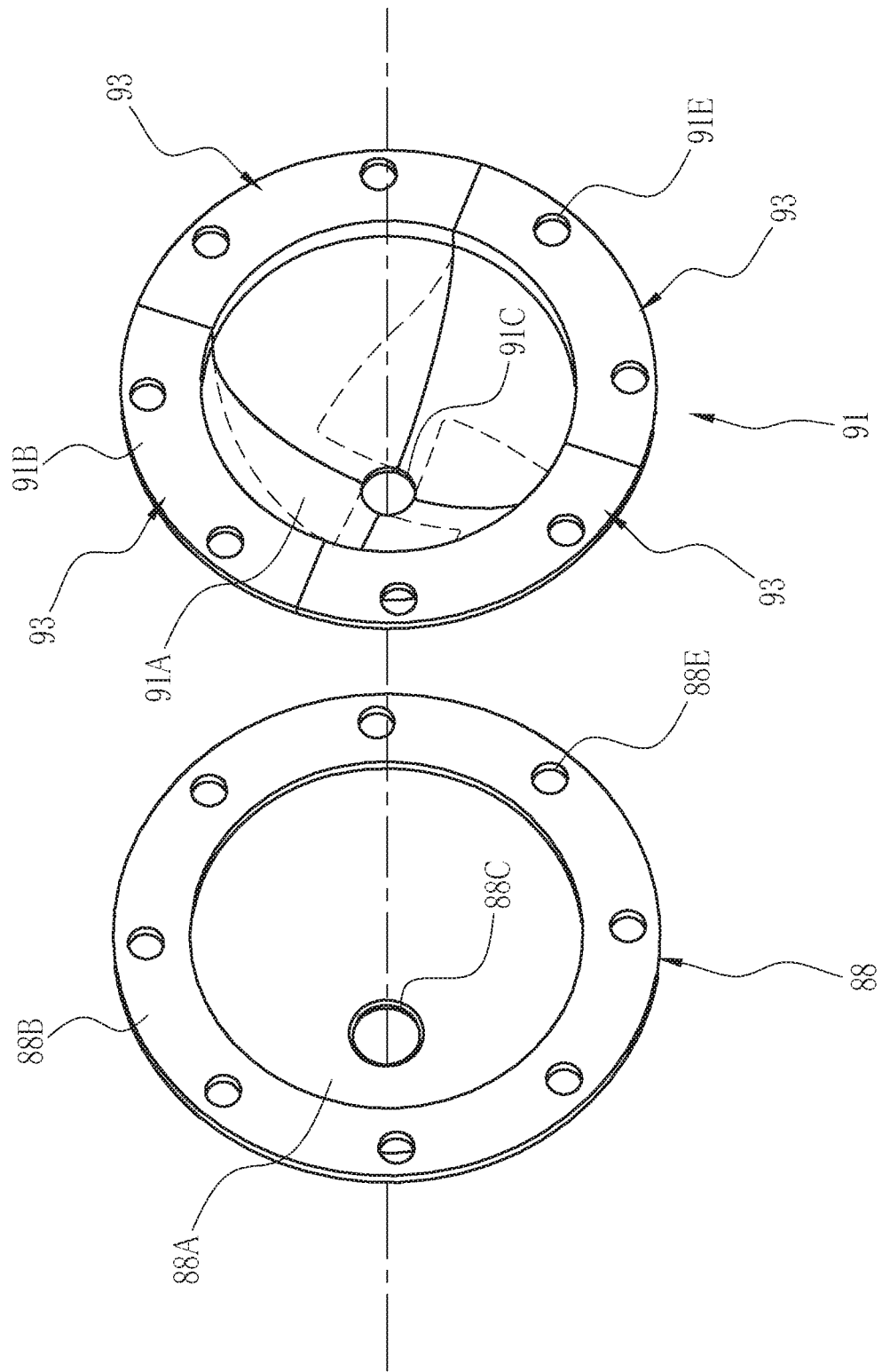
FIG. 29 is a perspective view of a dome type seal and a centering guide.

As also shown in FIG. 29, the centering guide 91 is disposed behind the dome type seal 88 (proximal side of the trocar with camera 16). The centering guide 91 is composed of four segments 93. The centering guide 91 is configured to have a convex dome shape toward the distal end side as a whole by combining the segments 93. In the each segment 93, the adjacent segments 93 are partially overlapped.

The overall shape of the centering guide 91 corresponds to the shape of the dome type seal 88. The centering guide 91 has a dome-shaped guide section 91A and a flange 91B formed on the outer periphery of the guide section 91A. In the central portion corresponding to the apex of the dome shape of the guide section 91A, formed is an opening 91C through which the treatment tool 22 and the trocar shaft 17 are inserted. The diameter of the opening 91C is the same as or slightly smaller than the opening 88C of the dome type seal 88. In this embodiment, it is 4 mm, the same as the opening 88C. The material of the centering guide 91 is polyurethane having a JIS A hardness of 90 according to durometer measurement, and has a thickness of about 0.5 mm.

Figure 31A:
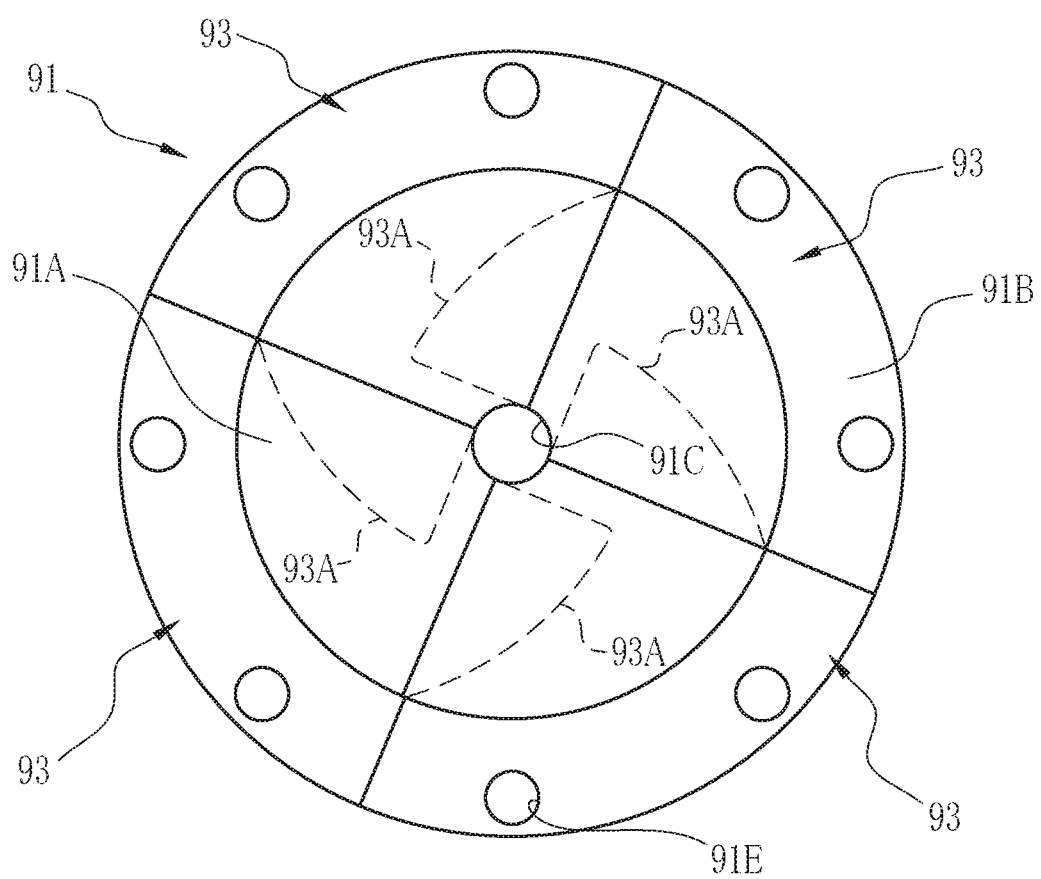
FIG. 31A is a rear view of a centering guide.
Figure 31B:
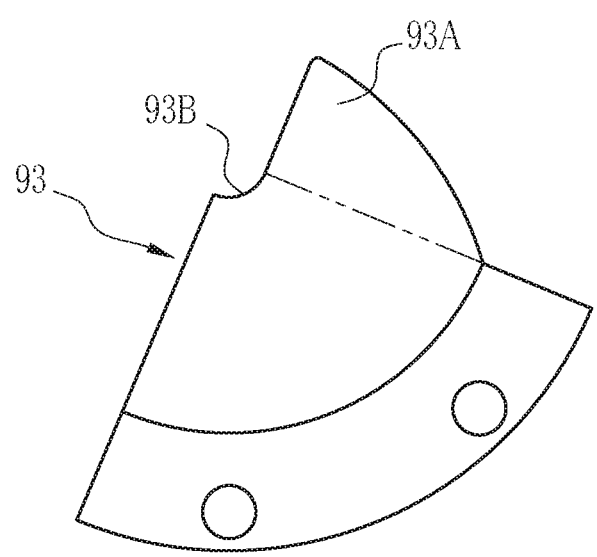
FIG. 31B is an explanatory diagram of a segment of the centering guide.

In FIG. 29, FIG. 31A, and FIG. 31B which show a state where the centering guide 91 is viewed from the proximal end side, the four segments 93 constituting the centering guide 91 are substantially fan-shaped, and the length of the arc is ¼ of the circumference of the centering guide 91. Here, the expression "¼ of the circumference" includes a margin of plus or minus 10%.

In addition, the area of overlapping region 93A where the adjacent segments 93 overlap is half or less of the total area of the segments 93. Further, as shown in FIGS. 31A and 31B, the overlapping region 93A has a shape in which the width of the overlapping region 93A monotonously increases from the outer periphery toward the center of the centering guide 91.

In each of the segments 93, a cutout 93B that is a part of the opening 91C is formed. Further, in the overlapping region 93A, the edge on the opening 91C side is smoothly connected to the cutout 93B. In addition, the edge on the opening 91C side extends in a direction parallel to the radial direction of the centering guide 91.

When the treatment tool 22 is inserted, the opening 91C expands in accordance with the outer diameter of the treatment tool. This expansion is performed by displacing the adjacent segments 93 in a direction in which they are separated. The opening 91C is composed of the cutouts 93B of the each segment 93, and the adjacent segments 93 have the overlapping region 93A. Therefore, even when the opening 91C is expanded, the overlap between the adjacent segments 93 is maintained, so that a gap is hardly generated between the opening 91C and the outer periphery of the treatment tool 22.

The centering guide 91 guides the distal end of the treatment tool 22 to the opening 88C at the center of the dome type seal 88 by the guide section 91A and the opening 91C when the treatment tool 22 is inserted.

The first mount 87 has an opening 87C disposed on the distal end side of the dome type seal 88 and exposing the seal section 88A, and has a mount section 87A with a convex shape projecting toward the distal end side and a flange 87B formed on the outer periphery of the mount section 87A. The first mount 87 is formed of, for example, a resin material such as polyester. The first mount 87 supports the distal end side of the seal section 88A of the dome type seal 88 by the mount section 87A, and supports the flange 88B from the distal end side by the flange 87B. The diameter of the opening 87C is larger than the diameter of the trocar shaft 17 and the treatment tool 22, so that these can be inserted to the opening.

The seal holder 86 has an opening 86C that exposes the seal section 88A of the dome type seal 88, and has a substantially conical cover section 86A with a convex shape projecting toward the distal end side and a cylinder section 86B formed on the proximal side of the cover section 86A. The diameter of the opening 86C of the seal holder 86 is slightly larger than the diameter of the opening 87C of the first mount 87. The seal holder 86 is formed of, for example, a resin material such as polyester.

The cover section 86A supports and covers the periphery of the mount section 87A of the first mount 87, that exposes the seal section 88A of the dome type seal 88, from the distal end side. When the dome type seal 88 and the mount section 87A move to the distal end side in accordance with the operation of the treatment tool 22, the cover section 86A functions as an abutment member for the mount section 87A to restrict the movement amount toward the distal end side.

The cylinder section 86B functions as a frame to which the airtight rubber cover 89 is attached. The inside diameter of the cylinder section 86B is large enough to accommodate the first mount 87, the dome type seal 88, the centering guide 91, and the second mount 92 inside. In the cylinder section 86B, a distal peripheral edge 86D (see FIG. 30) located around the cover section 86A functions as an abutment surface for the flange 81D of the duckbill valve 81 via the airtight rubber cover 89.

The second mount 92 is disposed on the proximal side of the centering guide 91. The second mount 92 has a mount section 92A with a convex shape projecting toward the distal end side and a flange 92B formed on the outer periphery of the mount section 92A. The second mount 92 is formed of, for example, a resin material such as polyester. The second mount 92 supports the proximal side of the guide section 91A of the centering guide 91 by the mount section 92A, and supports the flange 91B from the proximal side by the flange 92B. An opening 92C is formed in the mount section 92A. The opening 92C has almost the same diameter as the opening 87C of the first mount 87, so that the trocar shaft 17 and the treatment tool 22 can be inserted therein.

The flange 92B is formed with a plurality of pins 92D projecting toward the distal end side. The pins 92D are equally spaced on the circumference of the flange 92B. The plurality of pins 92D are inserted into small holes 91E (see FIG. 29) of the flange 91B of the centering guide 91, small holes 88E (see FIG. 29) of the flange 88B of the dome type seal 88, and small holes of the flange 87B of the first mount 87. As a result, the centering guide 91, the dome type seal 88, the first mount 87, and the second mount 92 are assembled together as shown in FIG. 30.

The pin 92D is caulked, for example, by heat welding such as ultrasonic welding in a state where the pin 92D is inserted into the small holes 91E, 88E, and so on. As a result, the flange 87B of the first mount 87, the flange 88B of the dome type seal 88, and the flanges of the second mount 92 and the centering guide 91 are fixed in a close contact state. Since the pin 92D is provided on the second mount 92 and protrudes to the distal end side, the distal end side of the caulked pin 92D is not visible from the proximal end side of the airtight structure unit 42. Accordingly, the appearance is improved.

The airtight rubber cover 89 has a cylinder section 89A with a cylindrical shape and an inner flange 89B provided inside the cylinder section 89A. The inner flange 89B is formed with an opening 89C through which the trocar shaft 17 and the treatment tool 22 are inserted. Further, a bellows portion 89D is provided between the cylinder section 89A and the inner flange 89B. The airtight rubber cover 89 is formed of an elastomer such as silicone rubber having a HS A hardness of 30 according to durometer measurement. The hardness of the airtight rubber cover 89 is as soft as the dome type seal 88. In addition, in the airtight rubber cover 89, the bellows portion 89D is formed thinner than other portions such as the cylinder section 89A and a folded portion 89E. The bellows portion 89D has the thickness of 0.3 mm and the other parts have the thickness of 0.5 mm.

The inner flange 89B also has small holes into which the pins 92D of the second mount 92 are inserted. As shown in FIG. 30, by inserting the pins 92D into the small holes, the inner flange 89B is sandwiched between the flange 88B of the dome type seal 88 and the flange 91B of the centering guide 91. As a result, the first mount 87, the dome type seal 88, the centering guide 91, and the second mount 92 are attached to the airtight rubber cover 89. Further, since the bellows portion 89D elastically deforms and stretches, the dome type seal 88, the centering guide 91 and the like are movably supported inside the airtight rubber cover 89. The bellows portion 89D allows radial movement of the dome type seal 88 and the centering guide 91.

The cylinder section 89A of the airtight rubber cover 89 is attached so as to cover the outer peripheral surface of the cylinder section 86B of the seal holder 86. The folded portion 89E folded inward is provided at the periphery of the distal end side of the cylinder section 89A, and the folded portion 89E is put on the peripheral edge 86D of the cylinder section 86B of the seal holder 86.

(Assembling of Seal Unit)

Assembling of the seal unit 82 is performed, for example, as follows. First, the segments 93 are superimposed to form the centering guide 91, and the centering guide 91 is attached to the second mount 92 by inserting the pins 92D into the small holes 91E of the flange 91B.

Next, the second mount 92 with the centering guide 91 attached is attached to the airtight rubber cover 89 by inserting the pins 92D into the small holes of the inner flange 89B. The pins 92D protrude from the small holes of the inner flange 89B of the airtight rubber cover 89. In this state, the flange 88B of the dome type seal 88 and the flange 87B of the first mount 87 are sequentially attached from the distal end side to the pins 92D protruding from the inner flange 89B of the airtight rubber cover 89. After these mountings are completed, the pins 92D are caulked.

Finally, the airtight rubber cover 89 is applied from the proximal side of the seal holder 86. The cylinder section 89A is attached to the outer periphery of the cylinder section 86B, and the peripheral edge 86D is covered with the folded portion 89E. The first mount 87, the dome type seal 88, the centering guide 91, and the second mount 92, which are fixed to the inner flange 89B, are accommodated inside the seal holder 86. As a result, the seal holder 86, the first mount 87, the dome type seal 88, the centering guide 91, the second mount 92, and the airtight rubber cover 89 are integrated to complete the seal unit 82.

(Attachment of the Airtight Structure Unit to the Head Section)

As shown in the sectional view of FIG. 30, the duckbill valve 81 is mounted such that the outer peripheral surface of the circular section 81B is in pressure contact with the inner wall of the head section inner sleeve 32A, and the flange 81D is pushed distally until it abuts the abutment surface 83.

As the duckbill valve 81 is mounted, an internal space S1 is formed in the head section inner sleeve 32A by the outer peripheral surface of the duckbill valve 81 and the inner peripheral surface of the head section inner sleeve 32A. The internal space S1 communicates with the insertion hole 33 of the pipe section inner sleeve 31A, and the connection port 49 to which carbon dioxide is supplied is also connected to the internal space S1.

After the duckbill valve 81 is attached, the seal unit 82 is attached to the proximal end side of the duckbill valve 81. The seal unit 82 is attached in a state where the folded portion 89E of the airtight rubber cover 89 which covers the peripheral edge 86D of the seal holder 86 is in contact with the proximal end of the flange 81D of the duckbill valve 81. After the seal unit 82 is attached, the rear cover 43 is attached from the proximal end side of the seal unit 82.

When the rear cover 43 is attached to the head section inner sleeve 32A, the seal unit 82 receives the pressure from the rear cover 43, and the duckbill valve 81 is pushed toward the distal end side. As a result, the flange 81D of the duckbill valve 81 is pressed to the abutment surface 83. In addition, the outer peripheral surface of the duckbill valve 81 and the inner wall of the head section inner sleeve 32A are hermetically sealed. Thereby, the internal space S1 is hermetically sealed.

Also, as the rear cover 43 is attached, the abutment surface 43G on the distal side of the rear cover 43 is in pressure contact with a peripheral edge 82A on the proximal side of the seal unit 82 covered by the airtight rubber cover 89. In the distal end side of the seal unit 82, the folded portion 89E is in pressure contact with the flange 81D of the duckbill valve 81. By this pressure contact, in an internal space S2 of the duckbill valve 81, the proximal end side peripheral portion of the duckbill valve 81 is sealed. Further, by the attachment of the rear cover 43, the seal unit 82 is held between the duckbill valve 81 in the distal end side and the rear cover 43 in the proximal end side so as not to move in the Z-axis direction.

In addition, in the seal unit 82, the inner flange 89B of the airtight rubber cover 89 and the flange 88B of the dome type seal 88 are in pressure contact and sealed airtightly by caulking of the pin 92D. Therefore, when the treatment tool 22 is inserted through the opening 88C of the dome type seal 88, the internal space S2 of the duckbill valve 81 is airtightly sealed.

(Functions of Airtight Structure Unit)

When trocar with camera 16 is inserted into the body cavity and insufflation is performed by supply of carbon dioxide gas, the pressure in the internal space S1 increases, and pressure in the direction to block the opening 81C works on the two slopes of the valve section 81A of the duckbill valve 81. When the treatment tool 22 is not inserted into the opening 81C, the opening 81C is hermetically sealed by the air pressure. Also, the duckbill valve 81 is airtightly attached to the pipe section inner sleeve 31A. Therefore, when the treatment tool 22 is not inserted into the opening 81C, gas leakage from the internal space S1 to the outside of the body is prevented.

When the trocar shaft 17 or the treatment tool 22 is inserted into the opening 88C of the dome type seal 88 or the like, the opening 88C spreads due to elasticity and closely contacts the outer peripheral surface of the trocar shaft 17 or the treatment tool 22. On the other hand, the opening 81C of the duckbill valve 81 opens when the trocar shaft 17 or the treatment tool 22 is inserted thereto. Since the opening 81C is a linear opening, when the opening 81C is opened, a gap is generated between the opening 81C and the outer peripheral surface of the trocar shaft 17 or the treatment tool 22, and the seal is released.

However, when the trocar shaft 17 or the treatment tool 22 is inserted, the proximal end side of the internal space S2 in the duckbill valve 81 is sealed by the seal unit 82 including the dome type seal 88. For this reason, even if the opening 81C of the duckbill valve 81 is opened by the trocar shaft 17 or the treatment tool 22 being inserted, it is possible to prevent the gas from leaking out of the body cavity through the insertion hole 33.

The seal unit 82 improves the air tightness by using the one-piece dome type seal 88 having the opening 88C, as compared with a conventional seal in which a seal is constituted of a plurality of segments, because the seal unit 82 has no gap which would be caused between such segments.

Further, on the proximal side of the dome type seal 88, disposed is the centering guide 91 having hardness higher than that of the dome type seal 88 and having the opening 91C. Therefore, when the treatment tool 22 is inserted into the trocar with camera 16, it is easy to guide the treatment tool 22 to the position of the opening 88C at the center of the dome type seal 88. This is because the treatment tool 22 will be guided to the position of the opening 88C of the dome type seal 88 by abutting the treatment tool 22 to the proximal end side of the centering guide 91 and detecting the position of the opening 91C with a tactile sense. The opening position can be easily found as compared with a conventional case where a protector having no opening is disposed on the proximal end side of a seal. In addition, since the hardness of the centering guide 91 is higher than that of the dome type seal 88, the frictional resistance of the treatment tool 22 is reduced, which facilitates guiding.

In this embodiment, the seal unit 82 uses the dome type seal 88, the centering guide 91 composed of the plurality of segments 93, and the airtight rubber cover 89 in combination. Further, the hardness of each of the dome type seal 88 and the airtight rubber cover 89 is lower than the hardness of the centering guide 91. Therefore, as described below, even if a radial force acts on the opening 88C of the dome type seal 88 by the movement of the treatment tool 22, the deformation of the opening 88C is prevented. As the deformation of the opening 88C is prevented, a gap does not easily occur between the opening 88C and the outer peripheral surface of the treatment tool 22, so that good sealing performance can be ensured.

Figure 32A:
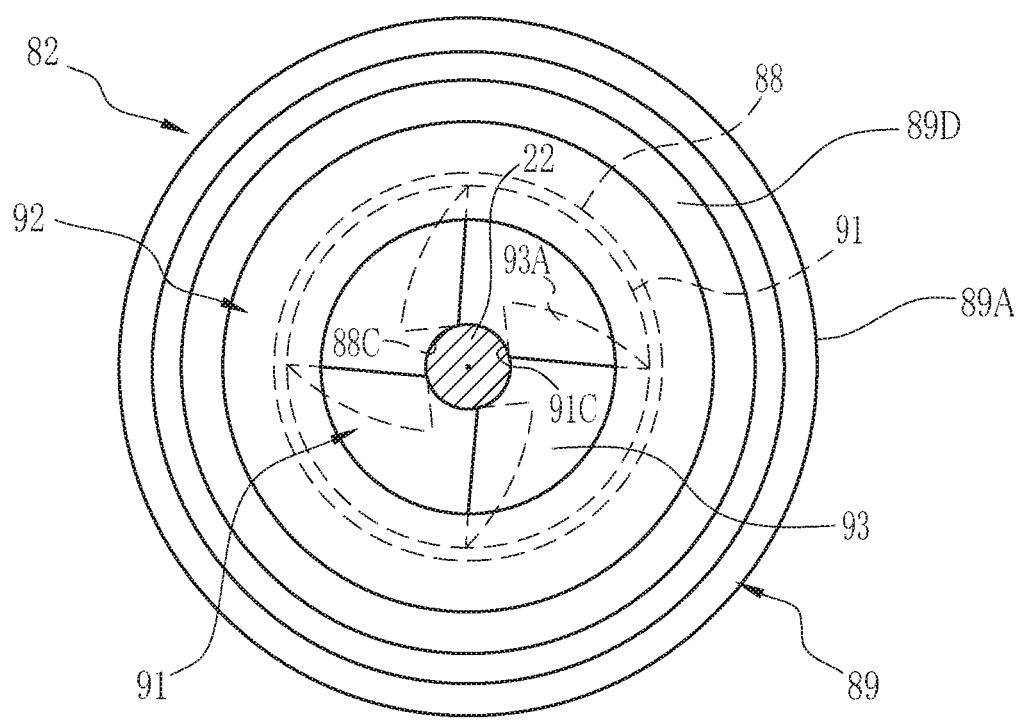
FIG. 32A is a rear view of a seal unit in a state where a treatment tool is inserted.
Figure 32B:
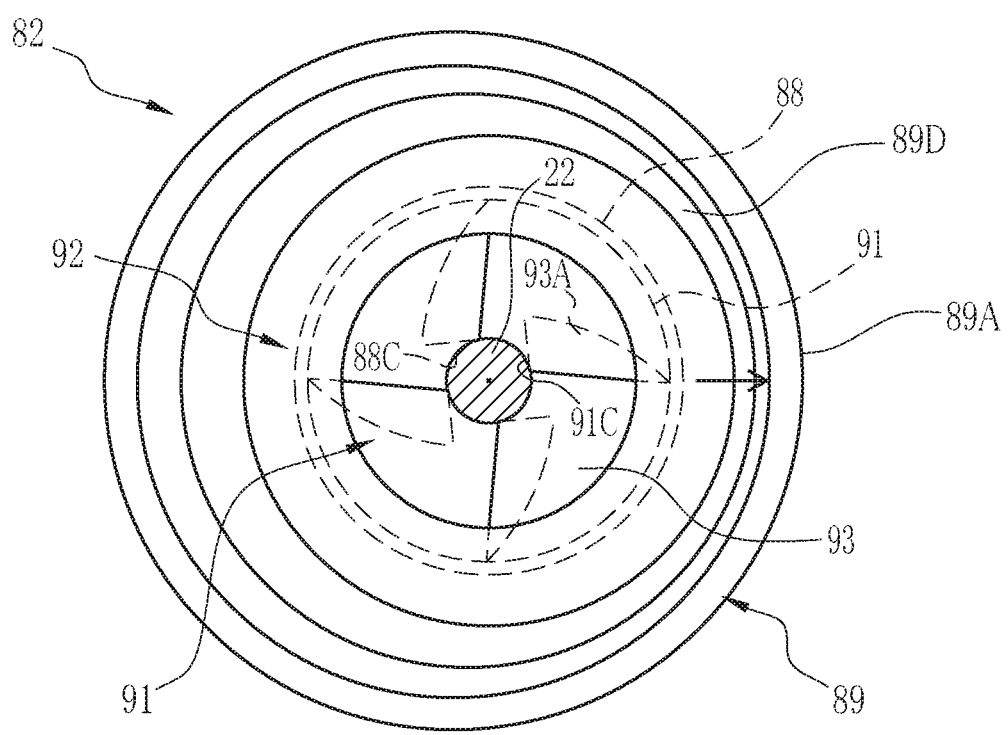
FIG. 32B is a rear view of the seal unit in a state where the inserted treatment tool is moved in a radial direction.

FIGS. 32A and 32B are views of the seal unit 82 in a state where the treatment tool 22 has been inserted, as viewed from the proximal side. FIG. 32A shows a state in which the treatment tool 22 is at the radial center of the seal unit 82, and FIG. 32B shows a state in which the treatment tool 22 has moved in the radial direction of the seal unit 82, that is, toward the right in the figure, from the state in FIG. 32A.

When the treatment tool 22 is inserted, the opening 88C of the dome type seal 88 and the opening 91C of the centering guide 91 expand according to the outer diameter of the treatment tool 22. As shown in FIG. 32A, in the state where the treatment tool 22 is at the center, the bellows portion 89D of the airtight rubber cover 89 maintains the initial state where the distance to the cylinder section 89A is uniform over the entire circumference.

When the treatment tool 22 is operated to move in the radial direction (to the right side in the figure) as shown in FIG. 32B, a force acts in a direction to expand the opening 91C of the centering guide 91. In order for the opening 91C to expand, the adjacent segments 93 must move in a direction away from each other, but a frictional resistance is generated due to the contact in the overlapping region 93A. The frictional resistance against the force for expanding the opening 91C is larger than the resistance against the force for expanding the opening 88C of the dome type seal 88 and the resistance against the force for elastically deforming the bellows part 89D of the airtight rubber cover 89.

Therefore, the bellows portion 89D elastically deforms earlier than the opening 91C expands. When the bellows portion 89D is elastically deformed, the centering guide 91 and the dome type seal 88 held on the inner flange 89B of the airtight rubber cover 89 move in the radial direction as a whole. As a result, the force for expanding the opening 88C of the dome type seal 88 is also reduced, so that the deformation of the opening 88C is prevented.

Also, by making the shape of segments 93 constituting the centering guide 91 into the fan shape having the arc whose length is ¼ of the circumference of the centering guide 91, the overlapping amount of the adjacent segments 93 is reduced as compared with a prior art using a protector formed of semicircular segments. This improves the smoothness of the insertion and removal of the treatment tool 22 with respect to the opening 91C. In addition, by setting the area of the overlapping region to be half or less of the total area of the segment, the amount of overlap is reduced compared to the prior art, and the smoothness is further improved.

Further, the overlapping region 93A between the adjacent segments 93 has the shape in which the overlapping width monotonously increases from the outer periphery toward the opening 91C at the center, thereby further improving the smoothness of insertion and extraction of the treatment tool 22 with respect to the opening 91C. Since the treatment tool 22 is inserted near the center where the opening 91C is located, the adjacent segments 93 are easy to be separated. On the other hand, as it gets closer to the outer circumference, it gets farther from the treatment tool 22 near the center, so that the amount of separation between the adjacent segments 93 decreases.

As described above, considering the smoothness of insertion and extraction of the treatment tool 22, it is better for the overlapping region 93A to be smaller. By making the overlapping width of the overlapping region 93A monotonously increase from the outer periphery toward the opening 91C at the center, the width of the overlapping region 93A can be minimized while preventing the formation of a gap between the adjacent segments 93.

[White Balance for Trocar Image or Endoscopic Image]

Figure 33:
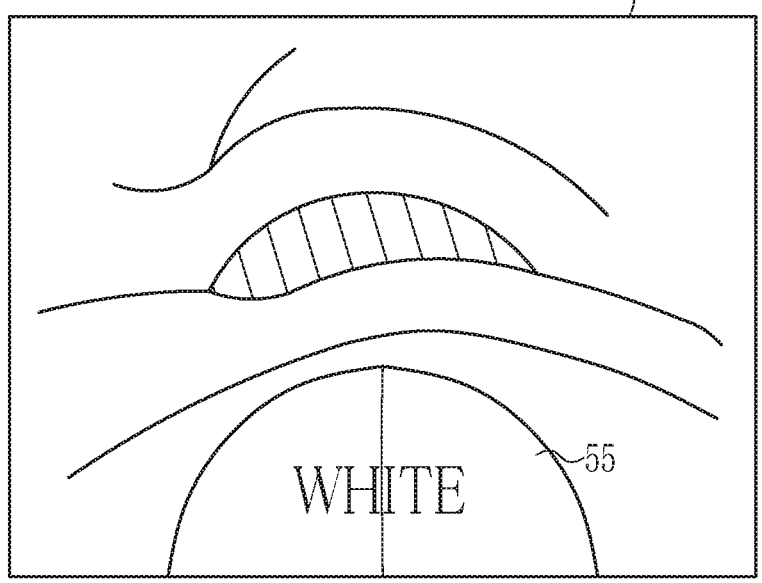
FIG. 33 is an image diagram showing a trocar image for white balance setting including an image of a white part of the puncture member.

In the trocar apparatus with camera 12, as shown in FIG. 33, by forming a white part 94 on the surface of the puncture member 55 of the trocar shaft 17 which is to be inserted into the abdominal cavity, it is possible to set a white balance for trocar images inside the body cavity. To perform the white balance for trocar images, after popping up the camera section 36 to the deployed position in the abdominal cavity, the white part 94 formed on the surface of the puncture member 55 is entered in the field of view of the camera section 36, and the white part 94 is illuminated with the illumination light from the endoscope 11. In this state, the white balance setting switch 12a provided in the trocar apparatus with camera 12 is operated. As a result, a trocar image for setting the white balance including the image of the white part 94 is obtained. Note that the white balance setting switch 12a may be provided on the console 20. Also, the white part 94 may be provided on the entire of the puncture member 55 or may be provided in a part of the puncture member 55.

Figure 34:
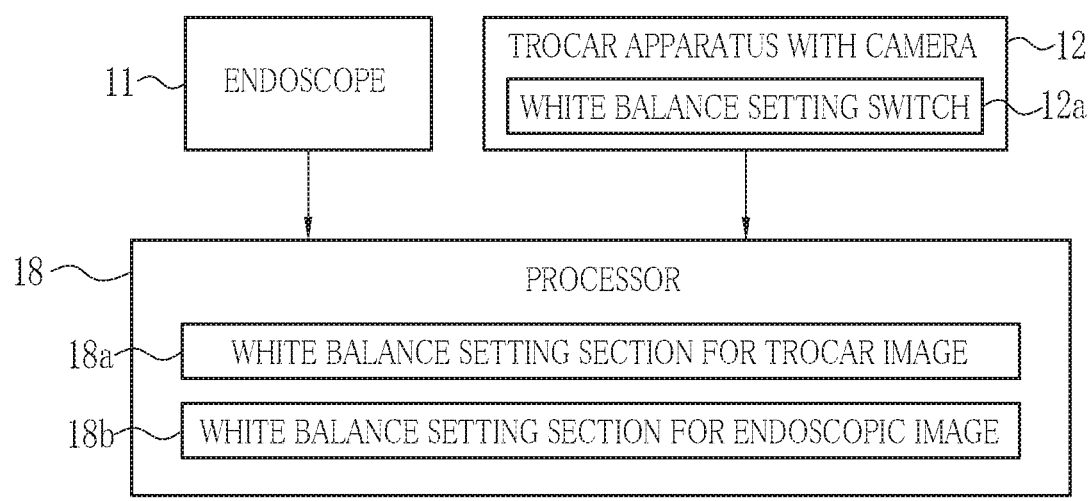
FIG. 34 is a block diagram showing functions of a processor having a white balance setting section for trocar image and a white balance setting section for endoscopic image.

As shown in FIG. 34, the trocar image for setting the white balance is sent to a white balance setting section for trocar image 18a provided in the processor 18. The white balance setting section for trocar image 18a sets the white balance for trocar images based on the trocar image for white balance setting. Specifically, the white balance setting section for trocar image 18a identifies a specific region in a lower part of the image as the image region of the white part 94, from the trocar image for setting the white balance, and performs the white balance setting based on the image in this specific region. Here, since the positional relationship between the camera section 36 and the white part 94 when the camera section 36 is set to the deployed position is known in advance, the specific region is preset based on this positional relationship. Note that it is known that the puncture member 55 occupies about 10% of the area of the trocar image for setting the white balance.

For the image in the specific region of the trocar image for setting white balance, a gain coefficient Gb of the B image signal, a gain coefficient Gg of the G image signal, and a gain coefficient Gr of the R image signal are set such that the ratio of the signal values of the B image signal, the G image signal and the R image signal becomes 1:1:1. This completes the setting of the white balance for trocar images. After setting the white balance, a white object will be displayed in white on the monitor 19 by multiplying the trocar image obtained from the camera section 36 by the gain coefficients Gb, Gg, and Gr.

The processor 18 is also provided with a white balance setting section for endoscopic image 18b that sets a white balance for endoscopic images. The white balance for endoscopic images may be made before inserting the endoscope 11 into the body cavity, or may be made substantially the same as the white balance for trocar images after setting the white balance for trocar images. When the white balance for endoscopic images is made substantially the same as the white balance for trocar images, for example, the gain coefficients Gb, Gg, and Gr for the trocar image set in the white balance setting section for trocar image 18a are sent to the white balance setting section for endoscopic image 18b. The white balance setting section for endoscopic image 18b sets the received gain coefficients Gb, Gg, and Gr as the gain coefficients to be used for the white balance for endoscopic images. A white object in the endoscopic image is displayed in white on the monitor 19 by multiplying the endoscopic image by the set gain coefficients Gb, Gg, and Gr.

Figure 35:
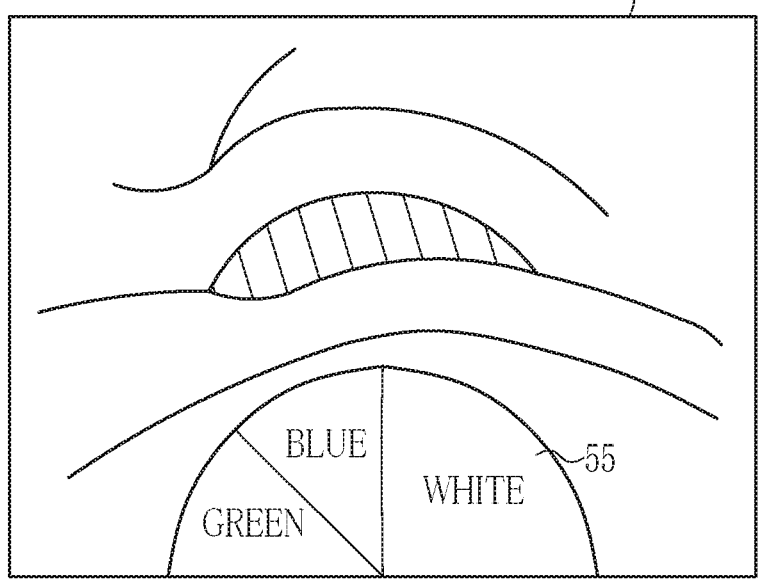
FIG. 35 is an image diagram showing a trocar image for white balance setting including an image of white, blue, and green parts of the puncture member.

Although the white balance can be performed in the body cavity by forming the white part 94 on the puncture member 55 of the trocar shaft 17, but a part of the puncture member 55 may be a colored part for setting a color balance so that the color balance can be performed in addition to the white balance. For example, since there are few blue and green subjects in the body cavity, as shown in FIG. 35, it is preferable to provide a blue part 95 and a green part 96 in addition to the white part 94 on the puncture member 55 to set the blue and green color balance.

In addition, when using a plurality of trocar apparatuses, the white part 94 should be provided in the puncture member 55 of the trocar shaft 17 of a specific trocar apparatus among the plurality of trocar apparatuses, but it is possible to set the white balance for trocar images even if the puncture member 55 of the trocar shaft 17 of the other trocar apparatus is not provided with the white part 94. In this case, the specific trocar apparatus exposes the white part 94 of the puncture member 55 of the trocar shaft 17 in the body cavity so that the white part 94 becomes in the field of view of the camera section 36 of the trocar apparatus other than the specific trocar apparatus. In this state, the trocar apparatus other than the specific trocar apparatus images the white part 94 of the puncture member 55 of the trocar shaft 17 of the specific trocar apparatus, and performs the white balance setting using the trocar image obtained by this imaging. Note that the specific trocar apparatus may be a cameraless trocar apparatus that does not have the camera section 36 as long as the puncture member 55 of the trocar shaft 17 is provided with the white part 94. This cameraless trocar apparatus is similar to the trocar with camera 16 except that it does not have the camera section 36.

Hereinafter, the operation of the above configuration will be described. When performing laparoscopic surgery, the endoscope 11 and the trocar with camera 16 are connected to the processor 18. After the connection is completed, the processor 18 is activated. Accordingly, driving of the camera unit 28 of the endoscope 11 and the camera unit 62 of the trocar with camera 16 is started for imaging. The image signals from the camera unit 28 and the camera unit 62 are input to the processor 18. The processor 18 performs image processing on the image signals, and displays on the monitor 19 the composite image obtained by combining the endoscopic image and the trocar image.

The medical staff ST performs insertion of the endoscope 11 and the trocars 16 and 17 into the abdominal cavity while confirming the composite image displayed on the monitor 19. First, the three incision parts 26 and 27 are opened in the abdomen of the patient P, for example as shown in FIG. 2. The normal trocar 21 without a camera function is inserted in the middle incision part 26.

On the other hand, the two trocar with camera 16 are inserted in the two incision parts 27. The trocar shaft 17 is mounted to the trocar with camera 16 for the insertion of the trocar with camera 16. For the mounting, as shown in FIGS. 12B and 13B, the outer cylinder member 16B of the trocar with camera 16 is set to the release position in which the camera section 36 is in the deployed position.

The outer cylinder member 16B is locked by the lock releasing member 46 so as not to slide. Therefore, in the holding position, as shown in FIG. 19B, the outer cylinder member 16B is slid to the release position on the proximal side in the state where the lock releasing member 46 is pressed to release the lock. As shown in FIG. 19C, when the engaging projection 46E reaches the engaging groove 47B by sliding the outer cylinder member 16B toward the release position, the engaging projection 46E and the engaging groove 47B are engaged by the action of the spring 68, and the outer cylinder member 16B is locked at the release position.

In this state, the shaft member 53 is inserted from the head section 32 into the insertion hole 33 of the pipe section 31. With the cam pin 59 aligned with the guide groove 52C as shown by the two-dot chain line in FIG. 14, the trocar shaft 17 is advanced distally to engage the cam pin 59 with the guide groove 52C. When the cam pin 59 reaches the second end 52B, the engaging claw 54A shown in FIG. 6 enters the fitting groove 43B from the cutout 43C shown in FIG. 7 to be in the state shown in FIGS. 4, 12B and 13B. This state is the release position of the outer cylinder member 16B, where the camera section 36 is in the deployed position.

When the trocar shaft 17 is rotated toward the initial position, the lock releasing member 46 is pressed to lock the slide of the outer cylinder member 16B. In this state, the handle member 54 of the trocar shaft 17 is rotated. The rotation of the trocar shaft 17 causes the outer cylinder member 16B to slide distally along the Z-axis direction by the action of the cam pin 59 and the cam groove 52. By this slide, the distal end of the pipe section 31 abuts on the camera section 36 at the deployed position from behind, and rotates the camera section 36 toward the storage position. As the outer cylinder member 16B reaches the holding position, the storage of the camera section 36 is completed as shown in FIGS. 3, 12A and 13A.

As described above, since the outer cylinder member 16B is slid by the rotation of the trocar shaft 17, the force acting in directions other than the Z-axis direction is reduced as compared with the case where the pipe section outer sleeve 31B is directly grasped and operated. Therefore, smooth slide operation of the pipe section outer sleeve 31B is possible.

When the trocar shaft 17 is attached to the trocar with camera 16, the puncture member 55 is exposed from the distal end of the pipe section 31. In the insertion of the trocar with camera 16, the puncture member 55 is firstly inserted into the incision part 27. The puncture member 55 enters the body cavity while spreading the abdominal wall 23, and the pipe section 31 enters after the puncture member 55. The puncture member 55 advances while tearing the subcutaneous tissue of the fat 23A.

At this time, the subcutaneous tissue of fat 23A constituting the abdominal wall 23 is wrapped around the puncture member 55 and the pipe section 31. As shown in FIG. 23A, when the trocar shaft 17 is in the initial position and the camera section 36 is in the storage position, the two ridge sections 78 of the puncture member 55 are disposed at the positions corresponding to the hinge sections of the camera section 36. Therefore, as shown in FIGS. 24A and 24B, in the region R1 around the hinge section including the hinge section of the camera section 36 behind the puncture member 55, the wrapping of the fat 23A is suppressed as compared with the other region R2.

After the pipe section 31 of the trocar with camera 16 is inserted to a desired depth in the body cavity, the camera section 36 is deployed. For the deployment, the lock releasing member 46 is pressed to release the slide lock of the outer cylinder member 16B. In this state, the handle member 54 of the trocar shaft 17 is rotated from the initial position to the release completion position. Then, by the actions of the cam pin 59 and the cam groove 52, the outer cylinder member 16B slides proximally from the holding position to the release position. As described above, since the outer cylinder member 16B is slid by rotating the trocar shaft 17, smooth operation is possible. By this slide, the holding of the camera section 36 is released, and the biasing force of the spring 71 causes the camera section 36 to pop up toward the deployed position.

When rotating the trocar shaft 17 toward the release completion position, as shown in FIGS. 15A to 15C, the pressing part 57B provided on the connecting member 57 contacts the camera section 36 and pushes the camera section 36 toward the deployed position. The fat 23A may be attached to the distal end of the pipe section 31 to which the camera section 36 is provided, which may be a resistance against the pop-up of the camera section 36. Even in such a case, the deployment assist mechanism constituted of the connecting member 57 assists the biasing force of the spring 71, so that the deployment by pop-up of the camera section 36 can be reliably performed.

In addition, since the two ridge sections 78A and 78B of the puncture member 55 also suppress the wrapping of the fat 23A on the region R1 around the hinge section of the camera section 36, smooth deployment of the camera section 36 becomes possible.

In the release position where the camera section 36 is in the deployed position, as shown in FIG. 19C, the outer cylinder member 16B engages with the engagement projection 46E and the engaging groove 47B, and is locked not to slide. Therefore, it is prevented that the camera section 36 is stored by a careless slide of the outer cylinder member 16B.

After deploying the camera section 36, the white balance for trocar images is set before removing the trocar shaft 17. The user operates the white balance setting switch 12a so that the camera section 36 captures the trocar image for white balance setting including the white puncture member 55. The white balance setting section for trocar image 18a sets the white balance for trocar images based on the trocar image for white balance setting.

After the setting of the white balance for trocar images is completed, the trocar shaft 17 will be removed from the trocar with camera 16. When the camera section 36 is deployed, the trocar shaft 17 is in the release completion position. In this state, the cam pin 59 has reached the second end 52B as indicated by the two-dot chain line in FIG. 14. Therefore, the trocar shaft 17 can be removed from the trocar with camera 16 while moving the cam pin 59 along the guide groove 52C.

After trocar shaft 17 is removed, carbon dioxide gas is supplied into the body cavity through the connection port 49 and the insertion hole 33 of the trocar with camera 16 to perform the insufflation procedure. When the treatment tool 22 is not inserted into the trocar with camera 16, the internal space S1 (see FIG. 30) communicating with the insertion hole 33 is hermetically sealed by the duckbill valve 81. Therefore, no gas leak occurs in this state.

After completion of the insufflation procedure, the endoscope 11 is inserted into the body cavity with the trocar 21 as the insertion port. Then, the treatment tool 22 is inserted into the body cavity with the trocar with camera 16 as the insertion port.

When the treatment tool 22 is inserted, by the action of the centering guide 91 which has the opening 91C and is harder than the dome type seal 88, it becomes easy to guide the treatment tool 22 to the opening 88C of the dome type seal 88.

When the treatment tool 22 is inserted, the opening 81C of the duckbill valve 81 is opened. The treatment tool 22 is inserted into the opening 88C of the dome type seal 88 of the airtight structure unit 42, and the opening 88C and the treatment tool 22 are in close contact with each other. Therefore, the seal by the duckbill valve 81 is released, but the airtight structure unit 42 maintains the seal of the internal space S2 (see FIG. 30) communicating with the insertion hole 33. In addition, since the dome type seal 88 has the single-piece configuration, the sealing performance is better than in the case where it is configured with a plurality of segments.

The medical staff ST performs a procedure by manipulating the treatment tool 22 while observing the body cavity through the composite image displayed on the monitor 19. The high flexibility of the dome type seal 88 ensures good operability of the treatment tool 22. Even if the treatment tool 22 moves in the radial direction, by the combination of the dome type seal 88, the bellows portion 89D of the airtight rubber cover 89, and the centering guide 91 whose hardness is higher than these, deformation of the opening 88C is prevented as shown in FIG. 32B. Sealing performance can be secured by preventing deformation of the opening 88C.

The present application is not limited to the above-described embodiment, but includes modifications in which the above-described embodiment is appropriately modified within the scope of the present application. For example, although the plurality of applications are included in the above-mentioned embodiment, they may be carried out alone or two or more applications may be combined appropriately. Also, in the above embodiment, the seal unit provided with the dome type seal and the centering guide can be applied to a normal trocar without a camera. Further, in the above embodiment, the trocar with camera 16 has only the imaging function. However, in addition to the imaging function, an illumination function for emitting illumination light may be provided. Also, the camera-less trocar apparatus without the camera section 36 may be provided with the illumination function.

EXPLANATION OF REFERENCES 10 laparoscope system
11 endoscope
11A insertion section
12 trocar with camera
12a white balance setting switch
16 trocar with camera
16A inner cylinder member
16B outer cylinder member
17 trocar shaft (obturator)
18 processor
18a white balance setting section for trocar image
18b white balance setting section for endoscopic image
19 monitor
20 console
21 trocar(trocar)
22 treatment tool
22A distal end
23 abdominal wall
23A fat
26, 27 incision part
28 camera unit
31 pipe section (cannula, cannula sleeve)
31A pipe section inner sleeve
31B pipe section outer sleeve
32 head section
32A head section inner sleeve
32B head section outer sleeve
33 insertion hole
35 engagement claw
36 camera section
41 slip resistance
42 airtight structure unit
43 rear cover
43A engagement hole
43B fitting groove
43C cutout
43D grip section
43E opening
43F slot
43G abutment surface
44 connector member
46 lock releasing member
46A operation section
46B supporting section
46C mount pin 46D mount hole
46E engaging projection
47 engaging member
47A, 47B engaging groove
49 connection port
51 cam plate
52 cam groove
52A first end
52B second end
52C guide groove
52D linear section
52E inclined section
53 shaft member
54 handle member
54A engaging claw
55 puncture member
55A outer peripheral surface
56 shaft member body
57 connecting member
57A body part
57B pressing part
58 pin arrangement plate
58A position mark
58B direction mark
58C inner peripheral surface
58D outer peripheral surface
58E extension part
59 cam pin
61 cutout
62 camera unit
62A imaging lens
62B lens barrel
63 mount
64 housing
64A upper face section
64B side face section
64C hook
65 rotation pin
66 mounting member
66A opening
66B bearing
67 bearing
67A distal side receiving opening
68 spring
71 spring
72 housing recess
72A hook
76 detachment prevention member
76A fixed end
76B free end
76C projecting section
78 ridge section
79 upper end part
81 duckbill valve
81A valve section
81B circular section
81C opening
81D flange
82 seal unit
82A peripheral edge
83 abutment surface
86 seal holder
86A cover section
86B cylinder section
86C opening
86D peripheral edge
87 first mount
87A mount section
87B flange
87C opening
88 dome type seal
88A seal section
88B flange
88C opening
88E small hole
89 airtight rubber cover
89A cylinder section
89B inner flange
89C opening
89D bellows portion
89E folded portion
91 centering guide
91A guide section
91B flange
91C opening
91E small hole
92 second mount
92A mount section
92B flange
92C opening
92D pin
93 segment
93A overlapping region
94 white part
95 blue part
96 green part
C1, C2 center line
D1, D2 maximum diameter
Lp coupling line
P patient
R1 region
R2 region
S1 internal space
S2 internal space
ST medical staff

What is claimed is:

1. A body cavity observation system comprising:
  a trocar with camera comprising:
    a trocar comprising a pipe section that is insertable into a body cavity;
    a trocar shaft configured to be attached to the trocar when the trocar is inserted into the body cavity, the trocar shaft comprising a puncture member at a distal end of the trocar shaft and a white part formed on a surface of the puncture member and the puncture member is configured to be exposed from a distal end of the pipe section; and
    a camera section disposed in a distal end area of the pipe section, the camera section configured to obtain a trocar image that comprises an image of the white part when the puncture member of the trocar shaft is exposed,
    wherein
    the camera section is displaceable between a storage position where the camera section is stored in the pipe section and a deployed position where the camera section is deployed in a direction projecting from an outer peripheral surface of the pipe section, and wherein the camera section is configured to perform imaging in the deployed position; and
  a processor configured to be connected to the trocar, the processor comprising a white balance setting section that is configured to set a white balance of subsequent trocar images based on the image of the white part in the trocar image.

2. A laparoscope system comprising:

the body cavity observation system according to claim 1, and an endoscope configured to be inserted in a trocar different from the trocar of the body cavity observation system, wherein the white part formed on the surface of the puncture member is configured to be illuminated with illumination light from the endoscope.

3. The laparoscope system according to claim 2, wherein the white balance for the trocar image is substantially the same as a white balance for an endoscopic image configured to be obtained by the endoscope.

4. A trocar apparatus configured to set a white balance of a trocar image configured to be obtained inside a body cavity, the trocar apparatus comprising:

a trocar comprising a pipe section that is insertable into the body cavity;

a trocar shaft configured to be attached to the trocar when the trocar is inserted into the body cavity, the trocar shaft comprising a puncture member at a distal end of the trocar shaft and a white part formed on a surface of the puncture member, and the puncture member is configured to be exposed from a distal end of the pipe section; and a camera section disposed in a distal end area of the pipe section, the camera section configured to obtain the trocar image comprising an image of the white part when the puncture member of the trocar shaft is exposed, wherein the camera section is displaceable between a storage position where the camera section is stored in the pipe section and a deployed position where the camera section is deployed in a direction projecting from an outer peripheral surface of the pipe section, and wherein the camera section is configured to perform imaging in the deployed position.

5. The trocar apparatus according to claim 4, further comprising:

a processor configured to be connected to the trocar, the processor comprising a white balance setting section that is configured to set a white balance of subsequent trocar images based on the image of the white part.

6. An operation method of a body cavity observation system, the body cavity observation system comprising a trocar with camera that comprises a pipe section that is insertable into a body cavity, a trocar shaft configured to be attached to the trocar when the trocar is inserted into the body cavity, the trocar shaft comprising a white part formed on a surface of a puncture member at a distal end of the trocar shaft, the puncture member configured to be exposed from a distal end of the pipe section, and a camera section disposed in a distal end area of the pipe section, the operation method comprising:

displacing the camera section between a storage position where the camera section is stored in the pipe section and a deployed position where the camera section is deployed in a direction projecting from an outer peripheral surface of the pipe section, and wherein the camera section performs imaging in the deployed position;

obtaining a trocar image, that comprises an image of the white part, by the camera section performing imaging; and setting a white balance for subsequent trocar images, by a white balance setting section, based on the image of the white part in the trocar image.

7. The body cavity observation system according to claim 1, wherein the camera section is configured to deploy to the deployed position by rotation of the trocar shaft.

* * * * *